(12) United States Patent
Ganapathy et al.

(10) Patent No.: US 11,975,306 B2
(45) Date of Patent: May 7, 2024

(54) SAMPLE PREPARATION COMPOSITIONS, DEVICES, SYSTEMS AND METHODS

(71) Applicant: PIERCE BIOTECHNOLOGY, INC., Carlsbad, CA (US)

(72) Inventors: Ramesh Ganapathy, Rockford, IL (US); Christopher Etienne, Rockford, IL (US); Deven Etnyre, Rockford, IL (US); Ashok Salunkhe, Rockford, IL (US); Atul Deshpande, Rockford, IL (US)

(73) Assignee: Pierce Biotechnology, Inc., Rockford, IL (US)

( * ) Notice: Subject to any disclaimer, the term of this patent is extended or adjusted under 35 U.S.C. 154(b) by 796 days.

(21) Appl. No.: 17/016,140

(22) Filed: Sep. 9, 2020

(65) Prior Publication Data

US 2021/0069673 A1     Mar. 11, 2021

Related U.S. Application Data

(60) Provisional application No. 62/898,370, filed on Sep. 10, 2019.

(51) Int. Cl.
*B01J 20/24* (2006.01)
*B01D 15/34* (2006.01)
(Continued)

(52) U.S. Cl.
CPC .............. *B01J 20/24* (2013.01); *B01D 15/34* (2013.01); *B01J 20/3042* (2013.01); *C07K 1/14* (2013.01)

(58) Field of Classification Search
CPC ........ B01D 15/34; B01J 20/24; B01J 20/3042; C07K 1/14
See application file for complete search history.

(56) References Cited

U.S. PATENT DOCUMENTS

| 3,607,739 A | 9/1971 | Thorborg |
| 4,257,884 A * | 3/1981 | Lim ...................... G01N 30/56 502/7 |

(Continued)

FOREIGN PATENT DOCUMENTS

| EP | 0906122 B1 | 9/2003 |
| WO | WO-2018087278 A1 | 5/2018 |

OTHER PUBLICATIONS

Anirudhan et al., "Removal and recovery of phosphate ions from aqueous solutions by amine functionalized epichlorohydrin-grafted cellulose", Desalination, vol. 285, Oct. 17, 2011, pp. 277-284.
(Continued)

*Primary Examiner* — James C Goloboy
(74) *Attorney, Agent, or Firm* — Klarquist Sparkman, LLP

(57) ABSTRACT

The present specification relates to compositions, devices, apparatus, methods, kits and systems for sample preparation (e.g., separation, reduction or removal of small molecules from biomolecules in a sample). Exemplary small molecules that can be separated, reduced or removed have a molecular weight range of <2000 Da. and may include, but are not limited to, dyes, biotin, affinity tags, crosslinkers, reducing agents, labels, nanoparticles, radioactive ligands, mass tags, unreacted molecules and combinations, intermediates and derivatives of the foregoing. Exemplary biomolecules present in a sample, include but are not limited to, proteins, glycoproteins, antibodies, peptides, nucleic acids, polysaccharides, carbohydrates and lipids. Methods, compositions, kits, devices, apparatus and systems of the disclosure may advantageously provide superior separation of small molecule contaminants and additionally reduce time and expenses related to separation of small molecules from larger biomolecules in samples. Biomolecules separated as set forth herein are amenable to better downstream processing.

19 Claims, 35 Drawing Sheets

(51) Int. Cl.
    *B01J 20/30*         (2006.01)
    *C07K 1/14*         (2006.01)

(56) References Cited

U.S. PATENT DOCUMENTS

| | | |
|---|---|---|
| 6,171,869 B1 | 1/2001 | Safarian et al. |
| 8,382,987 B2 | 2/2013 | Luchini et al. |
| 8,716,512 B2 | 5/2014 | Hsieh et al. |
| 8,858,800 B2 * | 10/2014 | Axen ............... B01J 39/19 |
| | | 210/656 |
| 9,453,045 B2 | 9/2016 | Gilljam et al. |
| 9,782,468 B2 | 10/2017 | Damotharan et al. |
| 9,867,852 B2 | 1/2018 | Weissman et al. |
| 2012/0156757 A1 * | 6/2012 | Iyer ............... B01D 15/362 |
| | | 530/413 |
| 2013/0244229 A1 * | 9/2013 | Bergstrom ......... B01J 20/3293 |
| | | 435/5 |
| 2017/0022248 A1 | 1/2017 | Son et al. |
| 2018/0086850 A1 | 3/2018 | Liao et al. |

OTHER PUBLICATIONS

PCT/US2020/049983, Search Report and Written Opinion, dated Dec. 18, 2020, 12 pages.
Office Action, dated May 7, 2023, issued for Chinese Patent Application No. 202080073045.5, 6 pages.

\* cited by examiner

SAMPLE PREPARATION COMPOSITIONS, DEVICES, SYSTEMS AND METHODS

FIELD

The present specification relates to compositions, devices, apparatus, methods, kits and systems for sample preparation (e.g., separation of small molecules from larger molecules). In some embodiments, the compositions, apparatus, devices, systems, methods and kits described herein can be used in for separation, extraction, purification, reduction or removal of small molecules from larger molecules such as but not limited to biomolecules in a sample.

BACKGROUND

Sample preparation techniques for isolating biomolecules are aimed at extracting biomolecules from other sample components and from sample processing components to enable downstream analysis and processing of the biomolecule. For example, during sample preparation of biomolecules such as proteins or nucleic acids, there is often a need to label the biomolecules with dyes, affinity tags, radioactive labels, mass tags and the like. In other instances, there is a need to chemically modify biomolecules such as to reduce, oxidize, cross-link, methylate, etc. During these treatments, some amount of the labeling agent or chemical agent remains in the sample either as an unreacted label/chemical, or in the form of a partially reacted intermediate or derivative. These unreacted small molecules can cause several issues during downstream analysis or use of the biomolecule. For example, free unreacted fluorescent dyes that have not conjugated with a protein or a nucleic acid cause background issues during fluorescent imaging of the protein or the nucleic acid.

Another example is preparation of tagged antibodies (e.g. such as biotinylated antibodies) that are typically used for detecting corresponding antigens. Streptavidin based supports are used with biotinylated antibodies for detection of antigens. If free unreacted biotin is present in a sample of biotinylated antibodies, it will interact with the streptavidin support and compromise binding capacity of the biotinylated antibodies.

Some methods used to address the removal of small molecules such as labels and chemical agents from larger molecules such as biomolecules include dialysis in combination with ion-exchange chromatography, size exclusion chromatography, or desalting resins in combination with ion exchange resins. However, each of these methods have several drawbacks.

For example, dialysis is commonly used to remove unreacted dyes, biotin and reducing agents from proteins. However, dialysis takes two to three buffer changes, and twelve to fourteen hours to remove small molecules.

Size exclusion chromatography is another method used to remove small molecules. This procedure requires complex and expensive chromatography instrumentation (such as AKTA system, GE). In these complex chromatography systems, a sample containing a small molecule is passed through a specific column that is customized and set up for the particular purpose and sample type. Typically, customized 1 ml, 5 ml, 10 ml or larger columns, depending on sample size, are set up. Larger biomolecules, such as an antibody conjugate, are excluded by the column first followed by the smaller molecules which pass through the pores. Hence, small molecules require more time to elute out of the column. Time for performing size exclusion chromatography can vary from thirty minutes to several hours depending on the column size, set up time etc. Size exclusion chromatographic methods are therefore expensive and time consuming.

Yet other procedures use desalting resins, where various resins are used for buffer exchange and desalting. However, desalting resins have a very limited capacity to remove small molecules such as dyes, labels and conjugates (as will also be shown in later parts of this specification).

Ion exchange resins in combination with desalting resins or dialysis have been used for separating small molecules wherein the ion exchangers on the resins interact with the small molecules. However, in addition to the disadvantages of dialysis and desalting resin based method that are listed above, protein recovery of ion exchange resins is poor because proteins have to be eluted out of the ion-exchanger. Ion exchange methods for protein elution require multiple steps which when combined with the additional need for dialysis or a desalting resin makes the process time consuming and tedious.

Accordingly, there is a need for better methods, compositions, systems and apparatus for the separation of larger biomolecules or larger molecules from small molecules such as free dyes, labels, reducing agents, crosslinkers and the like, that will enable cleaner downstream processing of the biomolecules in methods such as but not limited to fluorescent imaging, bioconjugation, immunoprecipitation etc.

SUMMARY

The present specification relates, in some embodiments, to compositions, apparatus, devices, methods, kits and systems for sample preparation, such as but not limited to, separation of small molecules from larger molecules (such as but not limited to biomolecules) in a sample. In some embodiments, compositions, apparatus, devices, systems, methods and kits described herein can be used in for separation, extraction, purification, elimination, reduction in quantity of small molecules or removal of small molecules from larger molecules in samples. In some embodiments, compositions, apparatus, devices, systems, methods and kits described herein substantially reduce the quantity of small molecules from biomolecules or larger molecules in samples. In some embodiments, compositions, apparatus, devices, systems, methods and kits described herein rapidly decrease the quantity of small molecules from biomolecules or larger molecules in samples. The terms biomolecule or larger molecule are used interchangeably in this specification. The term larger is only in relation to the small molecule to be removed and does not specify or limit the biomolecule to any particular size or size range.

Some examples of one or more small molecules that can be separated, extracted, reduced or removed by compositions, apparatus, devices, systems, methods and kits of the present disclosure include, but are not limited to, a dye, a derivative of a dye, biotin, a biotin derivative, a crosslinker, a reducing agent, oxidizing agent, a methylating agent, protein preservatives, a label, a nanoparticle, a radioactive ligand, a mass tag, an unreacted molecule and combinations, intermediates and derivatives thereof.

Dyes that are suitable for use are known to those skilled in the art and include, but are not limited to pyrene, coumarin, cyanine, benzofuran, a quinoline, a quinazolinone, an indole, a benzazole, a borapolyazaindacene and xanthenes including fluorescein, rhodamine and rhodol as well as other dyes described in RICHARD P. HAUGLAND, MOLECULAR PROBES HANDBOOK OF FLUORES- CENT PROBES AND RESEARCH CHEMICALS (11th edition, January 2010), which is herein incorporated by reference in its entirety.

In some embodiments, small molecules that can be separated by compositions, apparatus, devices, systems, methods and kits of the present disclosure include, have a molecular weight range of <2000 Da.

Exemplary larger molecules that can be separated from small molecules by compositions, apparatus, devices, systems, methods and kits of the present disclosure, include but are not limited to proteins, glycoproteins, antibodies, peptides, nucleic acids (DNA, genomic DNA, pDNA, RNA), polysaccharides, carbohydrates, lipids, toxins, nanoparticle and derivatives of each of the above listed molecules. Derivatives of molecules include without limitation tagged proteins or tagged nucleic acids; labeled molecules labeled with a variety of labels such as but not limited to dyes, fluorescent dyes, radioactive labels, affinity labels, mass-tags, metals, etc.; conjugated molecules including conjugated antibodies; molecules conjugated to nanoparticles such as gold-nanoparticles; molecules conjugated to toxins such as biotin-labeled toxins exemplifies in a non-limiting example by cholera-toxin labeled compound etc.; chemical derivatives of biomolecules such as but not limited to reduced proteins, oxidized proteins, methylated nucleic acids, proteins with sulfhydryl modified proteins. In some embodiments, larger molecules and biomolecules can be comprised in a sample.

One embodiment of the present disclosure relates to compositions for separating or extracting one or more small molecules from a sample. In some embodiments, a composition comprises a (at least one) size exclusion support and at least one moiety that can associate with the one or more small molecules, thereby separating the small molecules from the rest of the sample.

In some embodiments, contacting a sample with a composition of the present disclosure substantially reduces the quantity of the one or more small molecules from the sample.

Larger molecules present in the sample are size excluded by a composition of the disclosure. One or more small molecules remain associated with the composition via the at least one moiety.

In some embodiments, contacting a sample with a composition of a disclosure comprises without limitation one or more of the following: applying a sample onto the composition, passing the sample through the composition, allowing a sample to flow through the composition by gravity or by using a rotary or a centrifugal force, creating a positive or negative pressure differential to cause a sample to move through the composition.

In some embodiments, in a composition of the disclosure, at least one moiety is associated with the size exclusion support. In some embodiments, in a composition of the disclosure, at least one moiety is immobilized onto the size exclusion support. In some embodiments, in a composition of the disclosure, at least one moiety is attached to the size exclusion support.

In some embodiments, the at least one moiety associates with the one or more small molecules by charge interaction, hydrophilic interactions, hydrophobic interactions, affinity interaction, hydrogen bonding, Van der Waals forces or covalent bonding.

In some embodiments, a composition of the disclosure can comprise at least two moieties, or at least three moieties or at least four moieties, or at least five moieties etc.

In some embodiments, a size exclusion support used in the composition of the disclosure excludes molecules from samples that are equal to 2 kDa or greater than 2 kDa. In some embodiments, a size exclusion support used in the composition of the disclosure excludes molecules from samples that are equal to or greater than 3 kDa.

In some embodiments, a composition of the disclosure can comprise more than one size exclusion supports. For example, a composition can comprise at least a second size exclusion support and at least a second moiety. In some embodiments, a composition of the disclosure can further comprise a third size exclusion support, a fourth size exclusion support, a fifth size exclusion support, etc.

Each exclusion support can be associated with the same or different moieties. For example, in some embodiments, a first size exclusion support can be associated with one or more moieties, such as a first moiety, a second moiety, a third moiety, a fourth moiety, a fifth moiety etc. In other example embodiments, a first size exclusion support can be associated a first moiety, a second size exclusion support can be associated a second moiety, a third size exclusion support can be associated a third moiety, a fourth size exclusion support can be associated a fourth moiety, and a fifth size exclusion support can be associated a fifth moiety etc. Other combinations are also contemplated.

Compositions of the disclosure can in some embodiments comprise different ratios a variety of combinations of size exclusion supports and moieties. For example, a composition can comprise a ratio of a first size exclusion support and at least a first moiety and one or more additional moieties or one or more additional size exclusion supports and moieties. In another example, a composition can comprise a ratio of a first size exclusion supports and a first moiety and at least a second size exclusion support and at least a second moiety.

Compositions of the disclosure can also comprise blends of exclusion supports and moieties for example, a blend of a first size exclusion support and a first moiety and a second size exclusion support and a second moiety etc. or even a blend of a first size exclusion support and a first moiety, a second moiety (and third moiety and the like). Compositions comprising various combinations of one or more size exclusion supports and one or more moieties are contemplated.

In some embodiments, one or more moieties of a composition of the disclosure can comprise a polysaccharide, a dextran, a polyethylene glycol polymer, an amine-containing polymer, a polyaminoacids, an antibiotic, a chelating group, a magnetic particle, a paramagnetic particle, a functional group, an ion-exchanger and combinations thereof.

In some embodiments, an amine-containing polymer of a composition of the disclosure is a poly(ethylene glycol) diamine, a polyethylenediamine, a polyethyleneimine that is linear or a polyethyleneimine that is branched. In some embodiments, a polyethyleneimine that is linear is diethylenediamine.

In some embodiments of a composition of the disclosure, at least one moiety is a dextran. A variety of dextrans can be used. In some embodiments, a dextran used in a composition of the disclosure has a molecular weight in the range of from about 6 kDa-2800 kDa. In some embodiments, a dextran used in a composition of the disclosure has a molecular weight in the range of from about 1500 kDa-2800 kDa.

In some embodiments, a moiety used in a composition of the disclosure, is an ion-exchanger. The ion-exchanger is an anion exchanger or a cation exchanger. Non-limiting examples of ion exchangers include negatively charged hydroxyl groups, and positively charged pentylamine groups, diamines, imine groups.

In some embodiments, a moiety used in a composition of the disclosure, is a poly amino acid such as a polylysine, a polyhistidine, and/or a polyglutamate.

In some non-limiting exemplary embodiments, a composition of the disclosure can comprise: a first size exclusion support is associated with a first moiety, the first moiety for example comprising an amine-containing polymer (for example a polyethyleneglycol diamine) and the second size exclusion support is associated with a second moiety, the second moiety for example comprising a dextran.

In some other non-limiting exemplary embodiments, a composition of the disclosure can comprise: a first size exclusion support is associated with a first moiety comprising for example a poly(ethyleneglycol)diamine, a polyethylenediame, a polyethyleneimine that is linear or a polyethyleneimine that is branched, and the second size exclusion support is associated with a second moiety, the second moiety for example comprising a dextran.

In some other non-limiting exemplary embodiments, a composition of the disclosure can comprise: at least first size exclusion support associated with a first moiety comprising a poly(ethyleneglycol)diamine, and the first or a second size exclusion support is associated with a second moiety, the second moiety comprising a dextran.

In some other non-limiting exemplary embodiments, a composition of the disclosure can comprise: a first size exclusion support is associated with a first moiety comprising an N,N Diethylethylenediamine and the second size exclusion support is associated with a second moiety, the second moiety for example comprising a dextran.

In some non-limiting exemplary embodiments, a composition of the disclosure can comprise: a first size exclusion support is associated with a first moiety, the first moiety for example comprising an amine-containing polymer and the second size exclusion support is associated with a second moiety, the second moiety for example comprising a poly ethylene glycol polymer.

Compositions as described herein are comprised in devices, apparatus, systems and kits of the disclosure and used in one or more methods of the disclosure which are described in additional detail in sections infra.

In some embodiments, the present disclosure provides an apparatus and/or a device for separating, removing, or extracting one or more small molecules from a sample comprising: a) a container comprising: at least one size exclusion support and at least one moiety that can associate with the one or more small molecules; and b) a receptacle located below the container.

In some embodiments, the present disclosure provides a system for separating, removing, or extracting one or more small molecules from a sample comprising: a) a container comprising: a size exclusion support and at least one moiety that can associate with the one or more small molecules; and b) a receptacle located below the container. A system of the disclosure is configured to have forces such as but not limited to vacuum, gravity, negative or positive pressure applied to the sample in the container. In some embodiments, a system of the disclosure comprises a means to apply forces such as but not limited to vacuum, gravity, negative or positive pressure to the combination of the receptacle and container.

In some embodiments of a device, an apparatus, or a system of the disclosure, the receptacle is attached to the column. In some embodiments, the receptacle is detachable from the column. Contents of a receptacle can be removed by a user. A receptacle of the device collects sample with substantially reduced small molecules. An apparatus, a device or a system of the disclosure is operable to separate, reduce or remove one or more small molecules from a sample in a single step. A device, an apparatus or a system of the disclosure is operable to have forces such as but not limited to vacuum, gravity, negative or positive pressure applied to the sample in the container.

In some embodiments of a device, an apparatus, or a system of the disclosure, is operably configured to be subject to a gravity flow, a centrifugal force, a positive pressure, a negative pressure, vacuum and combinations thereof.

In some embodiments of a device, an apparatus, or a system of the disclosure, the container is a columnar container, a tube, a multi-well tube, a multi-well plate or a multi-well filter plate. Exemplary containers include but are not limited to a spin column, a multi-well plate, a multi-well filter plate, a micro-well plate, a micro-well filter plates.

Systems, apparatus and devices of the disclosure, in embodiments, comprise a container comprising one or more compositions of the disclosure as set forth in the sections supra and infra.

In some embodiments, the present disclosure describes a kit for separating a biomolecule from one or more small molecules comprising: a device comprising: a) a container comprising a size exclusion resin and at least one moiety that can associate with the at least one small molecule and capture said small molecule; and b) a receptacle located below the container, wherein the device is operably configured to be subject to a gravity flow, a centrifugal force, a positive pressure, a negative pressure, vacuum and combinations thereof.

Kits of the disclosure can comprise one or more compositions, one or more devices, apparatus and/or systems as set forth herein. In some embodiments, a kit of the disclosure comprises at least two or more moieties that can associate with the one or more small molecules.

In some embodiments of a kit of the disclosure the device is a spin column, a multi-well filter plate, or a multi-well plate. A kit can further comprise one or more buffers packaged in one or more separate containers or included in the first container.

In some embodiments, the present disclosure describes a method for separating a biomolecule from one or more small molecules comprising: a) applying a sample to a container comprising a size exclusion support and at least one moiety that can bind to at least one small molecule; and b) subjecting the container to a gravity flow, a centrifugal force, a positive pressure, a negative pressure, a vacuum or a combination thereof, wherein the biomolecule in the sample is excluded through the size exclusion support and is collected as a flow through, and wherein the at least one small molecule associates with the at least one moiety and is thereby separated from the sample.

In some embodiments of a method of the disclosure, separation of an at least one small molecule from the remainder of the sample is carried out in one step. In some embodiments of a method of the disclosure, flow through is collected in a receptacle located below the container.

Methods, compositions, kits, devices, apparatus and systems of the disclosure advantageously provide superior separation of small molecules and additionally reduce time and expenses related to separation of small molecules from larger biomolecules in samples. Larger biomolecules separated as set forth herein are amenable to better downstream processing. While specific advantages have been disclosed hereinabove, it will be understood that various embodiments may include all, some, or none of the previously disclosed advantages. Other technical advantages may become readily apparent to those skilled in the art in light of the teachings of the present disclosure.

These and other features of the present teachings will become more apparent from the detailed description in sections below.

BRIEF DESCRIPTION OF THE DRAWINGS

One or more embodiments of the present disclosure may be better understood in reference to one or more the drawings below. The skilled artisan will understand that the drawings, described below, are for illustration purposes only. The drawings are not intended to limit the scope of the present teachings in any way.

DETAILED DESCRIPTION

Figure 1A:
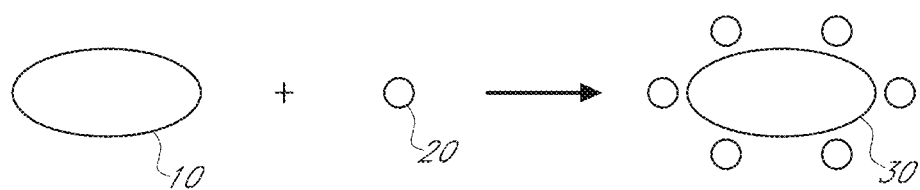
FIG. 1A depicts a schematic of a size exclusion support associating with a moiety to form an exemplary composition, according to one embodiment of the disclosure.

It is to be understood that both the foregoing general description and the following detailed description are exemplary and explanatory only and are not intended to limit the scope of the current teachings. In this application, the use of the singular includes the plural unless specifically stated otherwise. For example, the singular forms "a", "an" and "the" as used in the specification also include plural aspects unless the context dictates otherwise. Similarly, any singular term used in the specification also mean plural or vice versa unless the context dictates otherwise.

Also, the use of "comprise", "contain", and "include", or modifications of those root words, for example but not limited to, "comprises", "contained", and "including", are not intended to be limiting. Use of "or" means "and/or" unless stated otherwise. The term "and/or" means that the terms before and after can be taken together or separately. For illustration purposes, but not as a limitation, "X and/or Y" can mean "X" or "Y" or "X and Y".

Whenever a range of values is provided herein, the range is meant to include the starting value and the ending value and any value or value range therebetween unless otherwise specifically stated. For example, "from 0.2 to 0.5" means 0.2, 0.3, 0.4, 0.5; ranges therebetween such as 0.2-0.3, 0.3-0.4, 0.2-0.4; increments there between such as 0.25, 0.35, 0.225, 0.335, 0.49; increment ranges there between such as 0.26-0.39; and the like.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

The terms "separation," "extraction," "extracted," "removal," "reducing" or "reducing the quantity of," or "purification" all refer to the act or process of removing or isolating a substance (e.g., a small molecule such as a label or a chemical agent, or a larger molecule or a biomolecule such as DNA, RNA, protein) from a mixture (of several components such as cellular components, or materials in a sample in which the small molecule and/or biomolecule and/or larger molecule is comprised in). An extracted substance or a sample from which a substance has been extracted from has significantly decreased quantities of components that it was present in and can be substantially reduced, substantially removed, substantially pure, or pure (devoid of any contaminants), or concentrated or substantially concentrated as compared to prior to being extracted.

The term "small molecule" generally refers to any molecule smaller than a large molecule (such as but not limited to a biomolecule) that is being used to treat, derivatize, conjugate, cross-link, label, tag, or chemically or biologically modified the larger molecule for further analysis. Larger molecules and/or biomolecules including proteins, glycoproteins, antibodies, nucleic acids (DNA, genomic DNA, pDNA, RNA), polysaccharides, carbohydrates, lipids, and some other larger molecules such as toxins, nanoparticle are often derivatized by variety of treatments prior to additional analysis or use. Derivatization includes labeling molecules with labels such as dyes, affinity tags, radioactive labels, mass tags, metals and the like. Derivatization also includes chemically modifying molecules by reduction, oxidization, methylation, biologically or biochemically modifying biomolecules etc. Derivatives of biomolecules include without limitation tagged proteins or nucleic acids; labeled biomolecules labeled with a variety of labels such as but not limited to dyes, fluorescent dyes, radioactive labels, affinity labels, mass-tags, metals, etc.; conjugated biomolecules including conjugated antibodies; biomolecules conjugated to nanoparticles; metals such as gold conjugated to nanoparticles; dyes or labels such as biotin conjugated to toxins; chemical derivatives of biomolecules such as but not limited to reduced proteins, oxidized proteins, methylated nucleic acids, proteins with sulfhydryl modified proteins.

Methods of derivatization often leave behind "small molecule" byproducts in samples such as but not limited to unreacted free labels, partially reacted labels, derivatives of unreacted free labels including free dyes, derivatives of dyes, free radioactive ligands, intermediates of radioactive ligands, free mass tags, free metals, biotin, biotin derivatives, crosslinkers and their derivatives, excess reducing agents or their derivatives, unreacted nanoparticles, other unreacted, partially reacted or intermediate molecules and combinations, intermediates and derivatives thereof. Since these unreacted small molecules can cause several issues during downstream analysis or use of the larger molecule, there is a need to separate, extract, remove or reduce the quantity of "small molecules" from larger molecules and their derivatives during sample preparation. In some embodiments, small molecules that can be separated, extracted or removed by a composition, a device, an apparatus, a system, a kit and a method of the disclosure are typically <2 kDa.

The term "support" refers to an inert porous solid. The term "size exclusion support" describes an inert porous solid that has a porosity which determines the size of a molecule that may be included or excluded from entering the pores. In some embodiments, pore size of a size exclusion support is equal to 2 kDa. In some embodiments, the pores of a size exclusion support of the present disclosure has a molecular size cut-off of 2 kDa and hence molecules that are excluded are those that are 2 kDa or greater than 2 kDa. In some embodiments, pore size of a size exclusion support is >2 kDa. In some embodiments, the pores of a size exclusion support of the present disclosure has a molecular size cut-off of about >2 kDa and hence molecules that are excluded are those above 2 kDa. In one of the embodiments, the pore size of the size exclusion column has a molecular size cut-off size for excluding from the pores molecules of about 2 kDa to about 150 kDa, about 5 kDa to about 150 kDa, including ranges in between, such as but not limited to 2 kDa, 3 kDa, 5 kDa, 7 kDa, 10 kDa, 15 kDa, 20 kDa, 30 kDa, 40 kDa, 50 kDa, 60 kDa, 70 kDa, 80 kDa, 90 kDa, 100 kDa, 110 kDa, 120 kDa, 130 kDa, 140 kDa, and 150 kDa. In some embodiments, there is no upper limit for the size of proteins that can be excluded and mega Dalton size molecules are also envisioned to be separated from small molecule impurities or contaminants by compositions, devices, systems, kits and methods of the present disclosure.

The section headings used herein are for organizational purposes only and are not to be construed as limiting the subject matter described in any way. All literature and similar materials cited in this application including, but not limited to, patents, patent applications, articles, books, treatises, and internet web pages, regardless of the format of such literature and similar materials, are expressly incorporated by reference in their entirety for any purpose. In the event that one or more of the incorporated literature and similar materials defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art in light of the present teachings.

Compositions:

One embodiment of the present disclosure describes compositions for separating, extracting, removing, and/or reducing the quantity of one or more small molecules from larger biomolecules. Present compositions comprise a size exclusion support and at least one moiety that can associate with the one or more small molecules, thereby separating the small molecules from the other components (such as larger biomolecules) present in a sample.

A size exclusion support typically comprises spherical beads made of a gel or a gel like material having pores. Some exemplary size exclusion supports are made of dextran polymers, agarose, polyacrylamide, cellulose materials and derivatives thereof. The pore size range of a size exclusion support determines the size of a molecule that may be included or excluded from entering the size exclusion support.

When a sample solution is applied on a size exclusion support it travels down the support and smaller sample components enter into the pores. Sample components that are larger than the pore size cannot enter into the pores. Therefore, larger sample components are excluded and elute out of the size exclusion column faster than smaller components that are trapped in pores.

Present compositions comprise a combination of at least one size exclusion support and at least one moiety that can associate with one or more small molecule. The present compositions therefore provide separation of small molecules from larger biomolecules of a sample by a combination of size exclusion, size inclusion as well as separation by association of small molecules onto the at least one moiety. The inventors have found that the present compositions provide unexpectedly rapid, economical and efficient separation of small molecules from larger biomolecules.

In some embodiments, a composition of the disclosure comprises at least one moiety that is associated with at least one size exclusion support. In some embodiments, a composition of the disclosure comprises at least one moiety that is immobilized onto at least one size exclusion support.

Figure 1B:
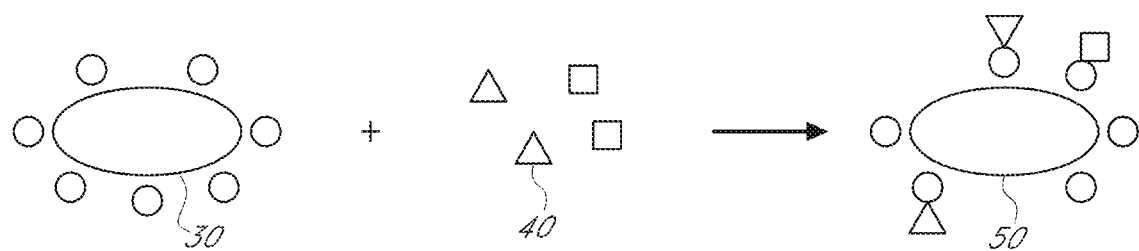
FIG. 1B depicts a schematic of a composition of the disclosure associating with one or more small molecules, according to one embodiment of the disclosure.

FIG. 1A depicts a schematic of an exemplary size exclusion support 10 associating with a moiety 20 to form an exemplary composition 30, according to one embodiment of the disclosure. FIG. 1B depicts a schematic of a composition 30 of the disclosure associating with one or more small molecules 40, to form a complex 50, according to one embodiment of the disclosure.

Figure 2A:
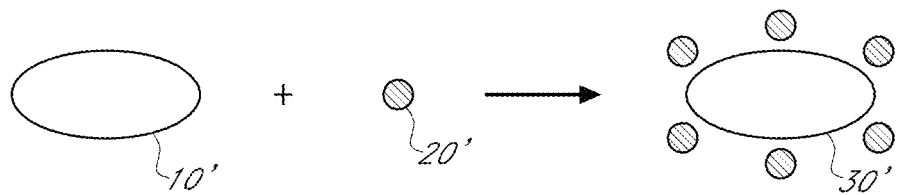
FIG. 2A depicts a schematic of a non-limiting exemplary composition of the disclosure, according to one embodiment of the disclosure.
Figure 2B:
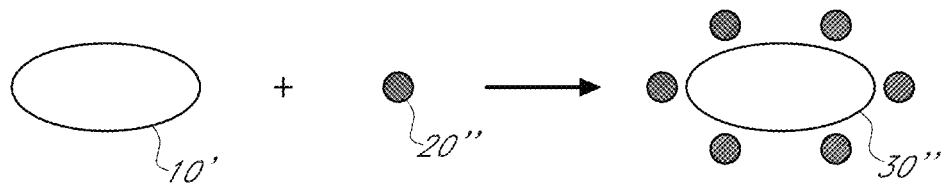
FIG. 2B depicts a schematic of a non-limiting exemplary composition of the disclosure, according to one embodiment of the disclosure.

FIG. 2A depicts a schematic of another non-limiting exemplary composition 30' of the disclosure comprising an exemplary size exclusion support 10' associating with a moiety 20', according to one embodiment of the disclosure. FIG. 2B depicts a yet another non-limiting exemplary composition 30" of the disclosure comprising an exemplary size exclusion support 10' associating with a moiety 20", according to one embodiment of the disclosure. These drawings are non-limiting exemplary compositions used to illustrate some possible compositions. One of skill in the art, in light of the descriptions and drawings herein, will realize that several other combinations of compositions are contemplated by the disclosure.

In some embodiments, immobilization is by formation of a covalent bond such as but not limited to formation bonds such as an amide bond, alkylation, amination, amidation, covalent amine forming bond or covalent amide forming bond between a size exclusion support and a moiety. In some embodiments, a size exclusion supports comprises a dextran polymer, agarose, polyacrylamide, a cellulose material and derivatives thereof. In some example embodiments, a size exclusion support comprises hydroxyethylcellulose. In an exemplary immobilization, according to the disclosure, a hydroxyethyl cellulose can be periodate oxidized to generate aldehyde groups. These generated aldehyde groups can react with terminal amines on exemplary moieties (such as but not limited to a pentylamine (which can be used as a spacer molecule) or a poly(ethyleneglycol)bisamine to form Schiff base intermediates. The labile Schiff base interaction is chemically stabilized by reduction using chemicals such as sodium cyanoborohydride to form a secondary amine bond.

In some embodiments, pore size of a size exclusion support is equal to 2 kDa or >2 kDa. In these exemplary compositions, molecules that are excluded from the pores are those that are 2 kDa or those that are above 2 kDa.

Biomolecules of 2 kDa or above 2 kDa elute out from these compositions. In some exemplary embodiments, the pore size of the size exclusion support is from about >2 kDa to about 50 kDa, >2 kDa to about 75 kDa, >2 kDa to about 100 kDa, >2 kDa to about 150 kDa, >2 kDa to about 200 kDa. In some embodiments, the pore size of the size exclusion support is from about 7000 Da to about 50,000 Da. In some embodiments, there is no upper limit for the size of proteins that can be excluded and Mega Dalton size molecules and larger are also envisioned to be separated from small molecule impurities or contaminants by compositions, devices, systems, kits and methods of the present disclosure.

In some embodiments, a composition of the present disclosure (when contacted with a sample) substantially reduces the quantity of the one or more small molecules from the sample. In some embodiments, contacting a sample with a composition of a disclosure comprises without limitation one or more of the following: applying a sample onto the composition, passing the sample through the composition, allowing a sample to flow through the composition by gravity or by using a rotary or a centrifugal force, creating a pressure differential to cause a sample to move through the composition.

In some embodiments, the at least one moiety associates with the one or more small molecules by charge interaction, hydrophilic interactions, hydrophobic interactions, affinity interaction, hydrogen bonding, Van der Waals forces, or covalent bonding.

Figure 2C:
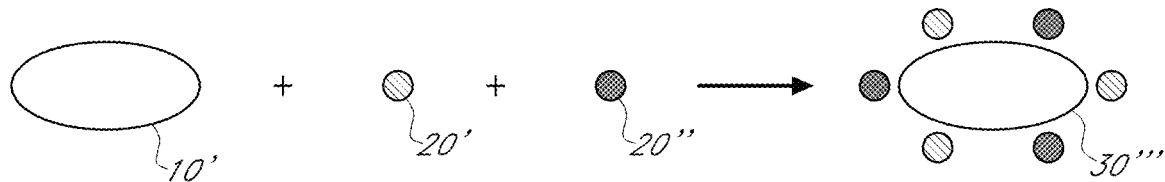
FIG. 2C depicts a schematic of a non-limiting exemplary composition of the disclosure, according to one embodiment of the disclosure.

In some embodiments, a composition of the disclosure can comprise at least two moieties, or at least three moieties or at least four moieties, or at least five moieties etc. FIG. 2C depicts a schematic of a non-limiting exemplary composition 30''' of the disclosure comprising an exemplary size exclusion support 10' associating with at least two moieties 20' and 20", according to one embodiment of the disclosure. These drawings are non-limiting exemplary compositions used to illustrate some possible combinations of different number of moieties. One of skill in the art, in light of the descriptions and drawings herein, realize that several other combinations of compositions are contemplated by the disclosure and the illustrations do not limit the scope of the teachings herein.

In some embodiments, a size exclusion resin excludes molecules from the sample that are equal to 2 kDa. In some embodiments, a size exclusion resin excludes molecules from the sample that are >2 kDa. In some embodiments, a size exclusion resin excludes molecules from the sample that are >3 kDa. In some embodiments, a size exclusion resin excludes molecules from the sample that are >5 kDa.

In some embodiments, a composition of the disclosure can further comprise at least a second size exclusion support. In some embodiments, a composition of the disclosure can further comprise a third size exclusion support, a fourth size exclusion support, a fifth size exclusion support, etc. In some embodiments, a composition of the disclosure can further comprise and at least a second moiety, at least a third moiety, a fourth moiety, a fifth moiety etc. One size exclusion support can comprise one or more different type of moieties. Alternatively, different size exclusion supports can comprise the same moiety or different types of moieties.

Compositions of the disclosure, in some embodiments, comprise different ratios of various combinations of one or more size exclusion supports and one or more moieties as described herein. For example, a composition of the disclosure, comprises different ratios of a first size exclusion support and at least a first moiety and a second size exclusion support and at least a second moiety. Another exemplary composition of the disclosure, comprises different ratios of a first size exclusion support and at least a first moiety and the first size exclusion support and at least a second moiety. Yet another exemplary composition of the disclosure, comprises different ratios of a first size exclusion support and at least a first moiety and the first size exclusion support and at least a first and a second moiety (and third moiety and the like). Compositions are contemplated that can facilitate the separation or removal or one or more small molecules from one or more biomolecules present in a sample by application of the sample onto a single composition.

Figure 2D:
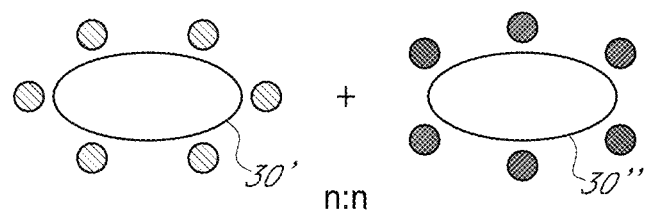
FIG. 2D depicts a schematic of a non-limiting exemplary composition of the disclosure, according to one embodiment of the disclosure.
Figure 2E:
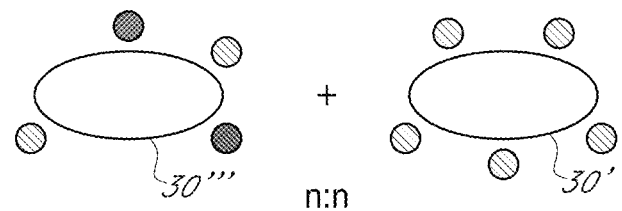
FIG. 2E depicts a schematic of a non-limiting exemplary composition of the disclosure, according to one embodiment of the disclosure.
Figure 2F:
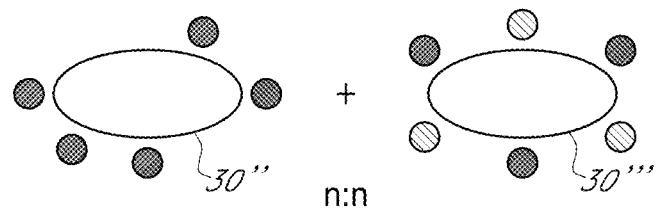
FIG. 2F depicts a schematic of a non-limiting exemplary composition of the disclosure, according to one embodiment of the disclosure.

FIG. 2D depicts a schematic of a non-limiting exemplary composition comprising a blend of compositions 30' and 30" in a ratio n:n (where each n can independently be a number of 1-9, for example ratios such as 1:1, 2:1:3:4; 1:5 and the like). FIG. 2E depicts a schematic of another non-limiting exemplary composition comprising a blend of compositions 30''' and 30' in a ratio n:n (where each n can independently be a number of 1-9. FIG. 2F depicts a schematic of yet another non-limiting exemplary composition comprising a blend of compositions 30" and 30''' in a ratio n:n (where each n can independently be a number of 1-9. These drawings are non-limiting exemplary compositions used to illustrate some possible compositions. One of skill in the art, in light of the descriptions and drawings herein, will realize that several other blends of compositions and combinations of compositions are contemplated by the disclosure.

In some embodiments, one or more moieties of a composition of the disclosure can comprise a polysaccharide, a polyethylene glycol polymer, an amine-containing polymer, a polyaminoacids, an antibiotic, a chelating group, a magnetic particle, a paramagnetic particle, a functional group, an ion-exchanger and combinations thereof.

Exemplary amine-containing polymers that can be used in a composition of the disclosure include but are not limited to a poly(ethylene glycol)diamine, a polyethylenediame, a polyethyleneimine that is linear or a polyethyleneimine that is branched. An exemplary polyethyleneimine that is linear is diethylenediamine.

In some exemplary compositions of the disclosure, one or more polysaccharide moieties can be one or more dextrans. A variety of dextrans can be used. In some embodiments, a dextran used in a composition of the disclosure has a molecular weight in the range of from about 6 kDa-2800 kDa. In some embodiments, a dextran used in a composition of the disclosure has a molecular weight in the range of from about 1500 kDa-2800 kDa.

In some embodiments, a moiety used in a composition of the disclosure, is an ion-exchanger such as an anion exchanger or a cation exchanger. An anion exchanger moiety can bind to small molecules with negative charges and leave sample components that are positively charged. A cation exchanger can bind small molecules with positive charges and leave sample components that are negatively charged. Non-limiting examples of ion exchangers include negatively charged hydroxyl groups, positively charged pentylamine groups, diamines, and imine groups.

In some exemplary compositions of the disclosure, one or more polyaminoacids moieties can be a polylysine, a polyhistidine, a polyglutamine, a polyasparagine or the like. In some embodiments, a polyamino acid moieties can remove or separate endotoxins from other larger biomolecules.

In some embodiments, either a size exclusion support or a moiety can include a reactive functional group. A functional group on a size exclusion support can be used to interact with and associate with one or more moieties to form a composition. A functional group on a moiety can be used to interact with and associate with one or more small molecules to be separated or extracted from the larger biomolecule. Functional groups can comprise but are not limited to, hydroxyl, carboxyl; amino, thiol, aldehyde; halogen, nitro, cyano, amido, urea, carbonate, carbamate, isocyanate, sulfone, sulfonate, sulfonamide, sulfoxide, etc., groups for associating or interacting with moieties or small molecules.

In another embodiment, functional groups include at least one reactive group represented by either $R_x$, which represents a reactive functional moiety, or (-L-$R_x$), which represents a reactive functional moiety $R_x$ that is attached to either a size exclusion support or a moiety by a covalent linkage L. The reactive group functions as the site of association, attachment and/or interaction with a moiety or a small molecule wherein the reactive group chemically reacts with an appropriate reactive or functional group on the solid support, the moiety or the small molecule. In an exemplary embodiments, a reactive group or a functional group can be an acrylamide, an activated ester of a carboxylic acid, an acyl halide group, an acyl azide, an acyl nitrile, an aldehyde, an alkyl halide, an anhydride, an aniline, an aryl halide, an azide, an aziridine, a boronate, a thioboronate group, a carboxylic acid, a diazoalkane, a haloacetamide, a halotriazine, a hydrazine, a hydrazide, an imido ester, an isocyanate, an isothiocyanate, a maleimide, a phosphoramidite, a sulfonyl halide, a thiol group, a sulfide group, a disulfide group, an epoxide group, and episulfide group, a thioester group, an alcohol group, an activated alcohol group, a phosphate group, a phosphate ester group, and a photoactivatable group.

In another exemplary embodiment, a reactive group or functional group can comprise electrophiles and/or nucleophiles and can in some embodiments generate a covalent linkage between them. Exemplary electrophiles and nucleophile functional groups can include activated esters, generally have the formula —COΩ, where Ω is a good leaving group (e.g. oxysuccinimidyl (—$OC_4H_4O_2$) oxysulfosuccinimidyl (—$OC_4H_3O_2$—$SO_3H$), -1-oxybenzotriazolyl (—$OC_6H\ N_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —$OCOR^a$ or —$OCNR^a$-$NHR^b$, where $R^a$ and $R^b$, which may be the same or different, are $C_1$-$C_6$ alkyl, $C_rC_6$ perfluoroalkyl, or $C_1$-$C_6$ alkoxy; or cyclohexyl, 3-dimethylaminopropyl, an acyl halide group, an acyl nitrile, an aldehyde, an alkyl halide, an anhydride, an aryl halide, an aziridine, a diazoalkane, a haloacetamide, a halotriazine, an isocyanate, an isothiocyanate, a maleimide, a phosphoramidite, a sulfonyl halide, a sulfide group, a disulfide group, an epoxide group, and episulfide group, a thioester group, an activated alcohol group, a phosphate group, a phosphate ester group, and a photoactivatable group. Acyl azides can also rearrange to isocyanates.

In some embodiments, the reactive group further comprises a linker, L, in addition to the reactive functional moiety. The linker can be used to covalently attach a reactive functional group. When present, the linker is a single covalent bond or a series of stable bonds. A reactive functional moiety may be directly attached (where the linker is a single bond) through a series of stable bonds, to the solid support, the moiety or to the small molecule or attached. When the linker is a series of stable covalent bonds the linker typically incorporates several nonhydrogen atoms selected from the group consisting of C, N, O, S, Si, B and P. In addition, the covalent linkage can incorporate a platinum atom, such as described in U.S. Pat. No. 5,714,327. When the linker is not a single covalent bond, the linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. In an exemplary embodiment, the linker incorporates less than 15 nonhydrogen atoms and are composed of a combination of ether, thioether, thiourea, amine, ester, carboxamide, sulfonamide, hydrazide bonds and aromatic or heteroaromatic bonds. Typically, the linker is a single covalent bond or a combination of single carbon-carbon bonds and carboxamide, sulfonamide or thioether bonds. The following moieties can be found in the linker: ether, thioether, carboxamide, thiourea, sulfonamide, urea, urethane, hydrazine, alkyl, aryl, heteroaryl, alkoxy, cycloalkyl and amine moieties. Examples of L include substituted or unsubstituted polymethylene, arylene, alkylarylene, arylenealkyl, or arylthio.

Any combination of linkers can be used to attach functional or reactive groups. Where the reactive group is a maleimide or haloacetamide the resulting compound is particularly useful for conjugation to thiol-containing substances. Where the reactive group is a hydrazide, the resulting compound is particularly useful for conjugation to periodate-oxidized carbohydrates and glycoproteins. Where the reactive group is a silyl halide, the resulting compound is particularly useful for conjugation to silica surfaces, particularly where the silica surface is incorporated into a fiber optic probe subsequently used for remote ion detection or quantitation.

In some non-limiting exemplary embodiments of a composition of the disclosure, a first size exclusion support is associated with a first moiety, the first moiety for example comprising an amine-containing polymer and the second size exclusion support is associated with a second moiety, the second moiety for example comprising a dextran.

In some other non-limiting exemplary embodiments of a composition of the disclosure, a first size exclusion support is associated with a first moiety comprising for example a poly(ethyleneglycol)diamine, a polyethylenediamine, a polyethyleneimine that is linear or a polyethyleneimine that is branched, and the second size exclusion support is associated with a second moiety, the second moiety for example comprising a dextran.

In some other non-limiting exemplary embodiments of a composition of the disclosure, a first size exclusion support is associated with a first moiety comprising diethylenediamine and the second size exclusion support is associated with a second moiety, the second moiety for example comprising a dextran.

In some non-limiting exemplary embodiments of a composition of the disclosure, a first size exclusion support is associated with a first moiety, the first moiety for example comprising an amine-containing polymer and the second size exclusion support is associated with a second moiety, the second moiety for example comprising a poly ethylene glycol polymer.

Apparatus and Devices:

In some embodiments, the present disclosure provides an apparatus and/or a device and/or a system for removing one or more small molecules from a sample comprising: a) a container comprising: at least one size exclusion support and at least one moiety that can associate with the one or more small molecules; and b) a receptacle located below the container. In some embodiments of a device, an apparatus, or a system of the disclosure, the receptacle is attached to the column. In some embodiments, the receptacle is detachable from the column. Contents of a receptacle can be removed by a user. In some embodiments, a receptacle of the device collects sample with substantially reduced small molecules. In some embodiments, a receptacle of the device collects sample with no small molecules.

In some embodiments of a device, an apparatus, or a system of the disclosure, is operably configured to be subject to a gravity flow, a centrifugal force, a positive pressure, a negative pressure, vacuum and combinations thereof. Structures that allow applications of the above-mentioned pressures or forces include without limitation a syringe that can be drawn to cause a positive pressure, a vacuum frit for generating negative pressure, tubes or containers adaptable to commercially available centrifuges or rotatory devices.

An apparatus, a device or a system of the disclosure is operable to separate, reduce the quantity of or remove one or more small molecules from a sample by a single application of sample to device and subjecting the device, apparatus or system of the disclosure to one or more forces such as but not limited to vacuum, gravity, negative or positive pressure applied to the sample in the container.

In some embodiments of a device, an apparatus, or a system of the disclosure, the container is a columnar container, a tube, a multi-well tube, a multi-well plate or a multi-well filter plate. Exemplary containers include but are not limited to a test tube, a spin column, a multi-well plate, a multi-well filter plate, a micro-well plate, or a micro-well filter plate.

Figure 3:
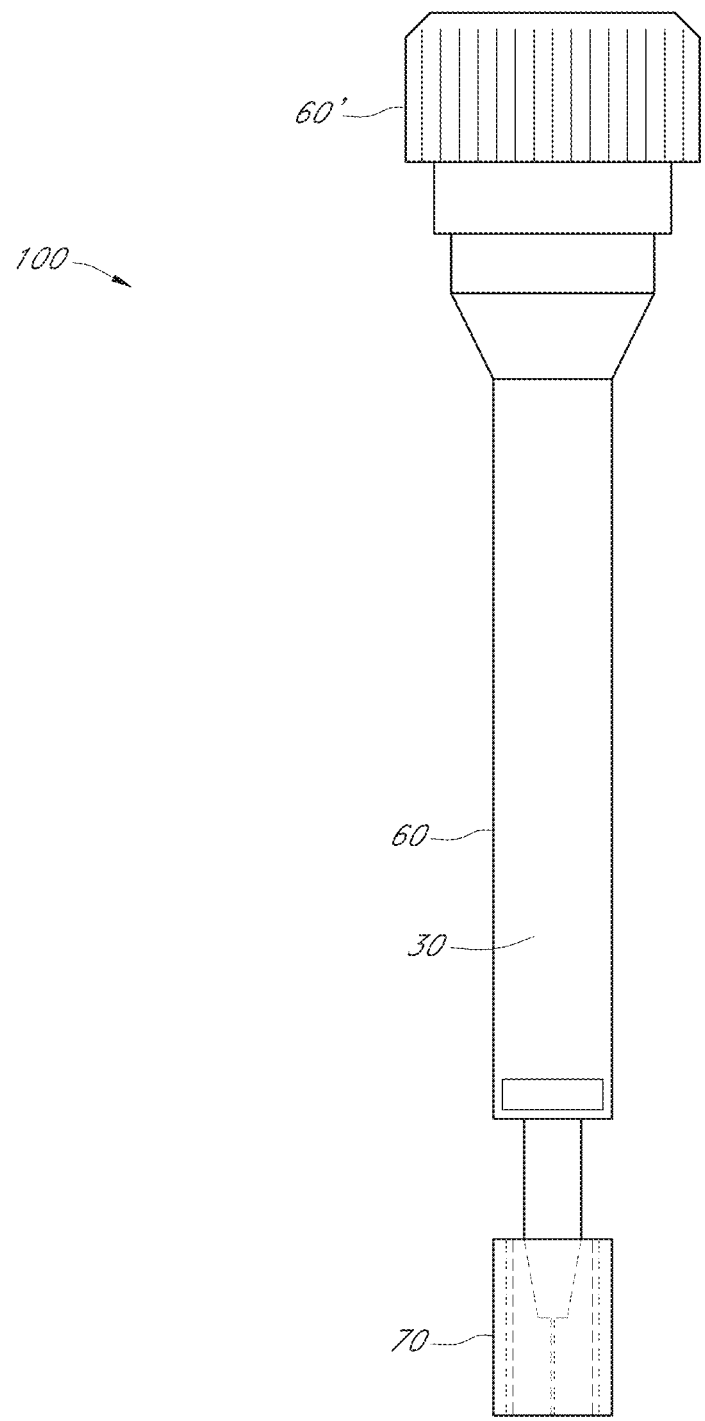
FIG. 3 depicts a three-dimensional (3-D) view of an exemplary apparatus/device, according to one embodiment of the disclosure.

FIG. 3 depicts a non-limiting three-dimensional (3-D) view of an exemplary apparatus/device or system, 100, according to one embodiment of the disclosure that comprises a container 60 (such as a columnar tube, a test-tube or a spin column), container 60 having a filter, a mesh or a porous surface area at the bottom end of the container (not depicted). Container 60 can also comprise one or more frits (not depicted). Container 60 comprises or contains inside an example composition 30 (at least one size exclusion support and at least one moiety that can associate with the one or more small molecules), an optional lid 60' that can be used to secure container 60 at the top end. A receptacle 70 is located below the container 60 that is adaptable or configured to receive the eluate or flow-through from the container through its bottom end. Receptacle 70 can be detached from container 60 so a user can collect the flow-through or eluate. In some embodiments receptacle 60 has a twist-off tab configuration for removal. In other embodiments receptacle 70 can be attached to container 60 by grooves or threads that can be attached and removed by manual or mechanical means such as rotating, twisting-off, or attachment by complementary fit that can be pulled apart and the like.

Figure 4A:
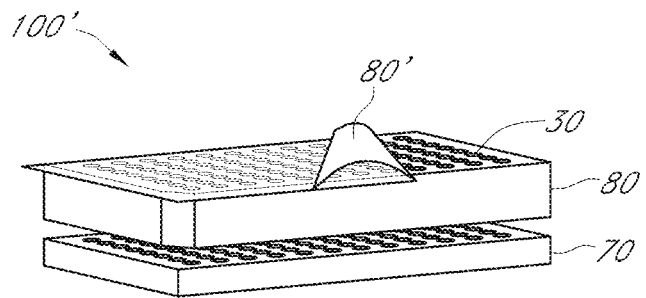
FIGS. 4A and 4B depict three-dimensional (3-D) views of an exemplary apparatus/device, according to one embodiment of the disclosure.
Figure 4B:
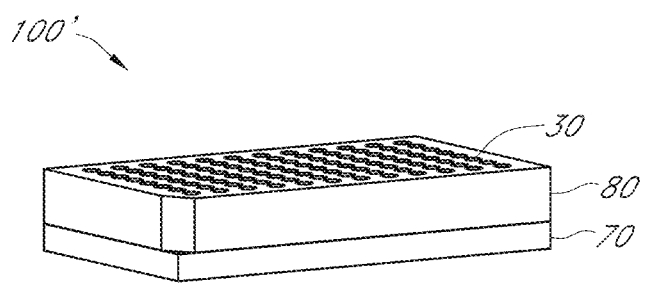

FIG. 4A and FIG. 4B depicts a non-limiting three-dimensional (3-D) view of an exemplary apparatus/device or system, 100', according to one embodiment of the disclosure that comprises a multi-well container 80 having disposed inside each well an example composition 30 (at least one size exclusion support and at least one moiety that can associate with the one or more small molecules), an optional lid 80' for the container. 80' can be a foil, a clear wrap, a tear-off seal and/or a removable/detachable lid of any kind.

Multi-well container 80 can be a multi-well plate, a multi-well plate filter, a microplate or a microliter plate and comprises a flat plate with multiple-wells where each well is used as a small test tube or container. Multi-well plates come in a variety of formats for high-throughput use and can typically have 6, 12, 24, 48, 96, 384, 1536, 3456, 9600 or more wells arranged in a rectangular matrix or array.

Multi-well container 80 can have a receptacle 70 located below the container that is adaptable or configured to receive the eluate or flow-through from the container. A multi-well filter plates, container 80 can have a mesh, filter or other type of porous bottom surface through which flow-through or eluate can flow into receptacle 70 (not shown).

In some embodiments, receptacle 70 such is a multi-well tray (see for example FIG. 4A) to collect eluate or flow through. Receptacle 70 is detachable and eluate can be collected from it by a user (see FIGS. 4A and 4B). In some embodiments receptacle 70 is a wash plate or a collection plate.

It will be understood that FIG. 3, FIG. 4A and FIG. 4B merely depict example devices and although the present description uses these embodiments for description, other embodiments of apparatus can be easily made by one of skill in the art by modifications of the descriptions herein.

One or more small molecule that can be removed or extracted by a device, an apparatus, or a system of the disclosure, can be or can comprises a dye, a derivative of a dye, biotin, a biotin derivative, a crosslinker, a reducing agent, a label, a nanoparticle, a radioactive ligand, a mass tag, an unreacted molecule and combinations, intermediates and derivatives thereof.

Small molecules that can be removed by a device/apparatus or system if the disclosure have a molecular weight range of <2000 Da. This includes molecular weight ranges of from about 100-200 Da, 200-300 Da, 300-400 Da, 400-500 Da, 500-600 Da, 600-700 Da, 700-800 Da, 800-900 Da, 900-1000 Da, 1000-1100 Da, 1100-1200 Da, 1200-1300 Da, 1300-1400 Da, 1400-1500 Da, 1500-1600 Da, 1600-1700 Da, 1700-1800 Da, 1800-1900 Da, 1900-<2000 Da. In some embodiments, small molecules that can be removed by a device/apparatus or system if the disclosure have a molecular weight range of less than or equal to 50 Da, 100 Da, 150 Da, 200 Da, 250 Da, 300 Da, 350 Da, 400 Da, 450 Da, 500 Da, 550 Da, 600 Da, 650 Da, 700 Da, 750 Da, 800 Da, 850 Da, 900 Da, 950 Da, 1000 Da, 1050 Da, 1100 Da, 1150 Da, 1200 Da, 1250 Da, 1300 Da, 1350 Da, 1400 Da, 1450 Da, 1500 Da, 1550 Da, 1600 Da, 1650 Da, 1700 Da, 1750 Da, 1800 Da, 1850 Da, 1900 Da, 1950 Da, 1975 Da to about <2000 Da.

Systems, apparatus and devices of the disclosure, in embodiments, comprise a container comprising one or more compositions of the disclosure as set forth in detail in sections above and below.

One or more advantages of the systems, apparatus and devices of the disclosure include one or more of the following: economical, simple and easy to use, provision of faster time to results, adaptable be a single use disposable unit, usable for high throughput sample preparation in multi-well container formats, adaptable be subject to automated and robotic sample preparation systems. Reducing the quantity of small molecules from samples using the apparatus, devices and systems provided here provides quick and superior quality of biomolecules and their derivatives that can be used in downstream applications.

System

In some embodiments, the present disclosure provides a system for removing one or more small molecules from a sample comprising: a) a container comprising: a size exclusion support and at least one moiety that can associate with the one or more small molecules; and b) a receptacle located below the container. In some embodiments, a system further comprises a means to subject the container and receptacle to a gravity flow, a centrifugal force, a positive pressure, a negative pressure, vacuum and combinations thereof.

In some embodiments, a system of the disclosure can comprise devices 100 or 100" depicted above which may be formed to be accommodate into a centrifuge tube or any other comparable rotary instrument. In some embodiments, a system of the disclosure can comprise devices 100 or 100" depicted above which may be formed to be subject to a negative pressure (such as a vacuum) or a positive pressure (such as a syringe, a pipette).

A system of the disclosure (not depicted) may be fully automated or may be a manually operated system. In some embodiments, a system may be operated in part manually and in-part by automation.

A system can also comprise a computer system comprising a CPU, hardware elements and/or software elements may reside physically within or externally and may be operably linked to hardware/software elements. Computer system may be operable to control various components of device 100 or 100" such as, a control robot to retrieve eluate and analyze eluate.

A system of the disclosure may also optionally comprise one or more devices operable to further process the eluted biomolecules, such as but not limited to, processing eluted derivatized proteins such as conjugated antibodies or tagged proteins for fluorescent detection or immunoassays. In some embodiments, a system may comprise an imager or a protein or a nucleic acid detector or sequencer.

Computer system may be operable to control one or more components of a system of the disclosure. In some embodiments, as described above, a computer system and/or components thereof may reside physically within device 100 or 100" or may reside externally. Computer system may comprise a central processing unit, hardware and software elements operable to control and direct any automated steps of sample processing (by device 100 or 100" and other components of the system) and/or data processing of data acquired by processing samples and/or downstream data processing of data. Accordingly, a computer system used herein may comprise a data analysis and control system, a data transfer system such as a read-write CD ROM Drive or DVD drive, at least one USB port, and/or at least one Ethernet port. In some embodiments, a computer system may include pre-loaded software and/or Application Specific Integrated Circuits (ASICS) that may enable the control of device 100, 100" and/or other components the system, including multiple components of system, control of the processing and analysis, and/or control of displaying and/or exporting the results.

A system may also comprise additional devices or components, such as but not limited to, a power supply, a display unit such as a monitor operable to view sample processing and/or to monitor extraction of biomolecules from samples; spectrophotometers; devices to measure nucleic acid extraction; devices to further process extracted biomolecules for further analysis; printers and the like. A system of the disclosure may be configured to fit on a laboratory bench top.

Methods

In some embodiments, the present disclosure describes a method for separating a biomolecule from one or more small molecules comprising: a) applying a sample to a container comprising a size exclusion support and at least one moiety that can bind to at least one small molecule; and b) subjecting the container to a gravity flow, a centrifugal force, a positive pressure, a negative pressure, a vacuum or a combination thereof, wherein the biomolecule in the sample is excluded through the size exclusion support and is collected as a flow through, and wherein the at least one small molecule associates with the at least one moiety and is thereby separated from the sample.

in some embodiments of a method of the disclosure, separation of an at least one small molecule from the remainder of the sample is carried out in one step. In some embodiments of a method of the disclosure, flow through is collected in a receptacle located below the container. In some embodiments, small molecules may constitute an impurity or a contaminant to the sample.

A variety of samples that may be tested by methods of the disclosure may be any type of biological or clinical samples that may have biomolecules or derivatives thereof from which small molecules have to be separated or removed. Some exemplary non-limiting samples include samples having a protein dye conjugate, a biotinylated protein sample, proteins with a reducing agent such as DTT or TCEP crosslinked proteins and protein samples with crosslinkers. Dyes that are suitable for use are known to those skilled in the art and include, but are not limited to pyrene, coumarin, cyanine, benzofuran, a quinoline, a quinazolinone, an indole, a benzazole, a borapolyazaindacene and xanthenes including fluorescein, rhodamine and rhodol as well as other dyes described in RICHARD P. HAUGLAND, MOLECULAR PROBES HANDBOOK OF FLUORESCENT PROBES AND RESEARCH CHEMICALS ($11^{th}$ edition, January 2010), which is herein incorporated by reference in its entirety.

Methods of the disclosure may advantageously reduce the time required for processing a sample for reducing the quantity of small molecules from it.

Kits

The present disclosure also describes kits for implementing the methods discussed herein and/or kits that contain compositions and/or kits that contain apparatus/devices discussed herein.

In some embodiments, the present disclosure describes a kit for separating a biomolecule from one or more small molecules comprising: a device comprising: a) a container comprising at least one size exclusion resin and at least one moiety that can associate with the at least one small molecule and capture said small molecule; and b) a receptacle located below the container, wherein the device is operably configured to be subject to a gravity flow, a centrifugal force, a positive pressure, a negative pressure, vacuum and combinations thereof.

In some embodiments, a kit of the disclosure comprises at least two or more moieties that can associate with the one or more small molecules.

In some embodiments of a kit of the disclosure the device is a spin column, a multi-well filter plate, or a multi-well plate. A kit can further comprise one or more buffers packaged in one or more separate containers or included in the first container.

A kit of the disclosure may also comprise one or more reagents such as one or more wash buffers, elution buffers, filter membranes and/or additional spin columns or multi-well plates.

Reagents and components of kits may be comprised in one or more suitable container means. A container means may generally comprise at least one vial, test tube, flask, bottle, syringe or other container means, into which a component may be placed, and preferably, suitably aliquoted. Where there is more than one component in a kit they may be packaged together if suitable or the kit will generally contain a second, third or other additional container into which the additional components may be separately placed. However, in some embodiments, certain combinations of components may be packaged together comprised in one container means. A kit can also include a means for containing any reagent containers in close confinement for commercial sale. Such containers may include injection or blow-molded plastic containers into which the desired vials are retained.

In some embodiments, a device of a kit of the disclosure may be pre-filled with one or more of the reagents to process a sample and may be suitably aliquoted into appropriate chambers. A kit or containers thereof may have a seal to keep the internal compartments and any contents therein sterile and spill proof.

Some components of a kit are provided in one and/or more liquid solutions. Liquid solution may be non-aqueous solution, an aqueous solution, and may be a sterile solution. Components of the kit may also be provided as dried powder(s). When reagents and/or components are provided as a dry powder, the powder can be reconstituted by the addition of a suitable solvent. It is envisioned that a suitable solvent may also be provided in another container means. Kits may also comprise a container means for containing a sterile, pharmaceutically acceptable buffer and/or other diluent.

A kit of the disclosure may also include instructions for employing the kit components and may also have instructions for the use of any other reagent not included in the kit. Instructions can include variations that can be implemented.

EXAMPLES

Aspects of the present teachings can be further understood in light of the following examples, which should not be construed as limiting the scope of the present teachings in any way.

Example 1. Preparation & Testing of Compositions

Compositions for separating or extracting one or more small molecules from a sample comprising at least one size exclusion support and at least one moiety that can associate with the one or more small molecules were prepared and tested.

In some embodiments, exemplary size exclusion supports were modified with moieties comprising functional groups that can associate with small molecules by either charge interaction, hydrophobic interaction or any other interaction(s) to associate with and thereby remove these small molecules from a sample while allowing larger biomolecules in the sample to be excluded and collected.

In the present and following Examples, compositions for removal of four types of exemplary small molecules including dyes (in the molecular weight range of from about 700 Da-1100 Da), biotin and its derivatives (in the molecular weight range molecular weight range of from about 300 Da-1000 Da), reducing agents (in the molecular weight range of from about 150 Da-300 Da) and crosslinkers (in the molecular weight range of from about 300-600 Da) were prepared and tested for their ability to remove small molecules. While these exemplary small molecules and the listed molecular weight ranges were used in the experimental demonstration, one of skill in the art will realize that the present embodiments are not limited to either these small molecules or molecular weight ranges and the teachings herein enable one of skill in the art to make and use compositions and devices for removal of a variety of small molecule types and molecular weight ranges.

The following moieties were variously immobilized on a size exclusion support resin: 1. Dextrans of molecular weights ranging from 6 kDa to 2800 kDa); 2. Polyethyleneimine (PEI) (Linear and Branched); and 3. Diethylenediamine (DEA).

Example 1A: Preparation and Testing of Chemistry 1

Chemistry 1: Immobilizing a size exclusion support with a branched polyethyleneimine moiety: Two examples of size exclusion supports, comprising hydroxyethylcellulose resins having a 7 K and a 40K size exclusion range, e.g., Zeba 40 K Spin Desalting Columns, and Zeba 7 K Spin Desalting columns, from Thermo Scientific, were modified as described below. Vicinal diols, located on these size exclusion support columns, were periodate oxidized to generate aldehyde groups. Polyethyleneimine and diethylenediamine having primary amines were reacted with the generated aldehydes using Schiff base chemistry. Polyethyleneimine and diethylenediamine were prepared in PBS, the pH is adjusted to a range of 8.0-8.5, and reacted with the oxidized Zeba columns. These compositions are referred to later as Zeba 7K-PEI (PolyEthyleneImine) and Zeba40 K-PEI (PolyEthyleneImine).

Identical chemical modifications were also performed on an agarose resin that did not have any size exclusion properties (Sepharose Fast flow 4 (FF4) resin from GE). Vicinal diols located on the agarose resin, were periodate oxidized to generate aldehyde groups. Polyethyleneimine and diethylenediamine having primary amines were reacted with the generated aldehydes using Schiff base chemistry. Polyethylene imine and diethylenediamine were prepared in PBS, the pH was adjusted to a range of 8.0-8.5, and reacted with the oxidized agarose resins. This formed Agarose-PEI (PolyEthyleneImine) described in experiments later.

The following experimental steps were performed with the chemically modified size exclusion support (e.g., example Zeba columns described above) and non-size exclusion supports (e.g., example Sepharose resins described above): 1. 0.5 mL bed volume of the chemically modified supports were added to a spin column each. 2. The spin columns containing the various chemically modified supports were spun at 1000×g, for 2 minutes to remove storage solution. 3. Samples comprising a) an antibody conjugated dye was added at 100 µL onto the chemically modified supports in the spin column. The columns were spun at 1000×g, for 2 minutes and the flow-through was collected.

Figure 5:
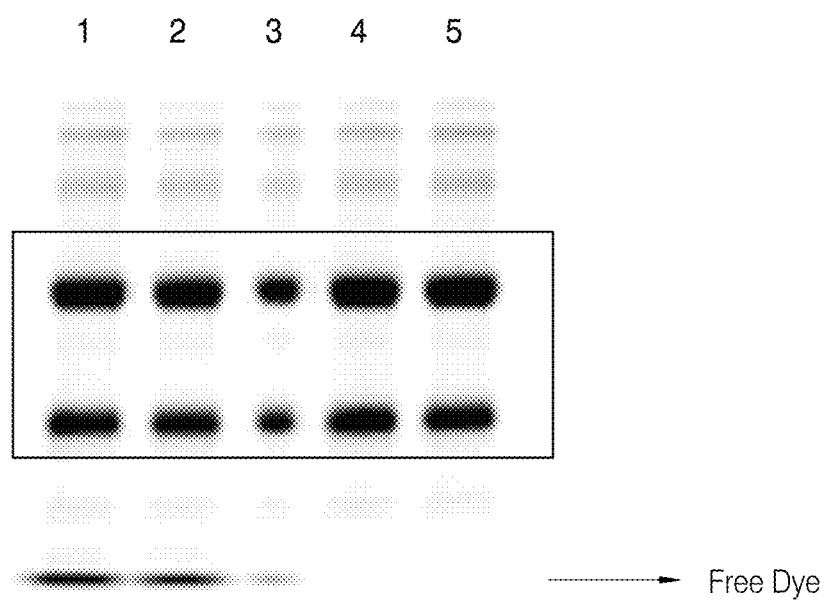
FIG. 5 depicts removal of an exemplary small molecule, a free dye, using a composition, device, a kit and method, according to one embodiment of the disclosure.

The results of these experiments are depicted in FIG. 5 which shows removal of an exemplary small molecule (a free dye), using two exemplary compositions in devices of the disclosure using methods, according to one embodiment of the disclosure. A small molecule, embodied herein by a free dye (DyLight™ 650) was removed using different example compositions of the disclosure including size exclusion supports (at least two types of hydroxyethylcellulose supports having a 7 K and a 40K size exclusion range were each individually associated with a combination of moieties comprising a polyethyleneimine (as an exemplary first moiety) and a diethylenediamine (as an exemplary second moiety). Comparative efficiency of a simple Detergent Removal Resin was also tested under similar conditions.

Various lanes of the gel in FIG. 5 were loaded as follows: Lane 1—GAM (GoatAntiMouse) DyLight™ 650 conjugate (uncleaned—control); Lane 2—Detergent Removal Resin (Pierce™ Detergent Removal Resin, HiPPR™ Detergent Removal Spin Column Kit); Lane 3—Agarose-PEI (Poly-EthyleneImine); Lane 4—Zeba 7 K-PEI (PolyEthyleneImine); Lane 5—Zeba40 K-PEI (PolyEthyleneImine).

The two bands within the box in FIG. 5 shows recovered protein, i.e., the GoatAntiMouse DyLight™ 650 conjugate protein (GAM DyLight™ 650 conjugate) from each lane and the bottom band indicates free dye DyLight™ 650 that remained in the sample. Free or unreacted dye 650 was retained in the column and eluted out later following protein recovery. Lane 1 is the uncleaned GAM 650 conjugate. The term "Uncleaned" is used here to describe the GAM DyLight™ 650 conjugate that has not been passed through any resin/support. "Uncleaned" is the control that was run on a gel to demonstrate how a sample with the free dye "not" removed by the compositions, apparatus and methods of the disclosure would be visible on a gel. Lane 2 shows the GAM 650 conjugate protein that is passed through an exemplary simple detergent removal resin (Pierce™ Detergent Removal Resin, HiPPR™ Detergent Removal Spin Column Kit) to test if this type of resin can remove small molecules (such as free dye). The presence of the bottom band indicates that the free dye is not completely or efficiently removed by this resin as compared to other lanes (especially compared to Lanes 4 and 5). Lane 3 shows the GAM 650 conjugate protein is separated from free dye to some extent by PEI immobilized on Agarose resin. However, Lane 3 shows comparatively poor protein recovery and poor removal of free dye as compared to Lanes 4 and 5. Lanes 4 and Lane 5 show comparatively best protein recovery as compared to Lanes 1, 2 and 3. The bottom band which indicates free dye is completely absent in Lane 4 and Lane 5, indicating free dye is efficiently removed by PEI modified size exclusion resins (7K and 40 K Zeba resins). However, recovery of the GAM 650 conjugate by the non-size exclusion agarose resin is poor as compared with recovery by size exclusion resin such as the 7 K and 40 K Zeba resins in lanes 4 and 5. Thus, Lane 4 and Lane 5, that used compositions, devices and methods of the present disclosure, show optimal removal of small molecules shown here by the absence of free dye and efficient conjugate-protein (large biomolecule) recovery as compared to other lanes. Quantitative data for other dyes in shown in Examples below.

Thus, at least two compositions of the disclosure were analyzed in this experiment: 1. hydroxyethylcellulose size exclusion support having a 7 K size associated with a combination of moieties comprising a polyethyleneimine (as an exemplary first moiety) and a diethylenediamine (as an exemplary second moiety); 2) hydroxyethylcellulose size exclusion support having a 40 K size associated with a combination of moieties comprising a polyethyleneimine (as an exemplary first moiety) and a diethylenediamine (as an exemplary second moiety); and the two compositions of the disclosure were compared and contrasted for performance with a non-size exclusion support chemically modified similar to the compositions of the present disclosure (i.e., compared with an agarose support associated with a combination of moieties comprising a polyethyleneimine (as an exemplary first moiety) and a diethylenediamine (as an exemplary second moiety), as well as to a Detergent Removal Resin and to the "uncleaned" control. As shown in the experiments and results above (and in FIG. 5), neither the modified non-size exclusion support, nor the Detergent Removal Resins were able to remove small molecules as efficiently as compositions of the disclosure comprising modified size-exclusion supports.

Example 1B: Preparation of Chemistry 2

Chemistry 2: Immobilizing a size exclusion support with a dextran moiety: In this example, a 7 K and a 40 K hydroxyethyl cellulose resins (Zeba™ Spin Desalting Columns, 40 K, and Zeba™ Spin Desalting columns, 7 K), were associated with a dextran moiety to form additional compositions of the disclosure. Different MW Dextrans (in the ranges of 6 K Dalton to 2.8 Million Dalton) were immobilized onto 7 K and 40 K resins.

First, dextran of molecular weight range 1,500,000 Da-2,800,000 Da was immobilized onto the resins as described below. Vicinal diols on the hydroxycellulose size exclusion supports were periodate oxidized to generate aldehyde groups. Ethylene Diamine (EDA) or 1,5 Diaminopentane (PDA) were reacted to the generated aldehydes using Schiff base chemistry. This generated a terminal amine group on both the 7K and 40 K size exclusion supports. Dextran solution was then periodate oxidized using Sodium metaperiodate to generate aldehyde groups. The aldehyde group generated on Dextran was then reacted with terminal amine to generate Dextran immobilized on the 7K and 40 K resins.

Similar compositions and chemical modifications were also prepared on a non-size exclusion support of agarose for comparative analysis. As noted in sections above agarose does not have size exclusion properties. Chemical reactions are described below:

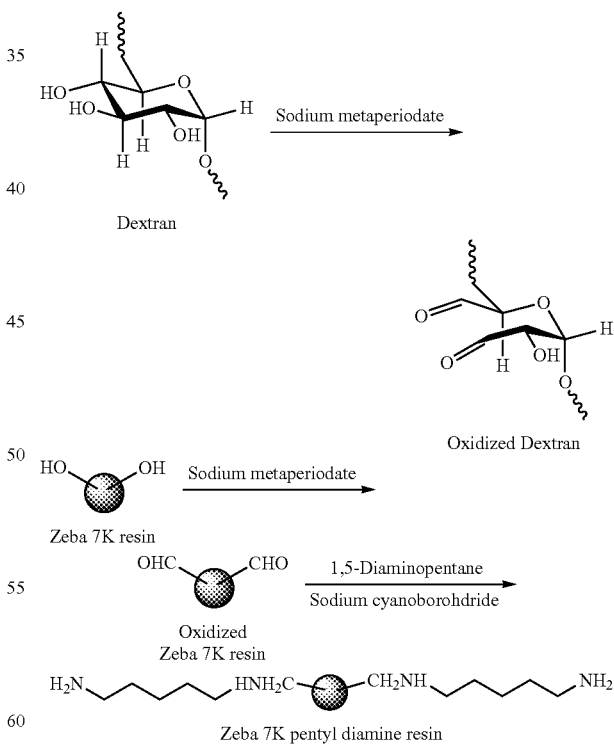

Example 1C: Preparation of Chemistry 3

Chemistry 3: Immobilizing a size exclusion support with a branched polyethylene glycol amine moiety: Compositions comprising size exclusion supports (Zeba, 7K and 40 K, Thermo Scientific) with Poly (ethylene glycol) bis (amine) were prepared as follows: Moieties of different MW Poly (ethylene glycol) bis (amine) (2 K Dalton to 20 K Dalton) were immobilized on size exclusion supports (7 K and 40 K resins) using the Schiff base chemistry as explained in sections above.

Similar chemical modifications were also done on non-size exclusion agarose supports (Agarose, GE Healthcare) for comparative analysis. The chemical reactions are depicted below:

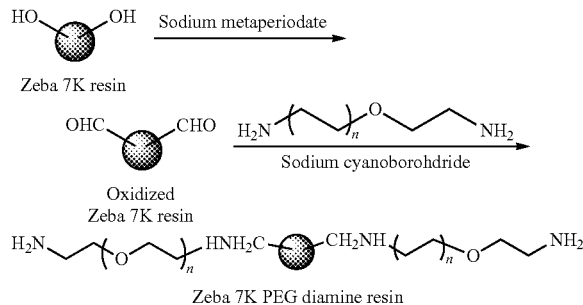

Example 1D: Testing of Chemistry 2 and 3: Removal of Free Dye Small Molecules with Chemistry 2 and 3 in Spin Column Device Compositions of Chemistry 2 and 3 described above were tested for small molecule removal.

All experiments to remove small molecules (in this Example and other Examples, unless specifically mentioned as using other methods/devices) were done using a 0.5 mL resin bed volume (of various chemistries as described variously above) assembled into in a 0.8 mL spin column to create a non-limiting embodiment apparatus of the disclosure. The spin-column was spun at 1000×g for 2 minutes to remove the storage solution. The spin-column was then placed in a clean 2 mL centrifuge tube. Sample volume of 100 µL was added to the center of the resin and the column was spun at 1000×g for 2 minutes and the flow-through was collected in the 2 mL tube. Results of these Experiments are depicted in FIG. 6.

Figure 6:
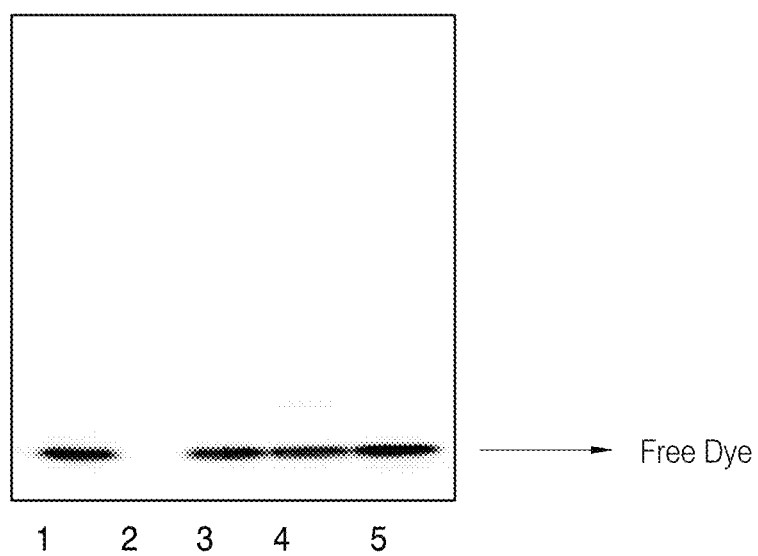
FIG. 6 depicts removal of an exemplary small molecule, a free dye, using a composition, device, a kit and method, according to one embodiment of the disclosure.

FIG. 6 depicts removal of another exemplary small molecule a free dye, DyLight™ 550 NHS Ester, using different supports of the disclosure including 20 k PEG Diamine Zeba 7k; Dextran-PDA Zeba 7k (where PDA refers to 1,5 Diaminopentane); and controls including: Zeba 7k (unmodified) and Starting Sample (control) and comparing to another chemistry including: Zeba 7k and Dextran Resin (crosslinked together). This experiment was done without protein to demonstrate the capacity of the compositions of the present disclosure to associate with a small molecule such as a free dye (e.g. DyLight™) in comparison to unmodified size exclusion resins (such as, the unmodified Zeba 7K resin in lane).

DyLight™ 550 NETS-Ester was prepared at 1.3 mg/mL in Borate buffer (this 1.3 mg/mL is equivalent to taking 20 molar excess of the dye to 10 mgs of GAM protein). 500 µl of different supports of the disclosure and controls were assembled in 0.8 ml spin columns. 100 µL of the 1.3 mg/mL of DyLight™ 550 NETS-Ester was added to the resins. The spin columns were spun in a centrifuge at 1000×g for 2 minutes. The flow-through was collected. 10 µL of the flow-through was added to 90 µL of sample buffer. 10 µL of this was then added per well on a 4-20% Tris Glycine SDS gel. The gel was run for 40 minutes and was then imaged using the iBright imager (Thermo Fisher Scientific). Lanes in the FIG. 6 corresponds to the following support compositions that were used for removing the free dye: Lane 1-20k PEG Diamine Zeba 7k; Lane 2—Dextran-PDA Zeba 7k; Lane 3—Zeba 7k (unmodified); Lane 4—Zeba 7k and Dextran Resin (crosslinked together); Lane 5—Starting sample or positive control (20 molar excess DyLight™ 550 NETS-Ester in borate buffer).

FIG. 6, Lane 1 depicts data for removal of a small molecule with a PEG Diamine immobilized on a 7 K Zeba resin. This chemistry was not successful in removing the free dye. Lane 2, depicts data of a Dextran-PDA immobilized on a 7K size exclusion support resin which removed 100% of the free dye. Lane 3 which is the unmodified 7 K Zeba resin (i.e., only a size exclusion resin, without any moiety added—no surface chemistries) was not successful in removal of free dye. Lane 4 corresponds to a resin prepared by another chemistry for comparison with the present composition chemistries. Lane 4 resin was prepared by crosslinking hydroxyethyl cellulose and Dextran using a crosslinker as opposed to immobilizing Dextran on Zeba resins. This crosslinking chemistry was not as effective as compared to Lane 2 chemistry wherein Dextran was immobilized onto the size-exclusion support by reductive amination method described above. As seen in Lane 2 the free dye is completely removed, depicted by the missing free-dye band while the free dye band is present in Lane 4 indicating that the free dye is not removed by crosslinked resin. Lane 5 shows the "uncleaned" sample passed as described in sections above. Here the DyLight™ 550 NETS-Ester at 1.3 mg/mL that was not passed over any resin. This 1.3 mg/mL solution was diluted at 1:10 in the sample buffer as described above and loaded onto the gel.

Example 1E: Testing of Chemistry 2 & 3: Removal of Reducing Agent Small Molecules Using Chemistry 2 & Chemistry 3

Figure 7:
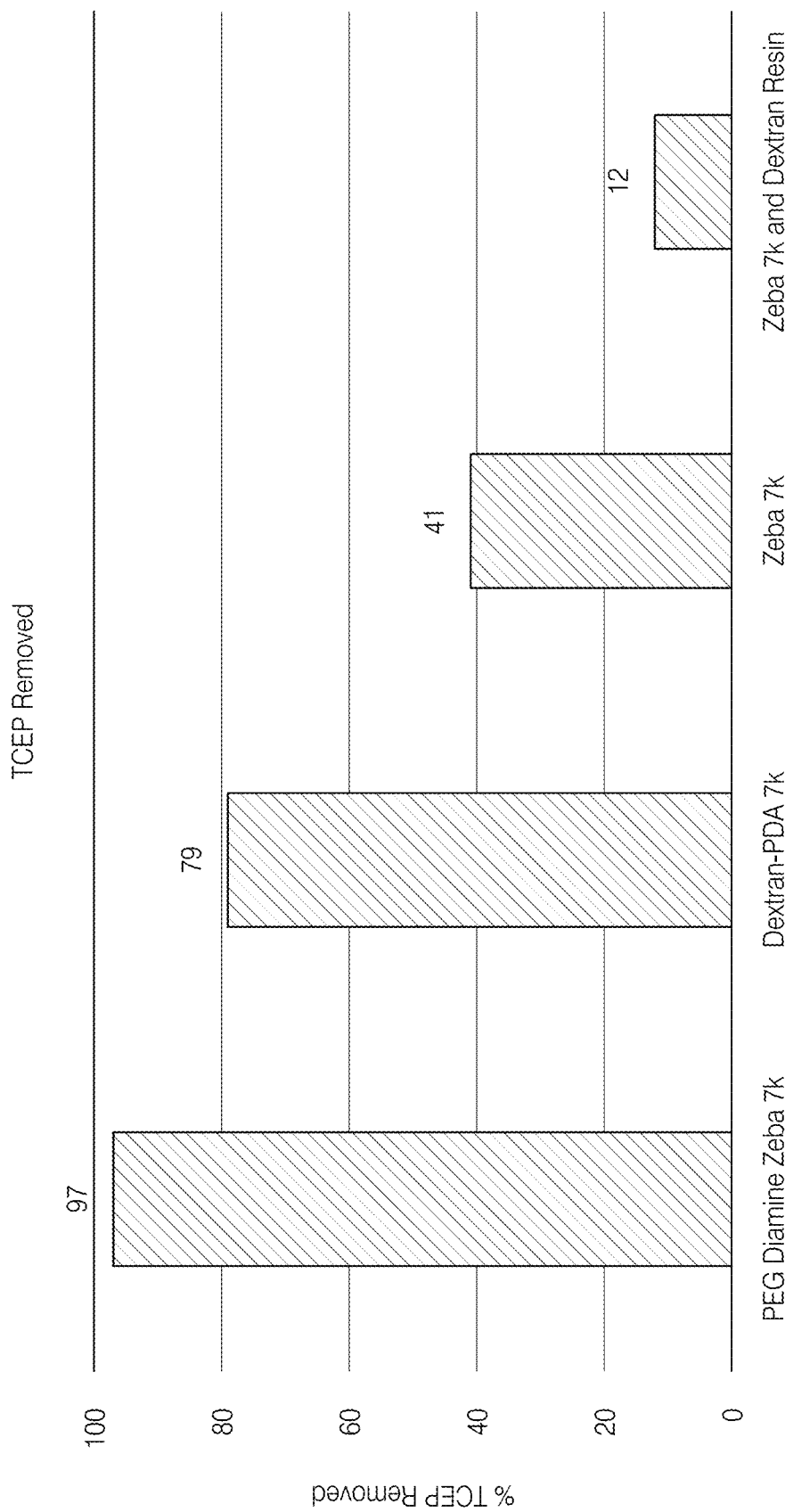
FIG. 7 depicts removal of an exemplary small molecule, a reducing agent, using a composition, device, a kit and method, according to one embodiment of the disclosure.

Another composition of the disclosure, was generated as described in Chemistry 3, comprising a single moiety PEG (Polythyleneglycol) Diamine immobilized on a size exclusion support (7 K Zeba, Thermo Scientific) and tested for its ability to remove small molecules that function as reducing agent as follows: 714 µl of 70% support resin slurry was pipetted into spin columns placed in a collection receptacle tube. The spin-column was spun at 1000×g for 2 minutes to remove the storage solution. The spin-column was then placed in a clean 2 mL centrifuge tube. Sample volume of 100 µL comprising a reducing agent Tris(2-carboxyethyl) phosphine (TCEP) at a concentration of 50 mM in PBS was added to the center of the spin column comprising the compositions as noted above and spun at 1000×g for 2 minutes and the flow-through was collected in the 2 mL tube. The TECP removal from the sample was tested by Ellmans Assay. This assay was done by adding the following in a 96 well plate: a) 250 µl Ellmans buffer; b) 10 µl Ellmans reagent (4 mg/ml); c) 50 µl sample (diluted 1:10) and then measuring quantity of TCEP by reading samples at 450 nm on a colorimeter (Multiskan, Thermo Scientific). The quantity of TCEP in a sample is proportional to the intensity of color indicated by a read at 450 nm. Accordingly, a higher reading at 450 nm corresponds to a larger quantity of TCEP present in the sample. Results of these Experiments are depicted in FIG. 7. Low values at 450 nm indicating efficient removal of TCEP.

FIG. 7. depicts removal of an exemplary small molecule, a reducing agent (TCEP), using compositions, devices and methods according to one embodiment of the disclosure and comparing these to controls including unmodified Zeba 7K. As shown in FIG. 7, the first bar corresponds to PEG Diamine immobilized on size exclusion support resin exemplified by 7K Zeba and shows removal of 97% of TCEP which was added at 50 mM to the resin. The second bar corresponds to a Dextran-PDA immobilized onto size exclusion support resin exemplified by 7K Zeba and shows removal of 80% of the TCEP. In contrast, the third bar of FIG. 7, shows the results of passing TCEP sample at 50 mM onto a size exclusion support resin that was not chemically modified, exemplified by an unmodified Zeba 7K resin, and shows removal of 41% of TCEP. The fourth bar shows the effect of another chemistry comprising a 7K Zeba resin crosslinked to Dextran and shows removal of only 12% TCEP. Thus, compositions of the present disclosure made according to Chemistry 2 and Chemistry 3, show significantly higher removal of the small molecule reducing agent TCEP as compared to other compositions.

Example 2: Blended Compositions and Removal of Small Molecules in Spin Columns and Multi-Well Formats From data obtained in experiments depicted in FIGS. 5, 6 and 7, the size exclusion support resin alone (i.e., 7K Zeba with no associated moiety or chemistry) is not capable of removing small molecules including for example dyes or reducing agents such as TCEP. Compositions of the disclosure comprising size exclusion resins and Dextran were able to remove both types of small molecules including dyes and reducing agents. For example, data in FIGS. 5 and 6 depict that compositions of the present disclosure comprising for example a Dextran immobilized on-to a size exclusion support (Zeba 7K and 40K in FIG. 5, and Zeba 7K in FIG. 6) removes free unreacted dyes (Dyes 650, NHS 550), and Dextran PDA in FIG. 7 removes reducing agent TCEP. However, some compositions of the present disclosure comprising for example a PEG Diamine moiety immobilized on a size exclusion support (Zeba 7K) allowed the removal significant amounts of small molecule reducing agent TCEP (see FIG. 7 and FIG. 13) as well as DTT (see FIG. 19) but were unable to remove small dye (see FIG. 6, Lane 1).

Hence, the present inventors created compositions comprising blends of various compositions described herein to generate compositions that can removes several types of small molecules. Some exemplary blend compositions of the disclosure are depicted in Table 1:

TABLE 1

| Different Blends | PEG Diamine- 7K | Dextran-7K |
| --- | --- | --- |
| Blend 1 | 1 | 3 |
| Blend 2 | 1 | 2 |
| Blend 3 | 1 | 1 |
| Blend 4 | 2 | 1 |
| Blend 5 | 3 | 1 |

The Blends 1-5 described in Table 1, comprising a composition of Dextran immobilized on size exclusion 7K resins and a composition of PEG Diamine immobilized on size exclusion 7K resins were prepared at various ratios of each composition as described in columns 2 and 3 of Table 1.

Blends of Table 1, made at 1:1 ratio, were tested for their ability to remove different classes of small molecules and were compared to similar tests performed on corresponding controls of unmodified size exclusion resins (7K Zeba resins) and controls of unclean conjugated protein.

The blended compositions were incorporated into spin columns of various sizes (0.8 mLs, 2 mLs, 5 mLs and 10 mLs) and also on 96-well filter plates to test the ability of the compositions in the devices of the disclosures. The spin columns or multi-well plates were spun in a centrifuge at 1000×g for 2 minutes to remove storage buffers. Appropriate volume of samples comprising small molecules were added. The columns or multi-well plates were spun again in centrifuge at 1000×g for 2 minutes and the eluate collected in the flow-through. Data is shown in FIGS. 8, 9 and 10 and corresponds to experiments performed in spin column formats.

For FIG. 8, a sample volume of 700 µL goat anti-mouse IgG conjugated with 10 molar excess DyLight™ 550 was applied to the center of a spin column with the compositions corresponding to each lane as noted below. Free dye removal was assessed in the flow-through by SDS-PAGE, imaging gel on iBright imager followed by quantification of dye removal by iBright analysis software. Modified 7k 1:1 blend samples (Lanes 1-2) had greater than 99% dye removal, unmodified 7k Zeba resin (Lane 3) had 20% dye removal as compared to "unclean" starting sample (Lane 4) having 10 mg/ml goat anti-mouse IgG with 10 molar excess DyLight™ 550 dye. Percentages of removal of small molecules are calculated in comparison to what is in the "unclean" control.

Figure 8:
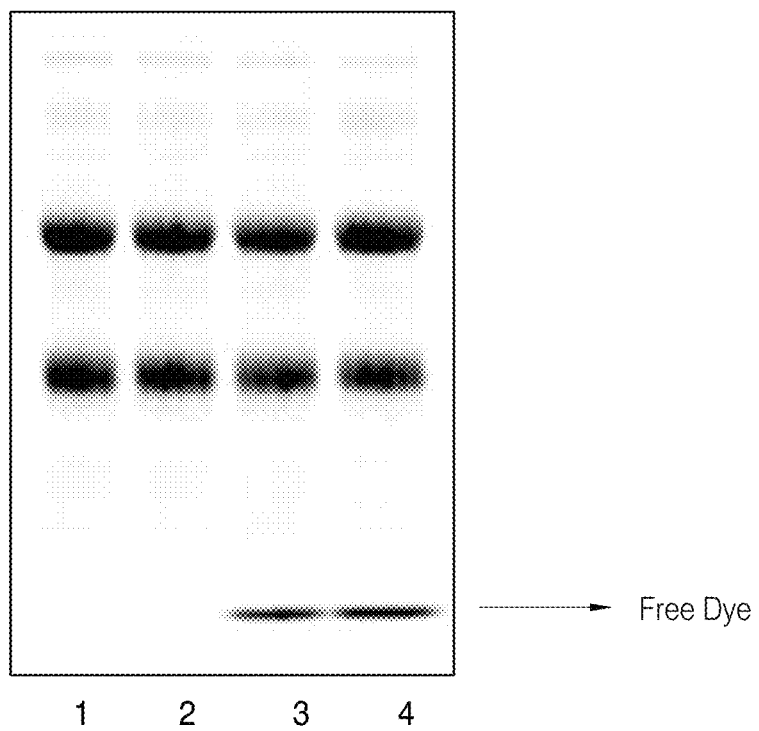
FIG. 8 depicts removal of exemplary small molecules, a free dye, using a blended composition, devices, kits and methods, according to one embodiment of the disclosure.

FIG. 8 depicts small molecule dye removal of DyLight™ 550 from a protein conjugate of DyLight™ 550 goat anti-mouse IgG, using 1:1 ratio of exemplary Blend compositions of Table 1. Lane 1 has data for dye removal using a 1:1 Dextran-PDA blend; Lane 2 has data for dye removal 1:1 Dextran-EDA (EthyleneDiAmine) blend; Lane 3 has data for dye removal using an unmodified 7K Zeba size exclusion resin; and Lane 4 has data for an "unclean" control of dye DyLight™ 550 goat anti-mouse IgG. FIG. 7 shows that the Blends of Lanes 1 and 2 are able to remove substantial quantities of free dye as compared to the control and Lane 3. This is depicted in FIG. 7 by near absence of Free Dye bands at the bottom of the gel.

Figure 9:
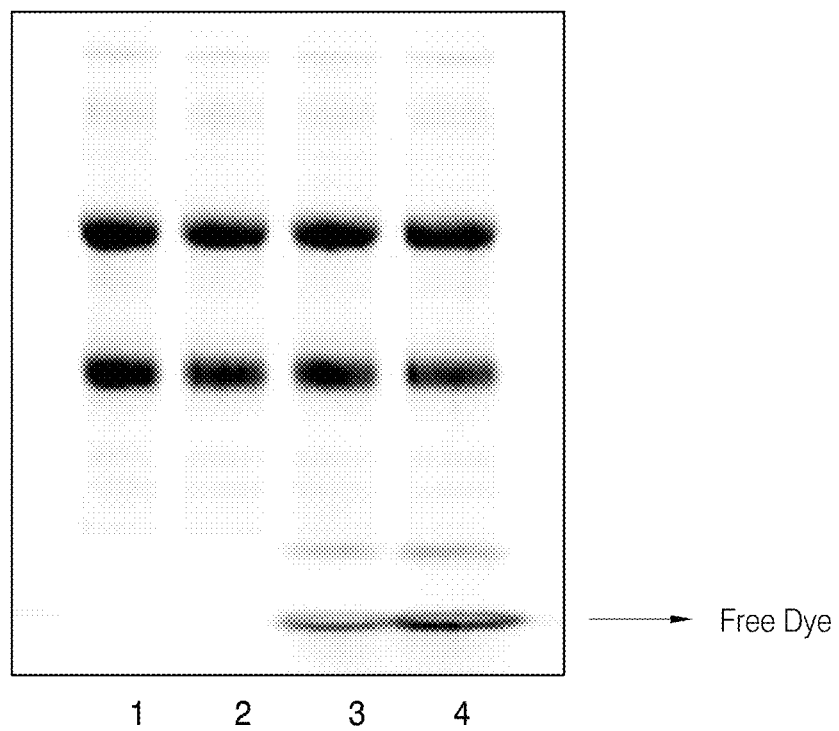
FIG. 9 depicts removal of exemplary small molecules, a free dye, using a blended composition, devices, kits and methods, according to one embodiment of the disclosure.
Figure 10:
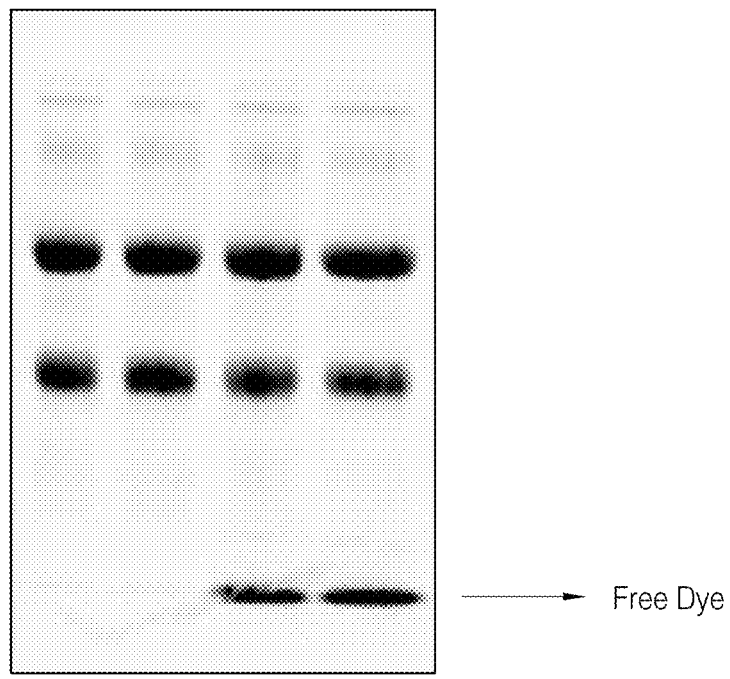
FIG. 10 depicts removal of exemplary small molecules, a free dye, using a blended composition, devices, kits and methods, according to one embodiment of the disclosure.

In FIG. 9, a sample volume of 2 mL goat anti-rabbit IgG conjugated with 10 molar excess Alexa Fluor™ 488 was applied to the center of spin columns comprising compositions corresponding to those described below for each lane. The columns were spun in a centrifuge at 1000×g for 2 minutes and flow-through was collected. Free dye removal in the flow through of each column was assessed by SDS-PAGE, imaging gel on iBright imager followed by quantification of dye removal by iBright analysis software. Modified 7k 1:1 blend samples (Lanes 1-2) had greater than 99% dye removal compared whereas unmodified 7k Zeba resin (Lane 3) had 49% dye removal as compared to "unclean" starting sample (Lane 4) consisting of 10 mg/ml goat anti-rabbit IgG with 10 molar excess Alexa Fluor™ 488 dye.

FIG. 9 depicts small molecule dye removal of Alexa Fluor™ 488 from a protein conjugate of Alexa Fluor™ 488 goat anti-rabbit IgG, using 1:1 ratio of exemplary Blend compositions of Table 1 wherein Lane 1 has data for dye removal using a 1:1 Dextran-PDA blend; Lane 2 has data for dye removal 1:1 Dextran-EDA blend; Lane 3 has data for dye removal using an unmodified 7K Zeba size exclusion resin; and Lane 4 has data for an "unclean" control of dye Alexa Fluor™ 488 goat anti-rabbit IgG. FIG. 9 shows that the Blends of Lanes 1 and 2 remove significant amount of free dye as compared to the Lane 4 control and Lane 3 unmodified resin. This is depicted by near absence of Free Dye bands at the bottom.

In FIG. 10, a sample volume of 4 mL goat anti-mouse IgG conjugated with 10 molar excess DyLight™ 650 was applied to the center of the spin column with the compositions corresponding to each lane as noted below. Free dye removal was assessed in the flow-through by SDS-PAGE, imaging gel on iBright imager followed by quantification of dye removal by iBright analysis software. Modified 7K 1:1 blend samples (Lanes 1-2) had greater than 99% dye removal, whereas unmodified 7K Zeba resin (Lane 3) had 22% dye removal as compared to "unclean" starting sample (Lane 4) that has 10 mg/ml goat anti-mouse IgG with 10 molar excess DyLight™ 550 dye.

FIG. 10 depicts small molecule dye removal of DyLight™ 650 from a protein conjugate of DyLight™ 650 goat anti-mouse IgG, using 1:1 ratio of exemplary Blend compositions of Table 1 wherein Lane 1 has data for dye removal using a 1:1 Dextran-PDA blend; Lane 2 has data for dye removal 1:1 Dextran-EDA blend; Lane 3 has data for dye removal using an unmodified 7K Zeba size exclusion resin; and Lane 4 has data for an "unclean" control of dye DyLight™ 650 goat anti-mouse IgG. FIG. 10 shows that the Blends of Lanes 1 and 2 remove significant amount of free dye as shown by near absence of Free Dye bands at the bottom.

In FIGS. 8, 9 and 10, the amount of removal of various dyes/small molecules is expressed as a % when compared to their respective amount in "unclean" samples (in Lane 4 of each of the gels).

Figure 12:
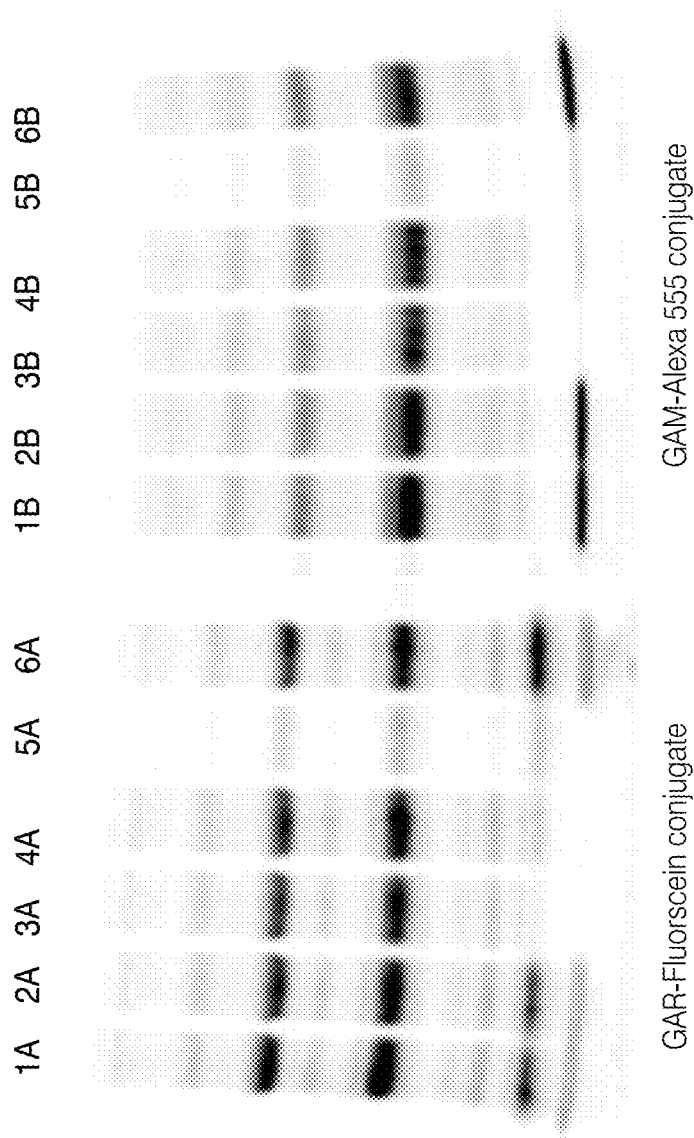
FIG. 12 depicts removal of exemplary small molecules, two exemplary free dyes, using a blended composition, devices, kits and methods, according to one embodiment of the disclosure.

Blends of Table 1, made at 1:1 ratio, was also tested for their ability to remove different classes of small molecules and were compared to similar tests performed on corresponding non-size exclusion Agarose-Dextran and Agarose-PEG Diamine resins also blended at a ratio of 1:1 (referred to herein as FF4 blends in FIGS. 12 (Lane 5 A and 5 B), 13, 14, 15 and 16). These compositions at 0.5 ml bed volume were incorporated into spin columns of 08.ml column capacity, to compare them with the compositions and devices of the present disclosures. The spin columns were initially spun in a centrifuge at 1000×g for 2 minutes to remove storage buffers. Appropriate volume of samples comprising small molecules were added. The columns were spun again in centrifuge at 1000×g for 2 minutes and the eluate collected in the flow-through. Data is shown for example in FIGS. 12 (Lane 5 A and 5 B), and in FIGS. 13, 14, 15 and 16.

Example 3: Removal of Free Dye Small Molecules with Blended Compositions in Multi-Well Filter Plate Device Blended compositions described above were tested for small molecule removal using a multi-well filter plate device format.

All experiments to remove small molecules were done using a 0.5 mL resin bed of modified 7k 1:1 resin blend (of different chemistries as described variously above) and assembled in microwell/multiwell plates to create a non-limiting embodiment apparatus of the disclosure. For these experiments multiwell plates consisting of 96-wells, containing the described chemistries, were placed on a top of a 96-well wash plate. Next, this assembly was placed into a 96-well plate-carrier rotor and centrifuged at 1000×g for 2 minutes to remove the storage buffer. The plate assembly was removed from the centrifuge and the wash plate was discarded. The 96-well plate was then placed on top of a 96-well collection plate. Sample (20 μl, 50 μl and 100 μl) was applied to the center of the resin bed of each well. The plate assembly was centrifuged at 1000×g for 2 minutes to collect the sample. Antibody conjugate was collected with free dye removed. Free dye removal was assessed by SDS-PAGE, imaging gel on iBright imager followed by quantification of dye removal by iBright analysis software. Results of multiwell plates are depicted in FIG. 11.

Figure 11:
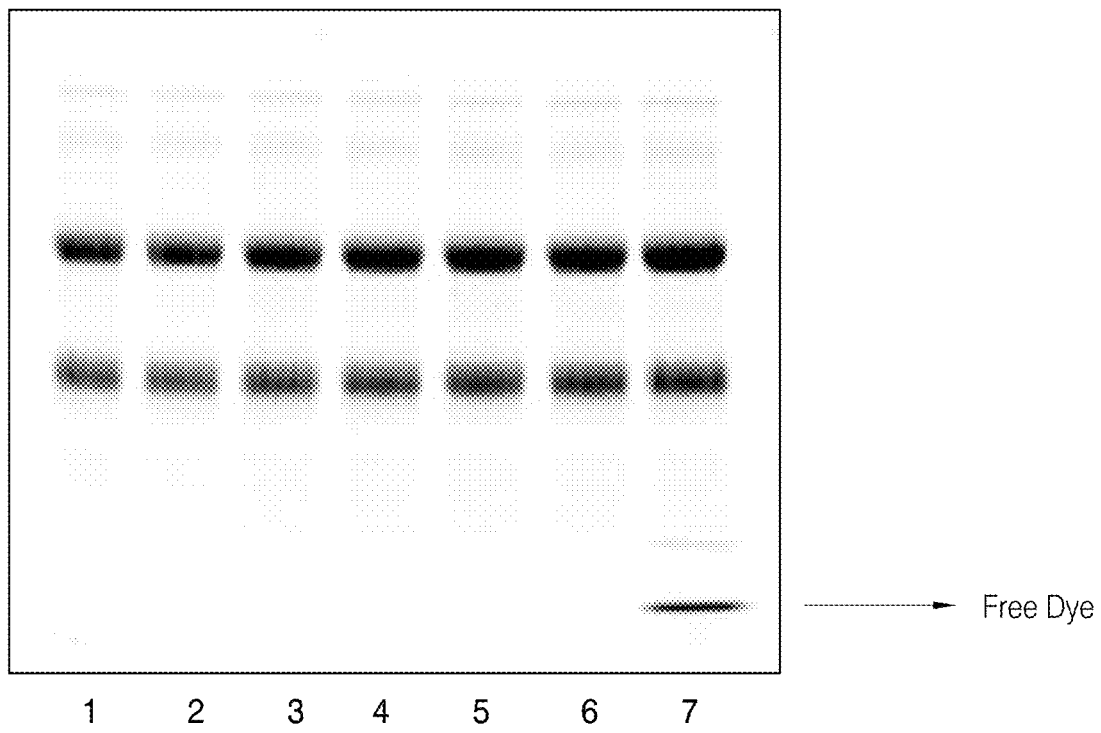
FIG. 11 depicts removal of exemplary small molecules, a free dye, using a blended composition, a device, a kit and methods, according to one embodiment of the disclosure.

In FIG. 11, Lanes 1 and 2 correspond to 20 μl goat anti-rabbit IgG Alexa Fluor™ 647 conjugate applied to modified 7K 1:1 resin blend. Lanes 3 and 4 corresponds to 50 μl goat anti-rabbit IgG Alexa Fluor™ 647 conjugate applied to modified 7K 1:1 resin blend. Lanes 5 and 6 corresponds to 100 μl goat anti-rabbit IgG Alexa Fluor™ 647 conjugate applied to modified 7K 1:1 resin blend. Lane 7 corresponds to "unclean" samples of goat anti-rabbit IgG Alexa Fluor™ 647 conjugate that were not applied to any resin blend. All samples (lanes 1-6) show greater than 99% dye removal compared to "unclean" sample (lane 7) consisting of 10 mg/ml goat anti-rabbit IgG conjugated with 10 molar excess Alexa Fluor™ 647 dye. Lanes 1-2 flow-through from 20 μl samples applied to resin bed, lanes 3 and 4 flow-through from 50 μl samples applied to resin bed, lanes 5 and 6 flow-through from 100 μl samples, lane 7.

Example 4: Blended Compositions for Removal of Small Molecule Free Dyes

FIG. 12 depicts data of removal of exemplary small molecules, two exemplary free dyes, Fluorescein and Alexa Fluor™ 555, using blended compositions, devices, kits and methods, according to one embodiment of the disclosure.

FIG. 12 Experimental steps were as follows: Dye Removal Protocol: 1. Pipette 1 ml 50% Resin slurry into spin column placed in a collection tube; 2. Spin out liquid for 2 min at 1000×g; 3. Replace collection tube and add antibody samples (GAR Fluorescein conjugate and GAM Alexa 555 conjugate) into each spin column for each of samples; 4. Remove free dye from samples by centrifuging for 2 min at 1000×g.

Assess Dye Removal in Gel: 1. Prepare samples for running on gel by adding following to microcentrifuge tube: a) 20 μl of 2× loading buffer containing 50 mM DTT & b) 20 μl flow through from antibody cleanup from step 4. Above; 2. Heat samples at 95° C. for 8 min; 3. Cool samples on ice; 4. Load 10 μl of each sample into separate wells on gel; 5. Run gel for 32 min. at 225V; 6. Remove gel and rinse; 7. Image on iBright imager at appropriate fluorescence.

In FIG. 12, Lanes 1-6 (A or B) comprise the following blended compositions including: Lanes 1A and 1B comprise 40 K Zeba which is an unmodified size exclusion resin with molecular weight cut off of 40 K; Lanes 2A and 2B comprise 7K Zeba which is an unmodified size exclusion support resin with a molecular weight cut off of 7K; Lanes 3A and 3B comprise a 40K Blend which is a blend of a 1:1 ration of a 40K resin modified with Dextran and a 40K resin modified with a PEG Diamine; Lanes 4A and 4B comprise a 7K Blend which is a 1:1 ratio blend of a 7K resin modified with Dextran and a 7K resin modified with a PEG Diamine; Lanes 5A and 5B comprise FF4 which is Fast Flow 4 Agarose (from GE), a non-size exclusion resin blended in a 1:1 ratio comprising FF4 modified with Dextran and FF4 modified with a PEG Diamine; Lanes 6A and 6B comprise "Unclean" or unprocessed sample (for e.g. a Dye conjugate that is not passed through any resin. The A lanes (lanes 1A-6A) comprise GAR or Goat Anti Rabbit IgG-Fluorescein conjugate protein and the B lanes (lanes 1B-6B) comprise GAM or Goat Anti Mouse IgG-Alexa Fluor™ 555-conjugate protein.

Lane 6A and 6B depict the "unclean" sample and show two bands at the top which correspond to reduced Antibody bands and free dyes band at the bottom of the gel (free dye band in Lane 6A corresponds to free Fluorescein dye and in Lane 6B corresponds to free Alexa Fluor™ 555 dye). In the processed samples (Lanes 1A through 5A and Lanes 1B through 5B), the presence of bottom dye band is indicative of incomplete or unsuccessful removal of free dye (Fluorescein and Alexa Fluor™ 555) as indicated in Lanes 1A, 1B, and 2A and 2B. The presence of free Fluorescein band at the bottom of Lane 1A and 2A indicates poor or no removal of free Fluorescein by unmodified 40 K and unmodified 7K Zeba resins respectively. Similarly, the presence of free Alexa Fluor™ 555 band at bottom of Lane 1B and 2B indicates poor removal of free Alexa Fluor™ 555 dye by unmodified 40K and unmodified 7K Zeba resins respectively. Lanes 3A and 4A which are the 40K Blends (1:1) and 7K Blends (1:1) indicate no free Fluorescein band or a near absence at the bottom indicates excellent free dye removal property of these two blends. Similarly, Lanes 3B and 4B which are the 40K Blends (1:1) and 7K Blends (1:1) indicate no free Alexa Fluor™ 555 band or a near absence at the bottom indicating excellent free dye removal property of these two resins. Lanes 5A and 5B indicates complete loss of GAR antibody conjugated Fluorescein (5A) and GAM antibody conjugated Alexa Fluor™ 555 (5B) as evidenced by the lack of reduced antibody bands for 5A and 5B on the gel. In addition to removal of free dye, excellent protein recovery of antibody conjugated fluorescein and antibody conjugated Alexa Fluor™ 555 in lanes 3A, 4A and 3B and 4B. The bands from these lanes were quantified using iBright Analysis software and % dye removal and % antibody dye conjugate recovery were plotted for the different resins (see data in FIGS. 15 and 16).

Example 5: Blended Compositions for Removal of Small Molecule Reducing Agents

Figure 13:
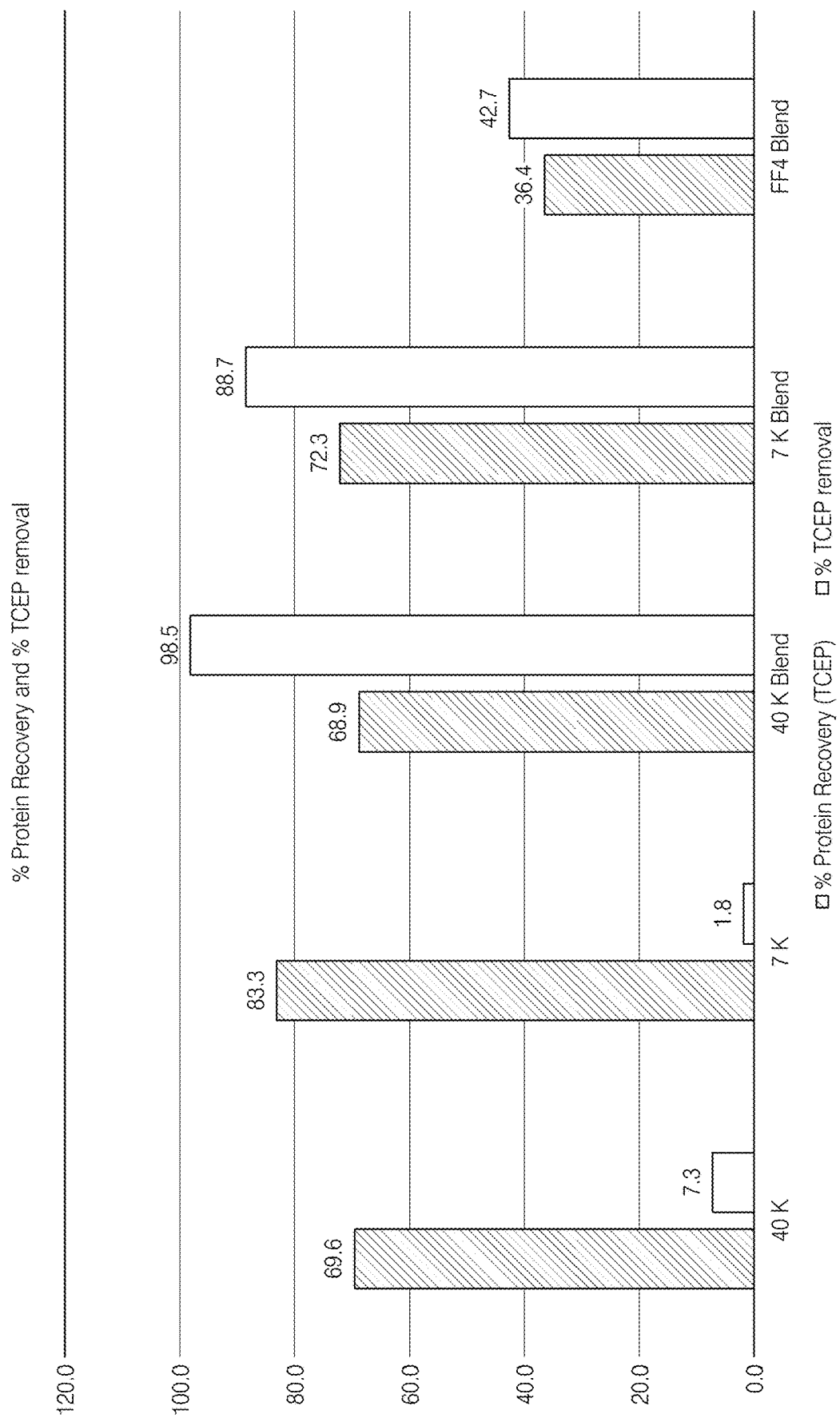
FIG. 13 depicts removal of exemplary small molecules, a reducing agent, and corresponding protein recovery, using a blended composition, devices, kits and methods, according to one embodiment of the disclosure.

FIG. 13 depicts data of removal of an exemplary small molecule reducing agent using a blended composition, devices, kits and methods, according to one embodiment of the disclosure. The experiments were as follows: Reducing Agent Removal Protocol: 1. Pipette 714 µl 70% Resin slurry into spin column that is in a collection tube; 2. Spin out liquid for 2 min at 1000×g; 3. Replace collection tube and add 100 µl of TCEP sample (25 mM) 1 mg/ml Goat Anti Rabbit Antibody in PBS into each spin column for each of samples; 4. Remove TCEP from samples by centrifuging for 2 min at 1000×g.

Assess TCEP Removal by Ellmans Assay: 1. Measured amount of TCEP by adding following for each sample in a 96 well plate; 2. 250 µl Ellmans buffer; 3. 10 µl Ellmans reagent (4 mg/ml); 4. 50 µl sample (diluted 1:10); 5. Read samples at 450 nm on Multiskan plate reader; Access Protein Recovery by A 280 nm; 6. Pipette 4 µL of sample on Nanodrop One and measure A 280 nm.

FIG. 13 is a bar graph showing the removal of reducing agent TCEP using the 7K and 40K Blends (blended with Dextran and PEG Diamine chemistries blended in 1:1 ratio) and compares TCEP removal with unmodified 7K and 40K size exclusion resins and also with a non-size exclusion column comprising a FF4 Blend. The black bars show the % of protein recovered. The grey bars indicate the amount of TCEP removed as a %. The 40K and 7K resin remove 7.3% and 1.8% of TCEP, whereas the 40K Blend and 7K Blend removes 98.5% and 88.7% of TCEP. The FF4 blend, which is the blend made on non-size exclusion resin, removes 42.7% TCEP. The FF4 blend also has a poor comparative recovery of protein (36.4%) as compared to the 40K and 7K Blends which demonstrate comparatively good protein recovery of 68.9% and 72.3%.

Example 6: Blended Compositions for Removal of Small Molecule Biotin

Figure 14:
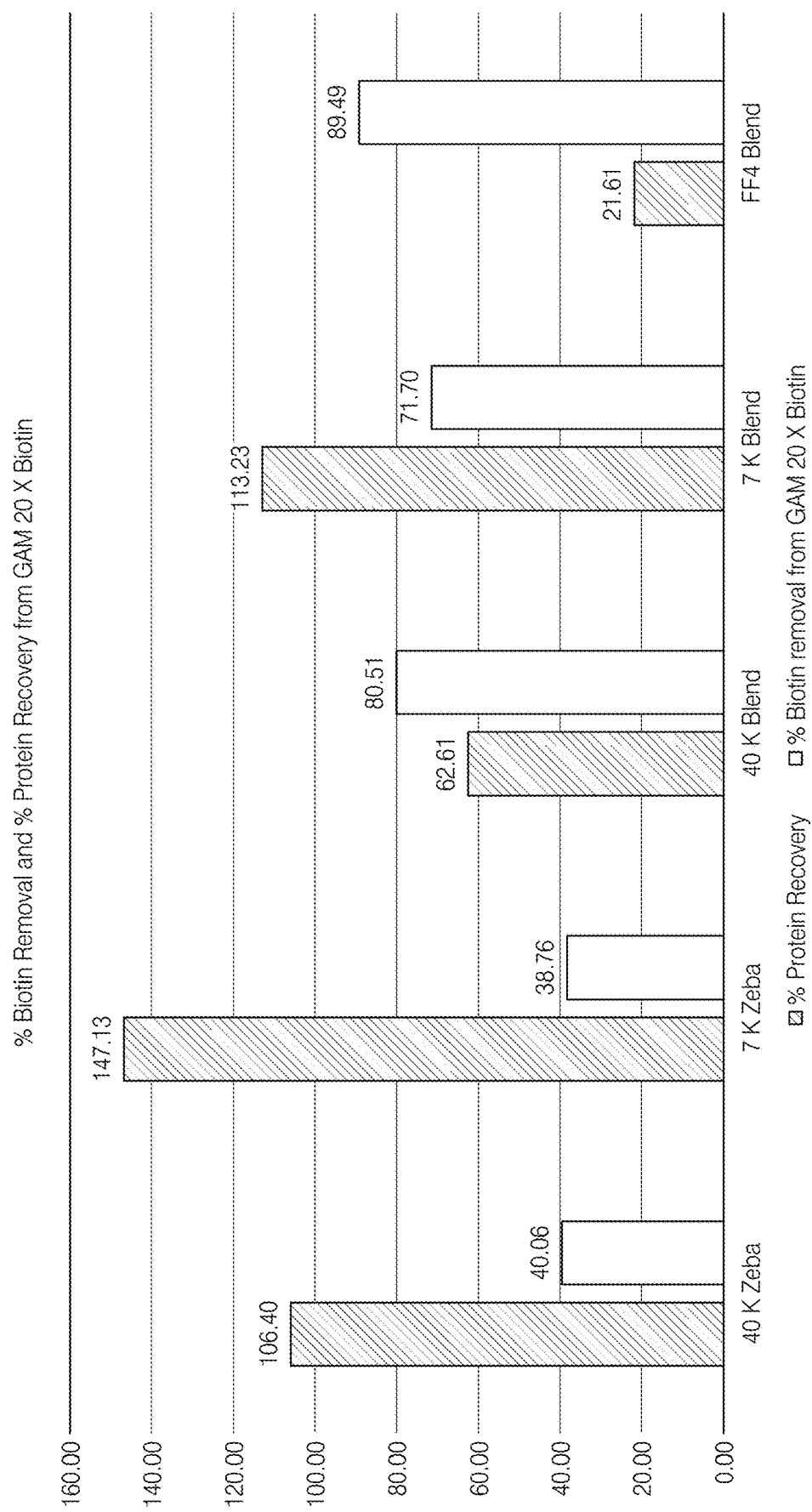
FIG. 14 depicts removal of exemplary small molecules, free biotin, and corresponding protein recovery, using a blended composition, devices, kits and methods, according to one embodiment of the disclosure.

FIG. 14 depicts removal of free/unreacted Biotin using the 7K and 40K Blends of the disclosure. The experiments are as follows:

Biotin Removal Protocol: 1. Pipette 1 ml 50% Resin slurry into spin column that is in a collection tube; 2. Spin out liquid for 2 min at 1000×g; 3. Replace collection tube and add Biotinylated antibody sample into each spin column for each of samples; 4. Remove free Biotin from samples by centrifuging for 2 min at 1000×g.

Assess Biotin Removal: 1. Measured amount of Biotin by adding following for each sample in a cuvette: a) 800 µl of PBS buffer; b) 100 µl Colorimetric HABA; c) 100 µl sample (diluted 1:10); 2. Read samples at 500 nm on Multiskan plate reader.

Assess Biotinylated Protein Recovery: 1. Pipette 10 µl of sample on a 96 well plate; 2. Prepare Pierce™ Rapid Gold BCA Protein assay Working Reagent according to manufacturer instructions; 3. Add 200 µl of the Working reagent to the well; 4. Incubate plate for 5 minutes at Room Temperature; 5. Read Absorbance at 480 nm on a Multiskan plate reader.

FIG. 14 is a bar graph showing removal of free/unreacted Biotin using the 7K and 40K Blends (as described in the examples above) compared to removal of free Biotin using unmodified 7K and 40K resin and the FF4 Blend (as described in the examples above). The black bars indicate % protein recovery (of GAM Ab) and the grey bars indicate amount of free Biotin removed as a %. As demonstrated the unmodified 40K and 7K support remove 40% and 38.75% of free Biotin respectively, whereas the 40K Blend and 7K Blend remove 80.31% and 72.7% of unreacted/free Biotin respectively. The FF4 blend (non-size exclusion blend) shows removal of 89.49% Biotin. However, the FF4 blend has a poor recovery of protein showing a 21.4% protein recovery. In comparison, the 40K and 7K Blends demonstrate good protein recovery.

FIG. 12, FIG. 13 and FIG. 14 show comparatively superior removal of small molecules including exemplary dyes, biotin and reducing agents using the modified 40K and 7 Blends when compared to using unmodified 40K and 7K size exclusion columns. Protein recovery using the non-exclusion resin such as FF4 is comparatively poor.

Example 7: Blended Compositions for Removal of Small Molecules

FIG. 12, FIG. 13 and FIG. 14 show comparatively superior removal of small molecules including exemplary dyes, biotin and reducing agents using the modified 40K and 7 Blends when compared to using unmodified 40K and 7K size exclusion columns. Protein recovery using the non-exclusion resin such as FF4 is comparatively poor.

Additional experiments were also performed with cross linker agent Succinimidyl 4-(N maleimidomethyl) cyclohexane-1-carboxylate (SMCC) and results are summarized in Table 2 below.

Table 2 shows the % of protein recovery using the various Blends described in the Examples above for several different small molecules including the dye (fluorescein), biotin, TCEP & SMCC. As can be seen the blend comprising the non-size exclusion resin FF4 has the least protein recovery for all the small molecules. Even though biotin was removed by FF4 (as shown in Example 8), the protein recovery percentage is less than optimal.

TABLE 2

| Blend | Dye (Fluorescein) | Biotin | TCEP | SMCC |
| --- | --- | --- | --- | --- |
| 40K Blend | 95.7% | 62.6% | 68.9% | 63.1% |
| 7K Blend | 111.9% | 113.2% | 72.3% | 83.8% |
| FF4 Blend | 15.5% | 21.6% | 36.4% | 2% |

Figure 15:
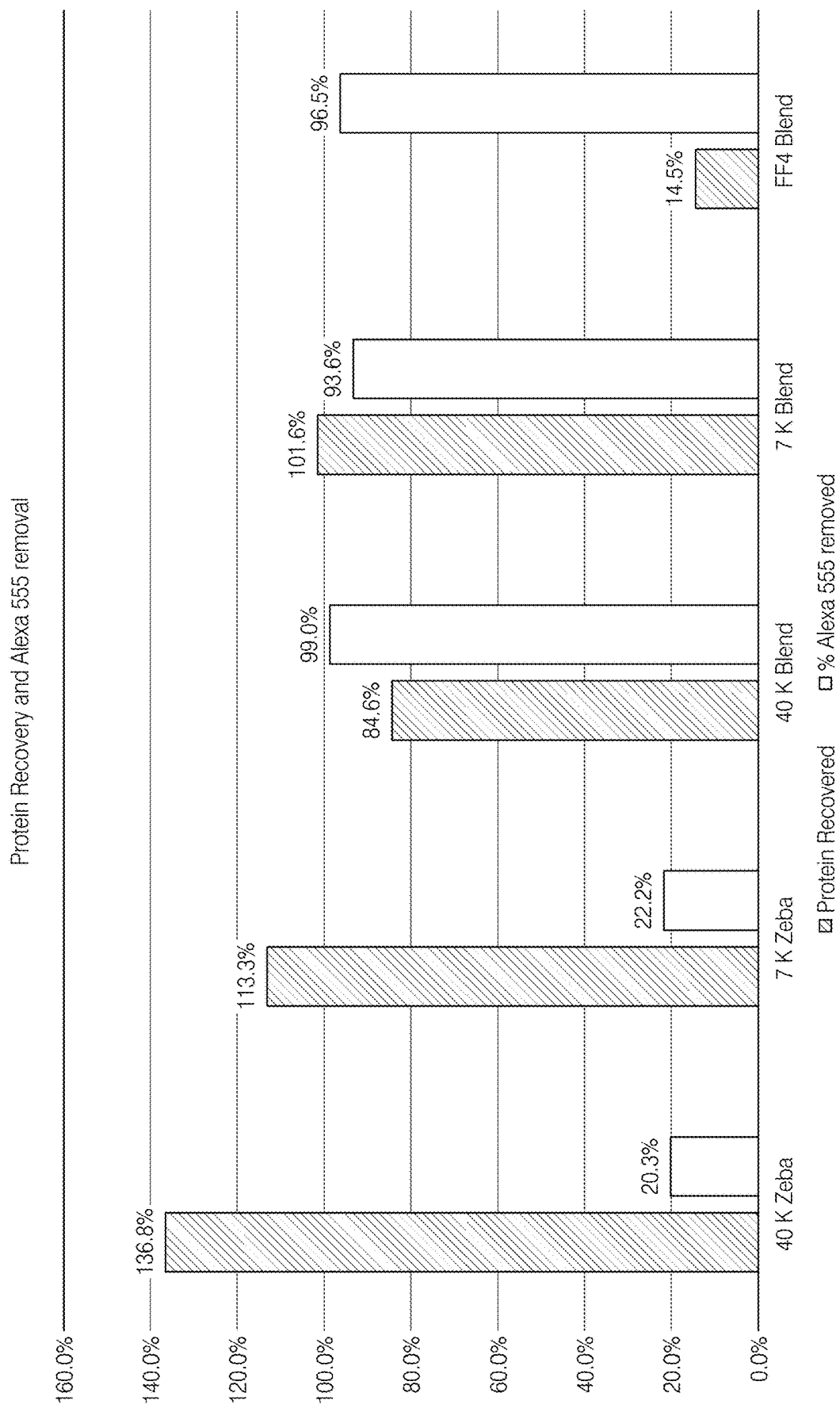
FIG. 15 depicts quantitative data of FIG. 13 removal of exemplary small molecules, free dye Alexa Fluor™ 555 and protein recovery, using a blended composition, devices, kits and methods, according to one embodiment of the disclosure.
Figure 16:
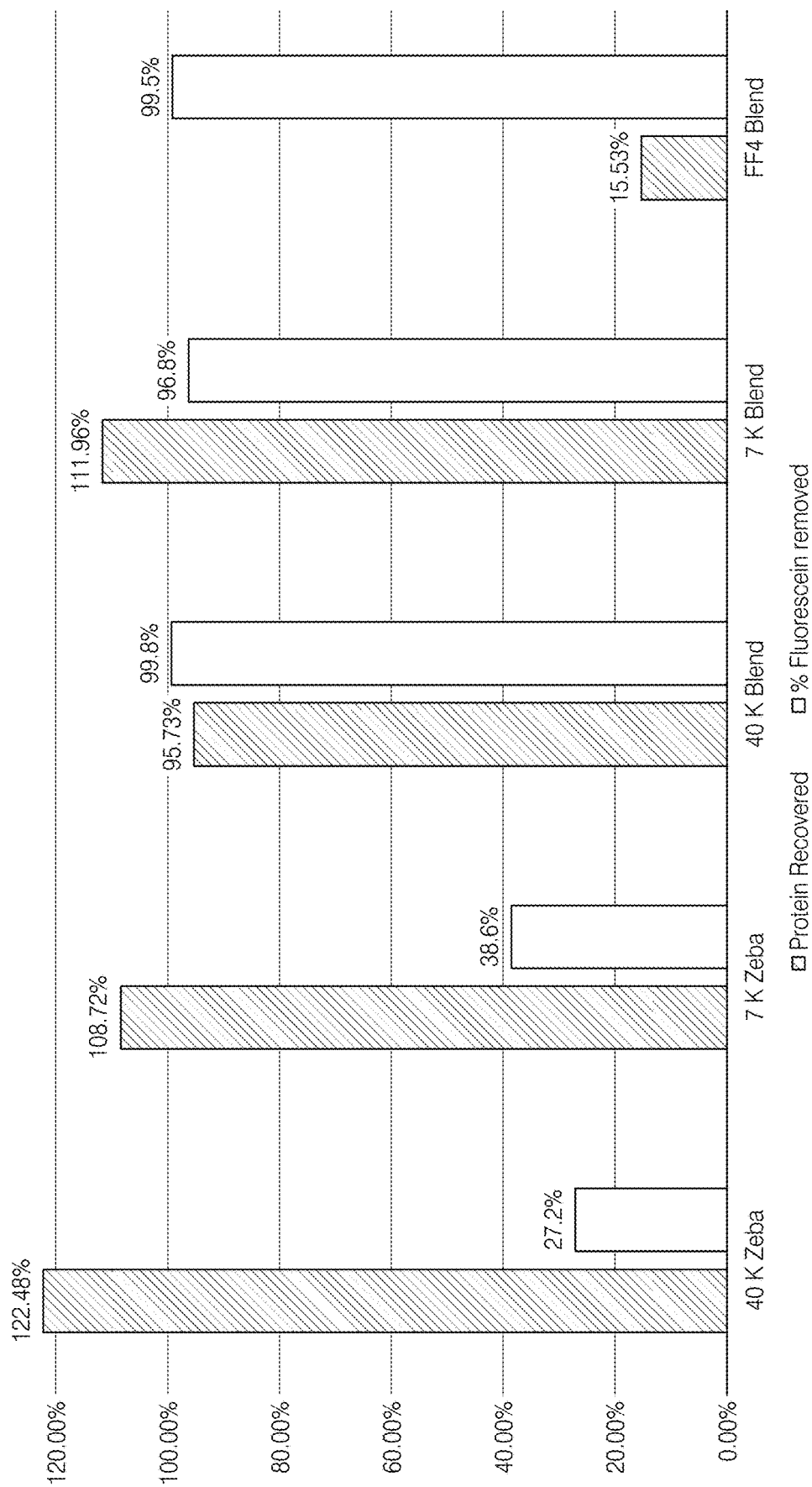
FIG. 16 depicts quantitative data of FIG. 12 removal of exemplary small molecules, free dye Fluorescein, and protein recovery, using a blended composition, devices, kits and methods, according to one embodiment of the disclosure.

FIG. 15 and FIG. 16 are bar graphs from experiments showing protein recovery and Alexa Fluor™ 555 removal the bands that have been quantified from the gel corresponding to FIG. 12 to determine the % Protein recovery and % free dye removal from each of the compositions tested. The grey bars indicate % dye removal and black bars indicate % protein recovery. As demonstrated in FIG. 15 and FIG. 16 the unmodified size exclusion resins 40K Zeba and 7K Zeba resins could not efficiently remove free Fluorescein or free Alexa Fluor™ 555. In contrast, the modified 40K and 7K Blend compositions of the present disclosure were able to remove >96% of Fluorescein and >93% Alexa Fluor™ 555. The non-size exclusion FF4 blend demonstrated poor protein recovery of both the GAR-Fluorescein conjugate protein and the GAM-Alexa Fluor™ 555 conjugate protein with a 15.5% and 14.5% protein recovery respectively.

Figure 17:
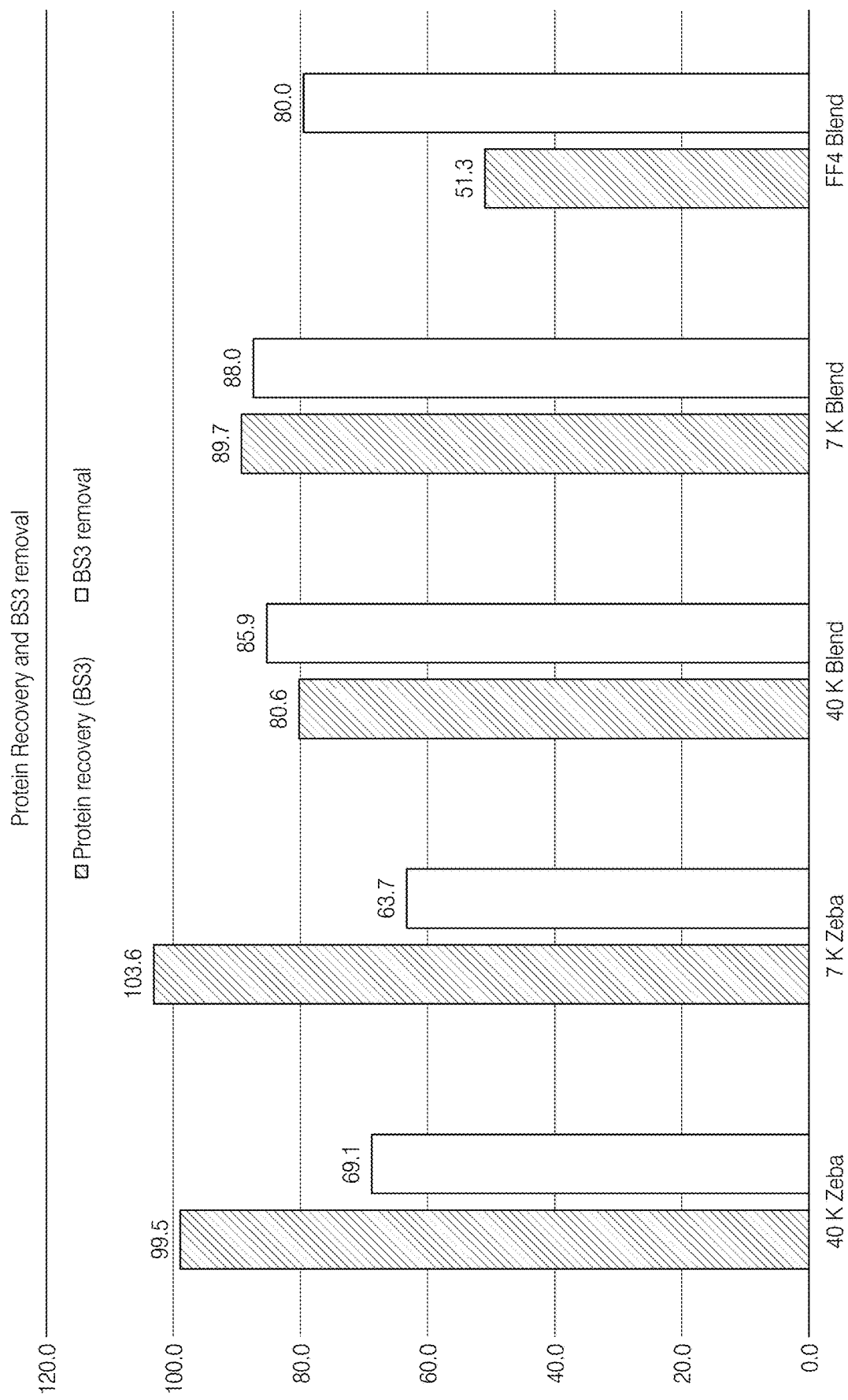
FIG. 17 depicts removal of exemplary small molecules, BS3, Bis(sulfosuccinimidyl) suberate), and protein recovery, using a blended composition, devices, kits and methods, according to one embodiment of the disclosure.

Experimental steps of FIG. 17 are as below: 1. Prepare 1.33 mM BS3 crosslinker solution in PBS; 2. Pipette 1 mL of 50% resin slurry into spin column that is in a collection tube; 3. Spin out liquid for 2 min @ 1000×g; 4. Replace collection tube and add BS3 solution to each spin column; 5. Remove BS3 by centrifuging for 2 min. @ 1000×g.

Assess BS3 Removal: 1. Prepare a 1:50 dilution of each flow through sample in PBS by mixing 50 µl flow through with 450 µl PBS); 2. Read samples at 280 nm on UV Cary in cuvette, 500 µl.

Assess BS3 crosslinked Protein Recovery: 1. Pipette 10 µl of sample on a 96 well plate; 2. Prepare Pierce™ Rapid Gold BCA Protein assay Working Reagent according to manufacturer instructions; 3. Add 200 µl of the Working reagent to the well; 4. Incubate plate for 5 minutes at Room Temperature; 5. Read Absorbance at 480 nm on a Multiskan plate reader.

Experimental steps of FIG. 17 are as below: 1. Prepare 1.33 mM SMCC crosslinker solution in PBS; 2. Pipette 1 mL of 50% resin slurry into spin column that is in a collection tube; 3. Spin out liquid for 2 min @ 1000×g; 4. Replace collection tube and added SMCC solution to each spin column; 4. Remove SMCC by centrifuging for 2 min. @ 1000×g Assess SMCC Removal: 1. Prepare a 1:50 dilution of each flow through sample in PBS by mixing 50 µl flow through with 450 µl PBS); 2. Read samples at 280 nm on UV Cary in cuvette, 500 µl.

Assess SMCC crosslinked Protein Recovery: 1. Pipette 10 µl of sample on a 96 well plate; 2. Prepare Pierce Rapid Gold BCA Protein assay Working Reagent according to manufacturer instructions; 3. Add 200 µl of the Working reagent to the well; 4. Incubate plate for 5 minutes at Room Temperature; 5. Read Absorbance at 480 nm on a Multiskan plate reader.

Figure 18:
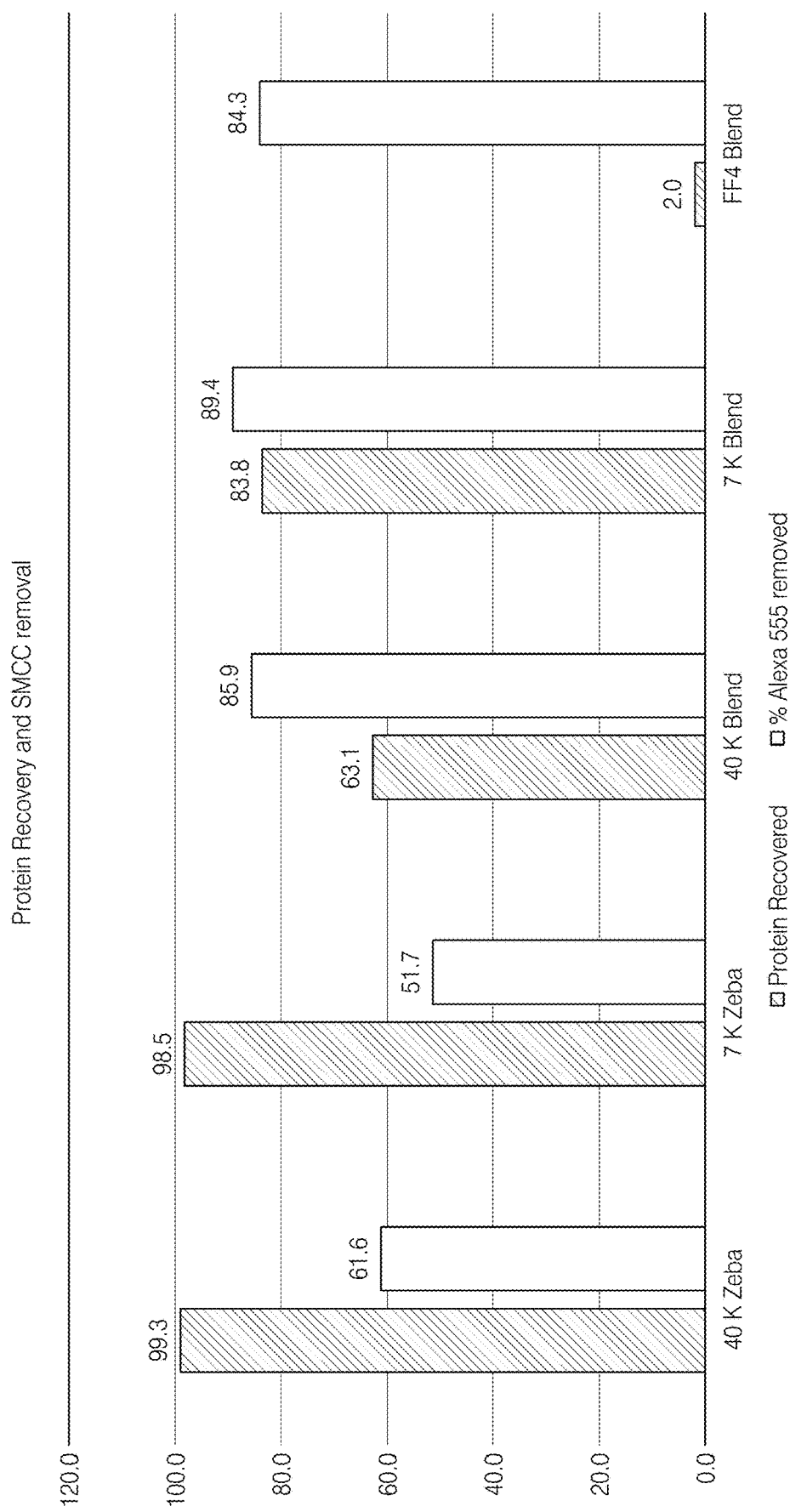
FIG. 18 depicts removal of exemplary small molecules, SMCC, (Succinimidyl 4-(N maleimidomethyl) cyclohexane-1-carboxylate), and protein recovery, using a blended composition, devices, kits and methods, according to one embodiment of the disclosure.

FIG. 17 and FIG. 18 are bar graphs showing small molecules that are used as crosslinkers including Bis(sulfosuccinimidyl) suberate) (BS3) and Succinimidyl 4-(N maleimidomethyl) cyclohexane-1-carboxylate (SMCC) that have been removed using these resins. FIG. 17 shows removal of BS3 crosslinker and FIG. 18 shows removal of SMCC crosslinker. In FIG. 17, the grey bars correspond to BS3 removal in % and demonstrate that the unmodified 40K and 7K Zeba resins remove 69.1% and 63.7% of the BS3 crosslinker while the present compositions comprising the 40K Blend and the 7K Blend remove 85.9% and 88% of the BS3 crosslinker. The FF4 Blend removes 80% of BS3, however the protein recovery properties of FF4 is only about 51%. In contrast, the present compositions of the 40K Blend and the 7K Blend have 80.6% and 89.7% protein recovery.

In FIG. 18 the grey bars indicate SMCC removal in % and demonstrate that the unmodified 40K and 7K Zeba resins remove 61.6% and 53.7% of the SMCC crosslinker, while the present composition blends of the 40K Blend and the 7K Blend remove 85.9% and 89.4% of the SMCC crosslinker respectively. The present composition blends perform 20% better than the unmodified 7K and 40K. The FF4 Blend removes 84.3% of crosslinker, however, protein recovery properties of FF4 are comparatively poor and only 2% of the protein was recovered. In contrast, the 40K Blend and the 7K Blend shows 63.1% and 83.8% protein recovery.

Figure 19:
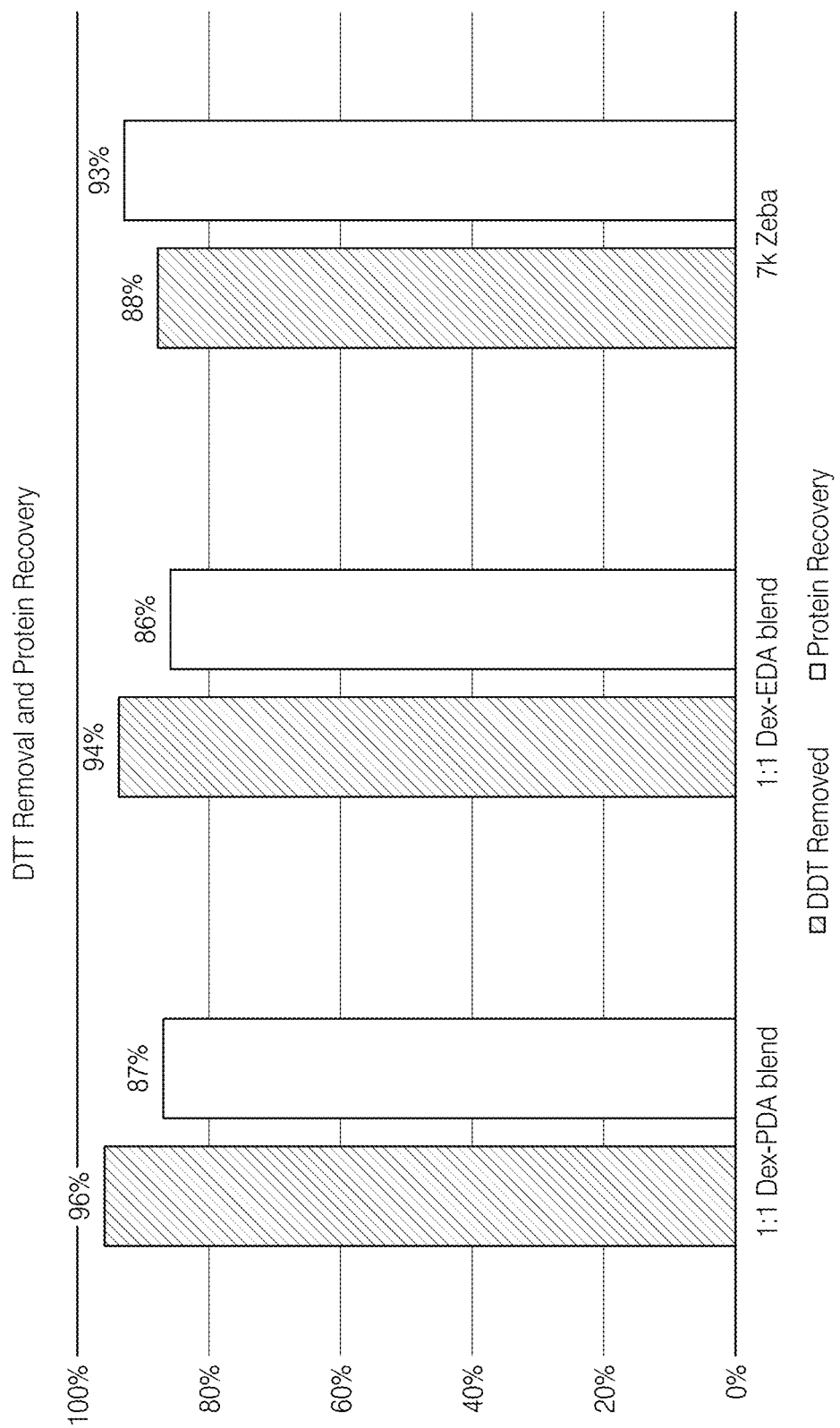
FIG. 19 depicts removal of exemplary small molecules, DTT (Dithiothreitol), and protein recovery, using blended compositions, devices, kits and methods, according to one embodiment of the disclosure FIG. 20A

The present inventors also have shown that compositions of the disclosure comprising Blends of Dextran and PDA moieties and Blends of Dextran and EDA moieties immobilized onto size exclusion supports can remove significantly large quantities of reducing agents such as Dithiothreitol (DTT). This is depicted in FIG. 19 where the black bars indicates % removal of DTT and the grey bars indicate % protein recovery of goat anti rabbit IgG. The 7K resin removed >95% of DTT with a protein recovery of >85%.

Example 8: Compositions of the Disclosure vs Other Existing Products for Protein Recovery and Removal of Small Molecules (Dyes, Biotin, Reducing Agent)

Compositions of the disclosure demonstrated better performance for dye, biotin and reducing agent removal with excellent protein recovery when compared to columns comprising other existing products sold for similar uses.

Figure 20A:
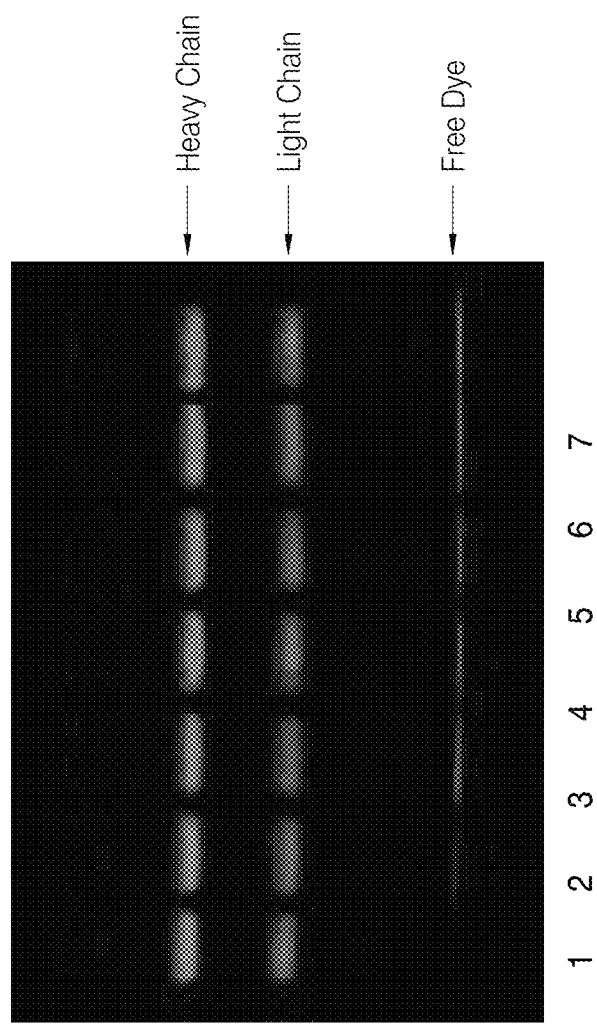
FIG. 20B depicts removal of an exemplary small molecule, a free dye Alexa Fluor™ 647, and protein recovery, using a composition, a device, kits and/or methods, according to one embodiment of the disclosure compared to removal of the small molecule and protein recovery by other existing products sold for similar uses.
Figure 20B:
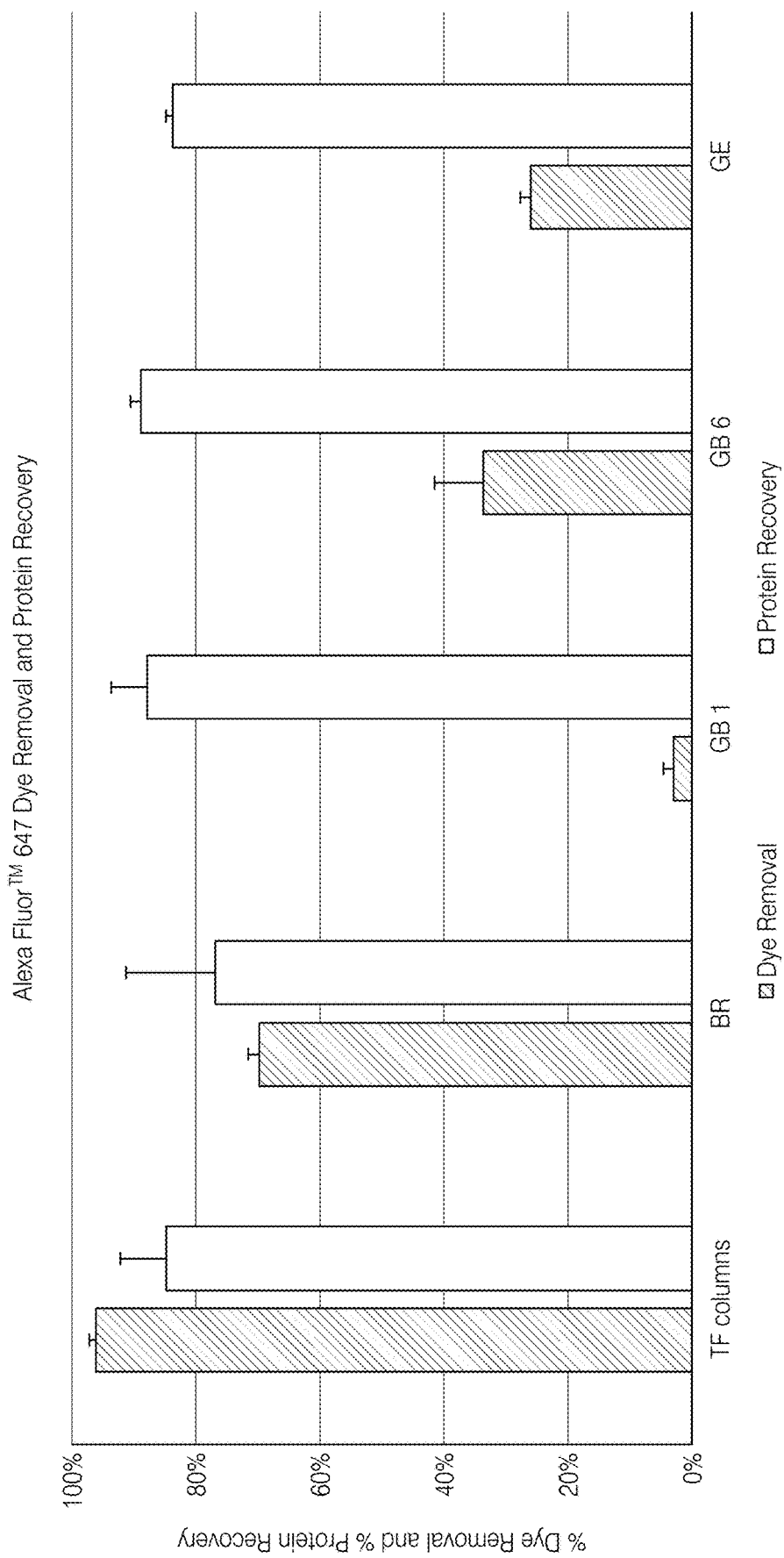

FIG. 20A and FIG. 20B depict use of spin columns comprising a composition of the disclosure or comprising products from other suppliers sold for similar uses, as well as standard dialysis, to compare dye removal and protein recovery. Spin columns comprising compositions of the disclosure or spin columns comprising products from other suppliers were used to remove free Alexa Fluor™ 647 Dye from 100 µl samples of 10 mg/mL Goat Anti-Rabbit IgG labeled with 10 molar excess Alexa Fluor™ 647. Equal volume of sample from each flow through and starting sample (Lane 7) were loaded in the gel. iBright Analysis Software was used to quantitate free dye removal after samples were run on electrophoresis gel and imaged on iBright FL1500 Imaging System (Thermo Fisher Scientific).

FIG. 20A depicts an electrophoresis gel with the following: Lane 1: spin column comprising composition of the disclosure for dye and biotin removal, Lane 2: BioRad P-30, Lane 3: G-Biosciences GT-100, Lane 4: G-Biosciences GT-600, Lane 5: GE PD10, Lane 6: Thermo Scientific Slide-A-Lyzer G2 Dialysis Cassette, 3.5K MWCO, Lane 7: (positive control) Starting sample, 10 mg/ml Goat Anti-Rabbit IgG 10 molar excess Alexa Fluor™ 647.

FIG. 20B depicts graphical data showing dye removal and protein recovery for spin column's comprising: composition of the disclosure for small molecule removal (first set of bars), BioRad P-30 (second set of bars labeled "BR"), G-Biosciences GT-100 (third set of bars labeled "GB 1"), G-Biosciences GT-600 (fourth set of bars labeled "GB 6"), GE PD10 (fifth set of bars labeled "GE").

As seen in FIGS. 20A and 20B spin columns of the present disclosure provide higher dye removal with excellent protein recovery when compared to products from other suppliers.

Figure 21:
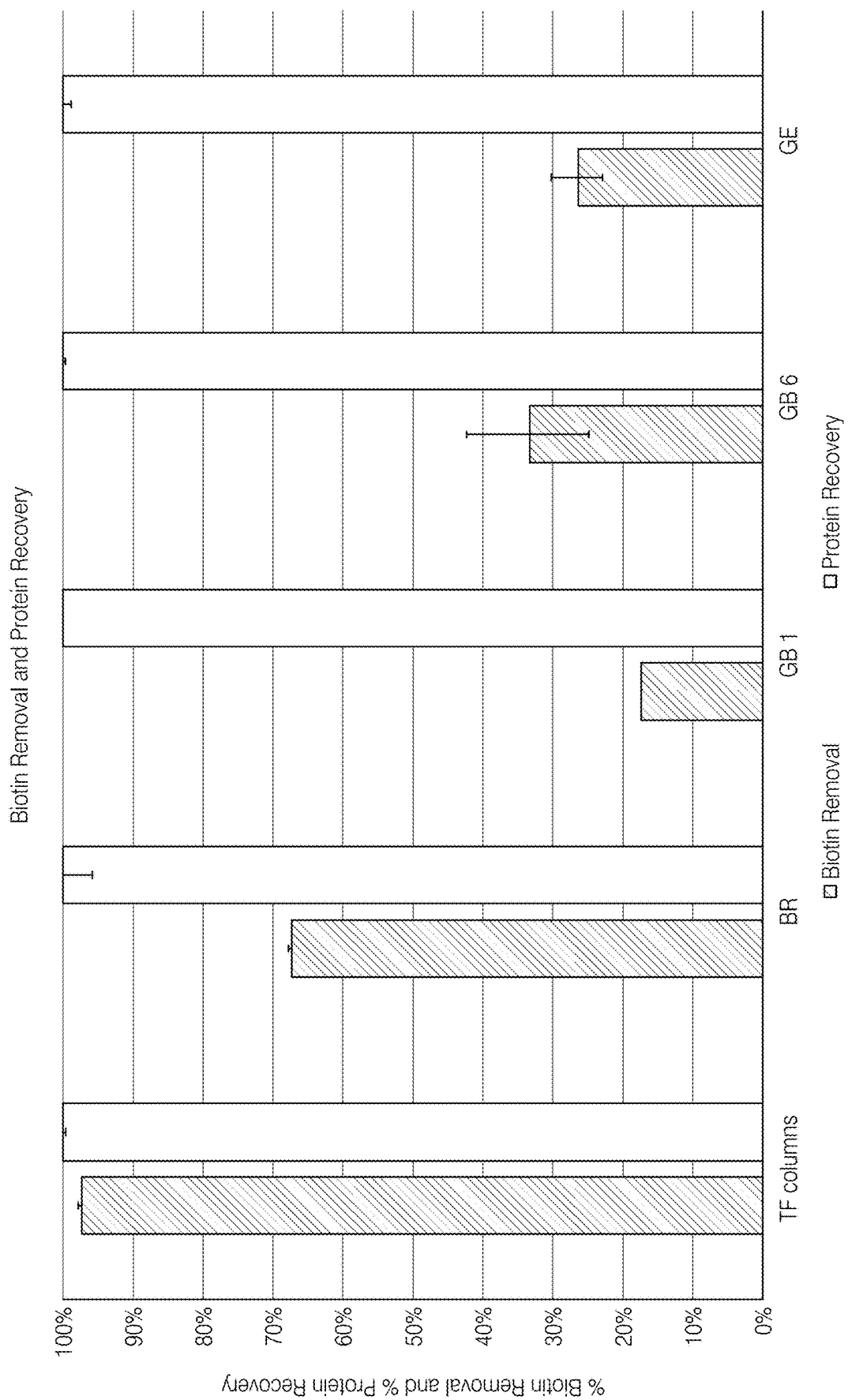
FIG. 21 depicts removal of an exemplary small molecule, biotin, and protein recovery, using a composition, a device, kits and/or methods, according to one embodiment of the disclosure compared to removal of the small molecule and protein recovery by other existing products sold for similar uses.

FIG. 21 depicts use of spin columns comprising a composition of the disclosure or spin columns comprising products from other suppliers sold for similar uses, to compare biotin removal and protein recovery.

Spin columns comprising compositions of the disclosure or spin columns comprising products from other suppliers were used to remove Biotin. 0.27 mM of free NHS LC Biotin was present in 100 µl samples. Protein recovery of Goat Anti Mouse (2 mg/mL) labeled with 20× of NHS-LC-Biotin was assessed by Pierce™ Rapid Gold BCA Assay Kit (Thermo Fisher Scientific Cat. No. #A 53225). Thermo Scientific Biotin Quantitation kit (Thermo Fisher Scientific Cat. No. #28005) was used to quantitate free biotin removal.

FIG. 21 depicts graphical data showing biotin removal and protein recovery for spin column's comprising: composition of the disclosure for small molecule removal (first set of bars), BioRad P-30 (second set of bars labeled "BR"), G-Biosciences GT-100 (third set of bars labeled "GB 1"), G-Biosciences GT-600 (fourth set of bars labeled "GB 6"), GE PD10 (fifth set of bars labeled "GE").

As seen in FIG. 21 spin columns of the present disclosure provide higher biotin removal with higher protein recovery when compared to products from other suppliers.

Figure 22:
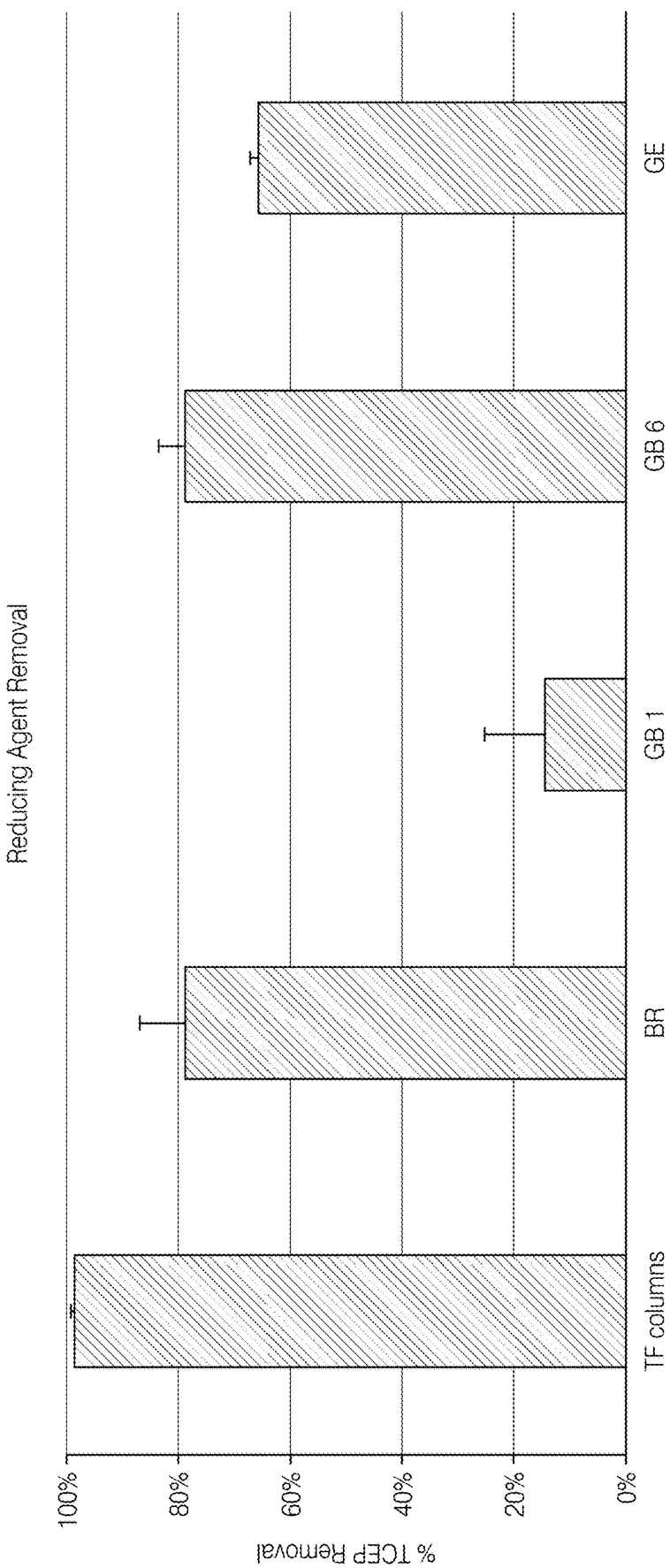
FIG. 22 depicts removal of an exemplary small molecule, a reducing agent TCEP, using a composition, a device, kits and methods, according to one embodiment of the disclosure compared to removal of the reducing agent by other existing products sold for similar uses.

FIG. 22 depicts use of spin columns comprising a composition of the disclosure or spin columns comprising products from other suppliers sold for similar uses, to compare reducing agent removal.

Spin columns comprising compositions of the disclosure or spin columns comprising products from other suppliers were used to remove the reducing agent TCEP from of 1 mg/mL goat anti-rabbit IgG containing 25 mM TCEP in PBS. Reducing agent removal was performed by applying 700 µl of sample to 2 mL columns. Quantification of TCEP removal from flow through compared to starting sample was performed using Ellman's Assay.

FIG. 22 depicts graphical data showing TCEP removal for spin column's comprising: composition of the disclosure for small molecule removal (first set of bars), BioRad P-30 (second set of bars labeled "BR"), G-Biosciences GT-100 (third set of bars labeled "GB 1"), G-Biosciences GT-600 (fourth set of bars labeled "GB 6"), GE PD10 (fifth set of bars labeled "GE"). As can be seen % TCEP removal was much higher in spin columns comprising compositions of the present disclosure when compared to other spin columns tested.

Example 9: Compositions of the Disclosure vs Dialysis for Removal of Small Molecules (Dyes & Biotin)

Compositions of the disclosure were compared to Dialysis which is a standard method used in the art to purify small molecule impurities from proteins. Compositions of the disclosure demonstrated better performance for dye and biotin removal with higher protein recovery in a fraction of the time required for Dialysis.

Figure 23:
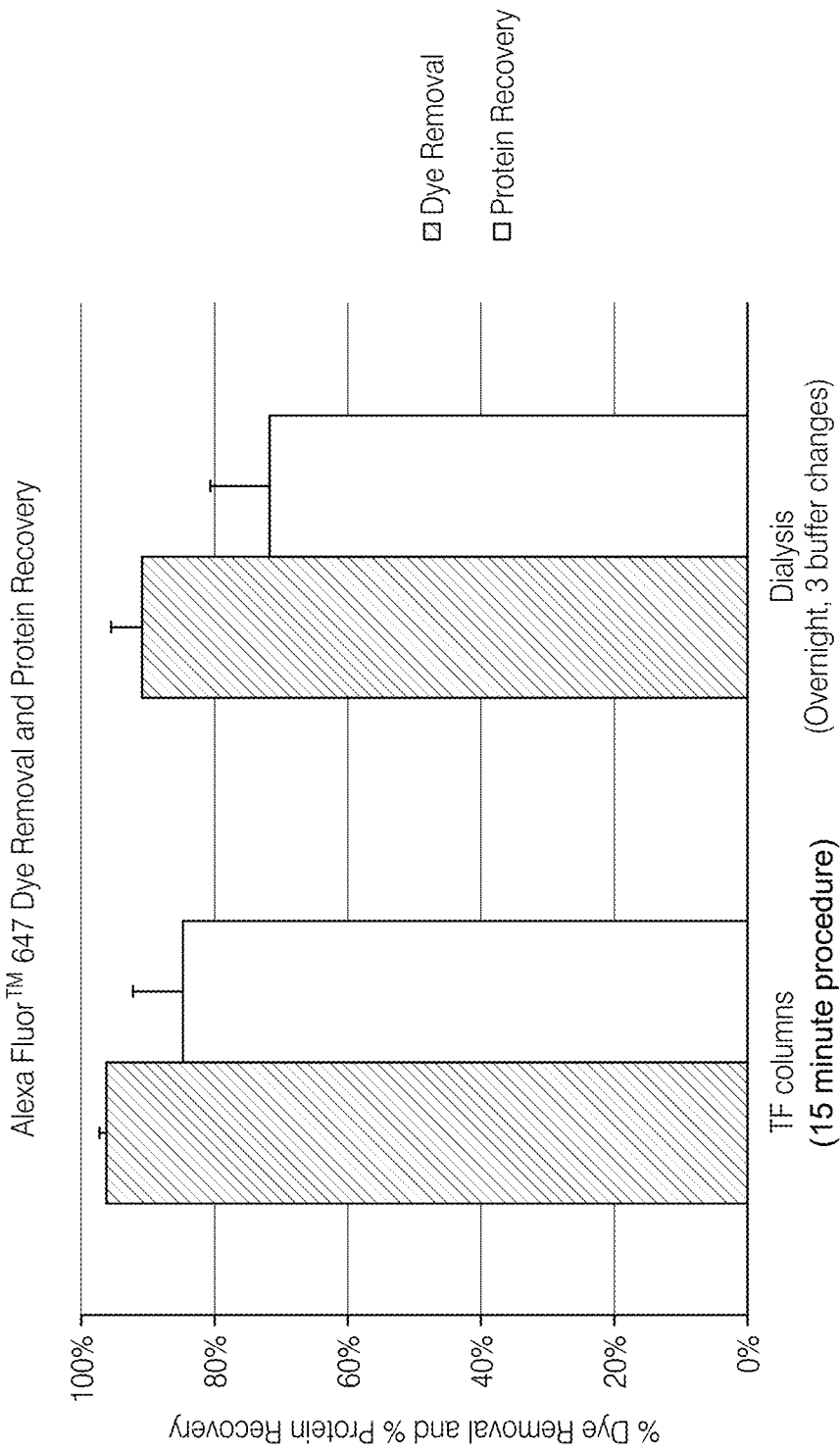
FIG. 23 depicts removal of an exemplary small molecule, a free dye Alexa Fluor™ 647, and protein recovery, using a composition, a spin column device, kits and methods, according to one embodiment of the disclosure, compared to use of existing dialysis methods to remove free Alexa Fluor™ 647 Dye.

As shown in FIG. 23 spin columns comprising a composition of the disclosure for small molecule removal were compared to standard dialysis to remove free Alexa Fluor™ 647 Dye from samples of 10 mg/mL Goat Anti-Rabbit IgG labeled with Alexa Fluor™ 647 (10 molar excess). Protein recovery was assessed by A280 measurements of starting sample and flow through after dye removal. iBright Analysis Software was used to quantitate free dye removal after samples were run on electrophoresis gel and imaged on iBright FL1500 Imaging System (Thermo Fisher Scientific, Product #A44241).

As seen in the graphical data in FIG. 23 dye removal and protein recovery for spin columns comprising composition of the disclosure for small molecule removal (first set of bars), were superior to those for dialysis. Furthermore, methods using spin columns of the present disclosure take only 15 minutes as compared to overnight with three buffer changes for Dialysis. Accordingly, the present compositions and methods provide surprisingly pure protein and removal of small molecules in a one step process that is significantly faster than dialysis.

Figure 24:
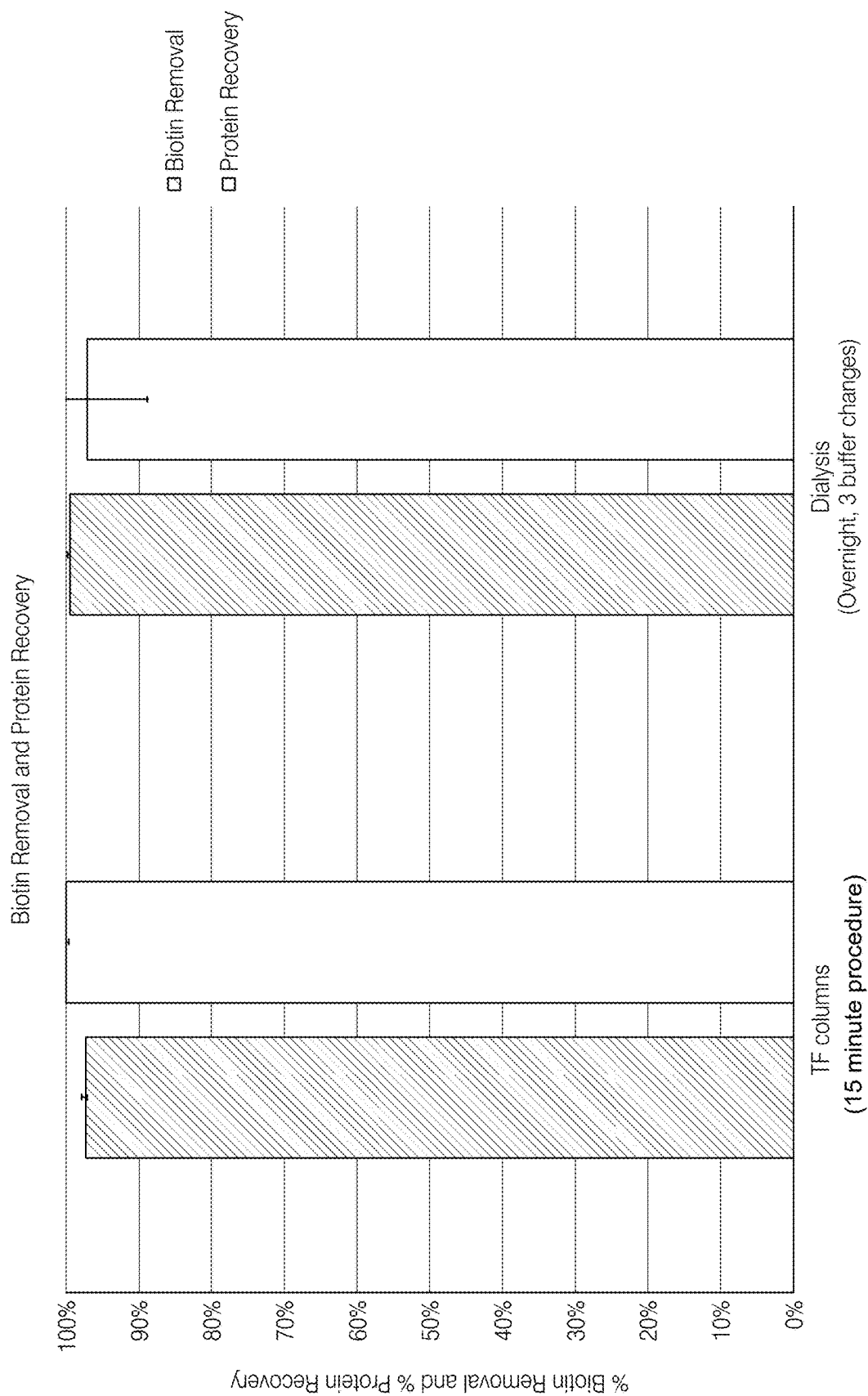
FIG. 24 depicts removal of an exemplary small molecule, biotin, and protein recovery, using a composition, a device, kits and methods, according to one embodiment of the disclosure compared to existing dialysis methods for removing biotin.

FIG. 24 depicts data for spin columns comprising a composition of the disclosure for small molecule removal compared to standard dialysis to remove free NHS-LC-Biotin. Protein recovery of Goat Anti Rabbit (2 mg/mL) labeled with 20× of NHS-LC-Biotin was assessed by the Rapid Gold BCA Test (Thermo Fisher Scientific, Product #A53225).

As seen in the graphical data in FIG. 24, biotin removal and protein recovery for spin column's comprising composition of the disclosure for small molecule removal (first set of bars), were superior to those for dialysis. Furthermore, methods using spin columns of the present disclosure take only 15 minutes as compared to overnight with three buffer changes for Dialysis. Accordingly, the present compositions and methods provide surprisingly pure protein and removal of small molecules in a one step process that is significantly faster than dialysis.

Example 10: Compositions of the Disclosure in a Spin Plate Device for Removal of Small Molecules Compositions of the disclosure were placed in a Spin Plate Device to test removal of small molecules. In some embodiments, compositions of the disclosure were placed in 96-well filter plates to test high-through put removal of small molecules from a plurality of samples.

Figure 25:
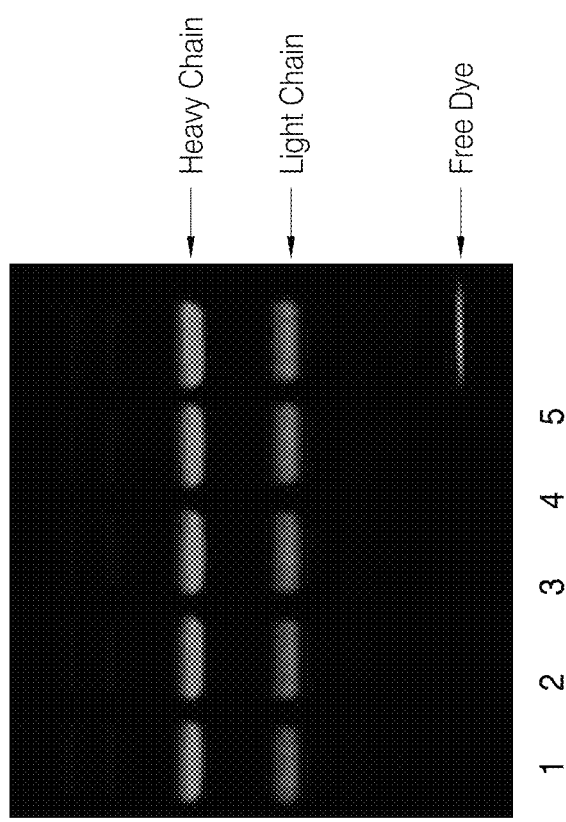
FIG. 25 depicts removal of an exemplary small molecule, a free dye Alexa Fluor™ 647, and protein recovery, using a composition, a spin plate device, kits and methods, according to one embodiment of the disclosure.

As can be seen in FIG. 25, compositions of the disclosure for removal of small molecules were placed in 96-well filter plates to remove free Alexa Fluor™ 647 Dye from 50 µl (lanes 1 and 2) and 100 µl samples (lanes 3 and 4) of 10 mg/mL Goat Anti-Rabbit IgG labeled with 10 molar excess Alexa Fluor™ 647. Equal volume of sample from each flow through and starting sample (Lane 5, positive control) were loaded in the gel. iBright Analysis Software was used to quantitate free dye removal after samples were run on electrophoresis gel and imaged on iBright FL1500 Imaging System (Thermo Fisher Scientific, Product #A44241). Dye removal and excellent protein recovery were demonstrated.

Example 11: Compositions of the Disclosure for Removal of Small Molecule Fluorescein Dyes Compositions of the disclosure were placed in spin columns to test removal of fluorescein dyes.

Figure 26:
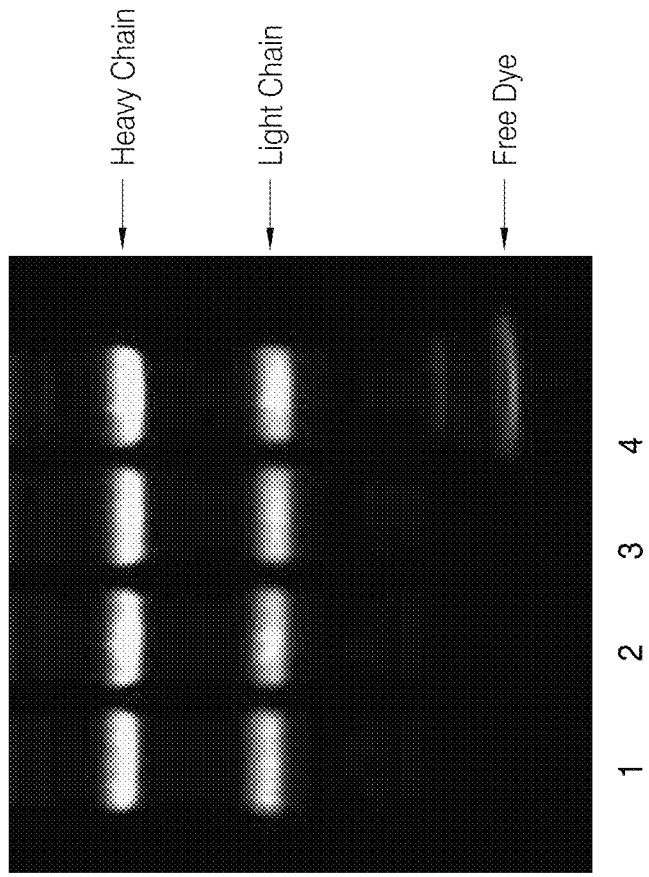
FIG. 26 depicts removal of an exemplary small molecule, a free dye Fluorescein dye, and protein recovery, using a composition, a spin column device, kits and methods, according to one embodiment of the disclosure.

As can be seen in FIG. 26, compositions of the disclosure for removal of small molecules were placed in a spin column to remove free Fluorescein Dye (Thermo Fisher Scientific Cat. No. #46410) from 100 μl samples of 10 mg/mL Goat Anti-Rabbit IgG labeled with 15 molar excess Fluorescein. Equal volume of sample from each flow through (Lanes 1-3) and starting sample (Lane 4) were loaded in the gel. iBright Analysis Software was used to quantitate free dye removal after samples were run on electrophoresis gel and imaged on iBright FL1500 Imaging System (Thermo Fisher Scientific, Product #A44241). Dye removal and excellent protein recovery were demonstrated.

Example 12: Compositions of the Disclosure for Immunofluorescence Applications

Compositions, devices and methods of the disclosure are found to be useful for immunofluorescence applications.

Figure 27B:
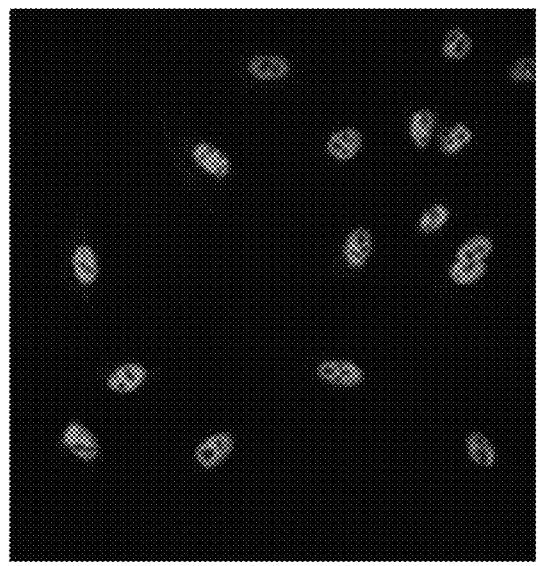
FIG. 27A and FIG. 27B depict immunofluorescence images of exemplary cells stained with a Polyclonal Antibody—Alexa Fluor™ 647 conjugate, and show the removal of excess free dye, Alexa Fluor™ 647, by cleanup using a spin column comprising compositions of the present disclosure (FIG. 27B) in comparison with an immunofluorescent image of the same cells without cleanup (by not using a spin column of the disclosure) (FIG. 27A)
Figure 27A:
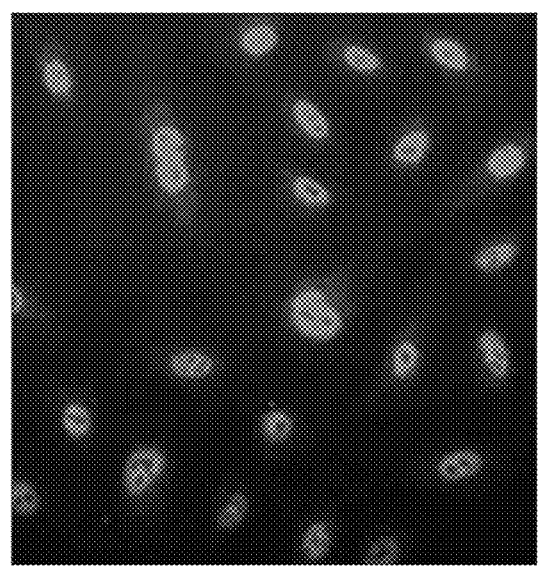

In one example, HDAC2 polyclonal antibody (Thermo Fisher Scientific, Product #PA1-861) was labeled with Alexa Fluor™ 647 (Thermo Fisher Scientific, Product #A20006) and then purified from unreacted dye using a spin column comprising a composition of the disclosure for removing small molecules. FIG. 27A and FIG. 27B show immunofluorescent analysis of HDAC2 (red) in A549 cells. Cells were fixed with 4% Paraformaldehyde in PBS for 15 minutes at room temperature, permeabilized with 0.1% Triton X-100 in PBS for 15 minutes and blocked with 1% BSA in PBS. Cells were stained with a HDAC2 Polyclonal Antibody, Alexa Fluor™ 647 conjugate with cleanup using a spin column with compositions of the present disclosure (FIG. 27B) and without cleanup by not using a spin column of the disclosure (FIG. 27A) of unreacted dye at a dilution of 2.5 μg/ml in blocking buffer for 1 hour at room temperature protected from light.

As seen, FIG. 27A shows a lot of background fluorescence as compared to FIG. 27B which has significantly reduced residual background.

In another example, clean-up of small molecule dye in immunofluorescence was compared with clean-up using an existing product sold for similar use.

PMP70 polyclonal antibody (Thermo Fisher Scientific, Product #PA1-650) was labeled with Alexa Fluor™ 647 (Thermo Fisher Scientific, Product #A20006) and then purified from unreacted dye using a spin column comprising a composition of the disclosure for removing small molecules. Immunofluorescent analysis of PMP70 (red in the originals however shown in black and white drawing here) in A549 cells was done as follows. Cells were fixed with 4% Paraformaldehyde in PBS for 15 minutes at room temperature, permeabilized with 0.1% Triton X-100 in PBS for 15 minutes and blocked with 1% BSA in PBS. Cells were stained with a PMP70 Monoclonal Antibody, Alexa Fluor™ 647 conjugate 1) without cleanup (FIG. 28A), 2) with cleanup using an existing product GE PD-10 Column (FIG. 28B), and 3) with cleanup using a spin column of the present disclosure (FIG. 28C), of unreacted dye at a dilution of 2.5 ug/ml in blocking buffer for 1 hour at room temperature protected from light. Nuclei (blue in the originals but shown in black and white figures here) were stained with Hoechst Dye at a dilution of 10,000 in blocking buffer.

Figures 28A, 28B, 28C:
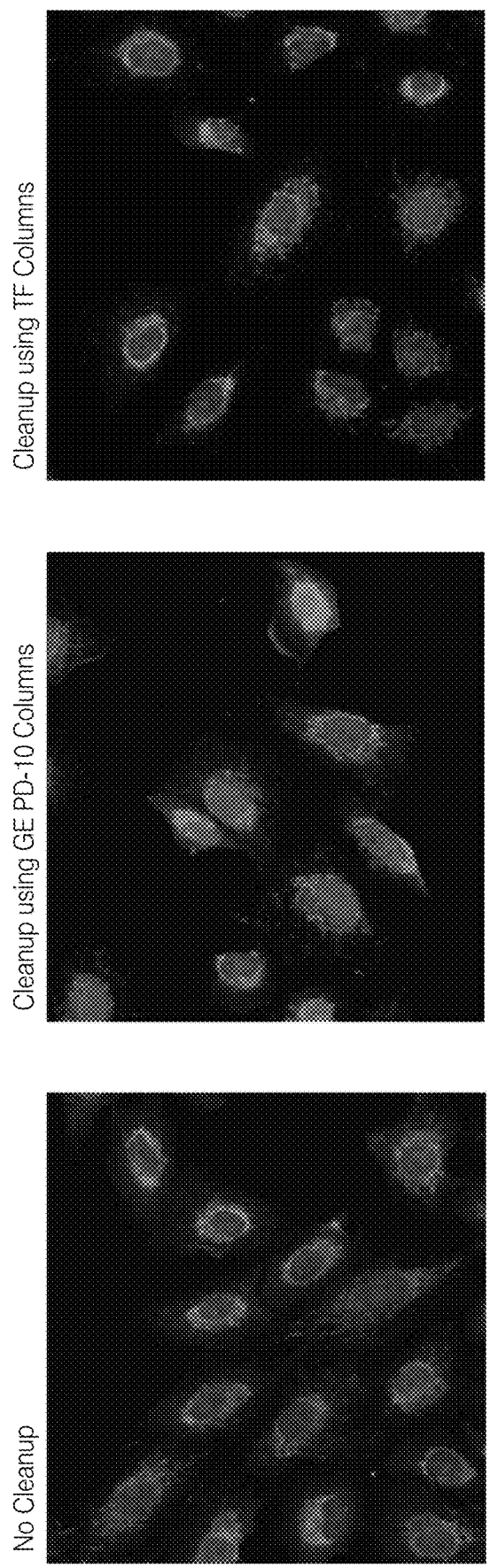
FIG. 28A, FIG. 28B and FIG. 28C depict immunofluorescence images of exemplary cells stained with a Polyclonal Antibody labeled with Alexa Fluor™ 647, and show the removal of excess free dye, Alexa Fluor™ 647, by cleanup using a spin column comprising compositions of the present disclosure (FIG. 28C), in comparison with an immunofluorescent image of the same cells without cleanup (by not using a spin column of the disclosure) (FIG. 28A); and further in comparison with an immunofluorescent image of the same cells where cleanup was done by using a spin column of having an existing product GE PD10 (FIG. 28B)

As seen, FIG. 28A shows a lot of background immunofluorescence, reduced background fluorescence is seen in FIG. 28B, and FIG. 28C shows significantly residual background fluorescence indicating superior clean-up of the dye using spin columns of the present disclosure.

In yet another example, ZO-1 monoclonal antibody (Thermo Fisher Scientific, Product #MA3-39100) was labeled with Alexa Fluor™ 488 (Thermo Fisher Scientific, Product #A20000) and then purified from unreacted dye using a spin column comprising a composition of the disclosure for removing small molecules. Immunofluorescent analysis of ZO-1 (green in the originals but shown in black and white figures here) was done in Caco-2 cells. Cells were fixed with 4% Paraformaldehyde in PBS for 15 minutes at room temperature, permeabilized with 0.1% Triton X-100 in PBS for 15 minutes and blocked with 1% BSA in PBS. Cells were stained with a ZO-1 Polyclonal Antibody, Alexa Fluor™ 488 conjugate with cleanup using a spin column with compositions of the present disclosure (FIG. 29B) and without cleanup by not using a spin column of the disclosure (FIG. 29A) at a dilution of 5 ug/ml in blocking buffer for 1 hour at room temperature protected from light.

Figure 29B:
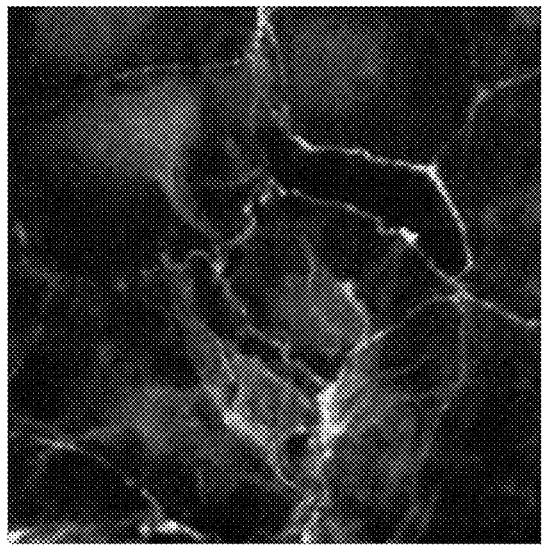
FIG. 29A, and FIG. 29B depict immunofluorescence images of exemplary cells stained with a Monoclonal Antibody labeled with Alexa Fluor™ 488, and show the removal of excess free dye, Alexa Fluor™ 488, by a spin column with compositions of the present disclosure (FIG. 29B) in comparison with an immunofluorescent image of the same cells without cleanup (by not using a spin column of the disclosure) (FIG. 29A)
Figure 29A:
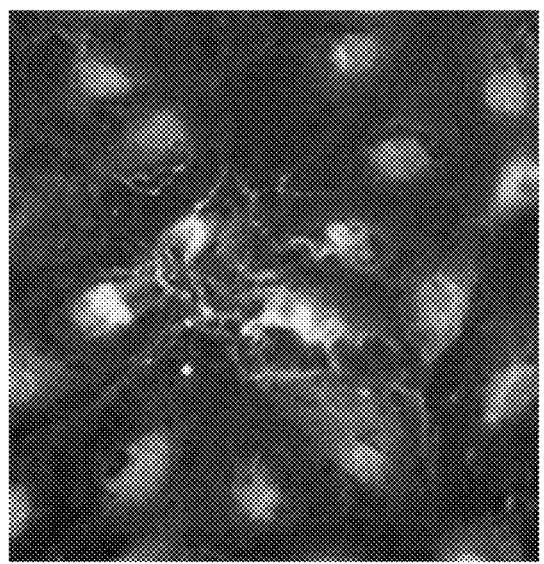

As seen, FIG. 29A shows a lot of background fluorescence as compared to FIG. 29B which has significantly reduced residual background.

Example 14: Compositions of the Disclosure vs Ion Exchange Resins for Protein Recovery and Removal of Small Molecules All experiments to remove small molecules (in this Example) were done using a 0.5 mL resin bed volume (of various chemistries as described variously above and below) assembled into in a 0.8 mL spin column to create a non-limiting embodiment apparatus of the disclosure. In this particular example, spin columns were filled with either compositions of the disclosure (Labeled as Roomba in the Corresponding Figures) or with the ion-exchange resin Dowex. The spin-column was spun at 1000×g for 2 minutes to remove the storage solution. The spin-column was then placed in a clean 2 mL centrifuge tube. Sample volume of 50 μL, 250 μL and 400 μL was added to the center of the resin and the column was spun at 1000×g for 2 minutes and the flow-through was collected in the 2 mL tube. The flow-through was collected. 10 μL of the flow-through was added to 90 μL of sample buffer. 10 μL of this was then added per well on a 4-20% Tris Glycine SDS gel. The gel was run for 40 minutes and was then imaged using the iBright imager (Thermo Fisher Scientific).

Figure 30A:
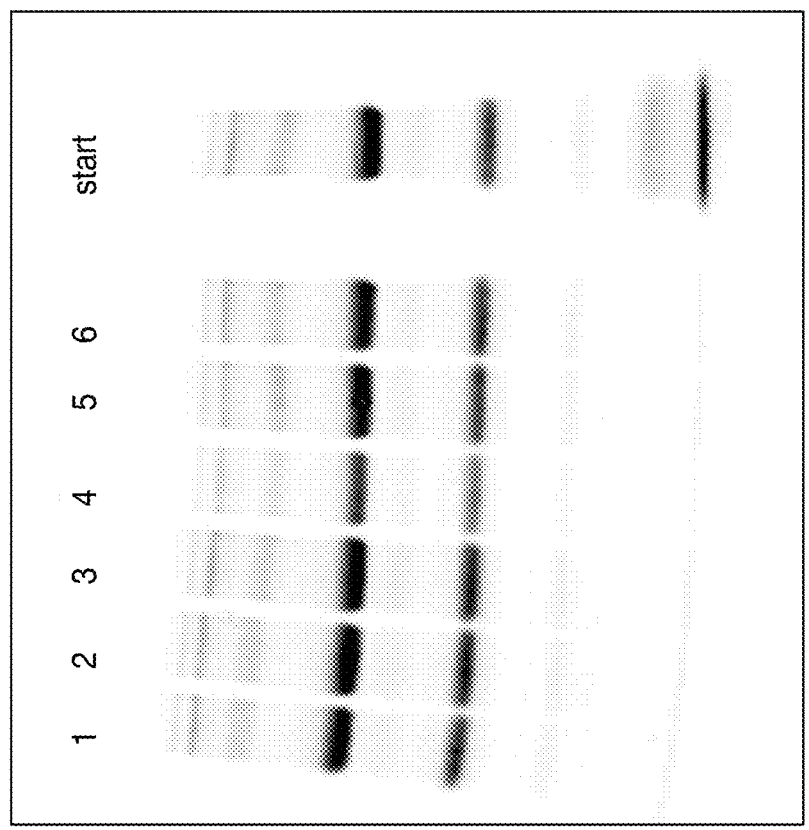
FIG. 30A and FIG. 30B depict comparison of protein recovery and dye removal compositions, devices and methods of the present disclosure (Roomba) with an ion exchange resin (Dowex), according to one embodiment.
Figure 30B:
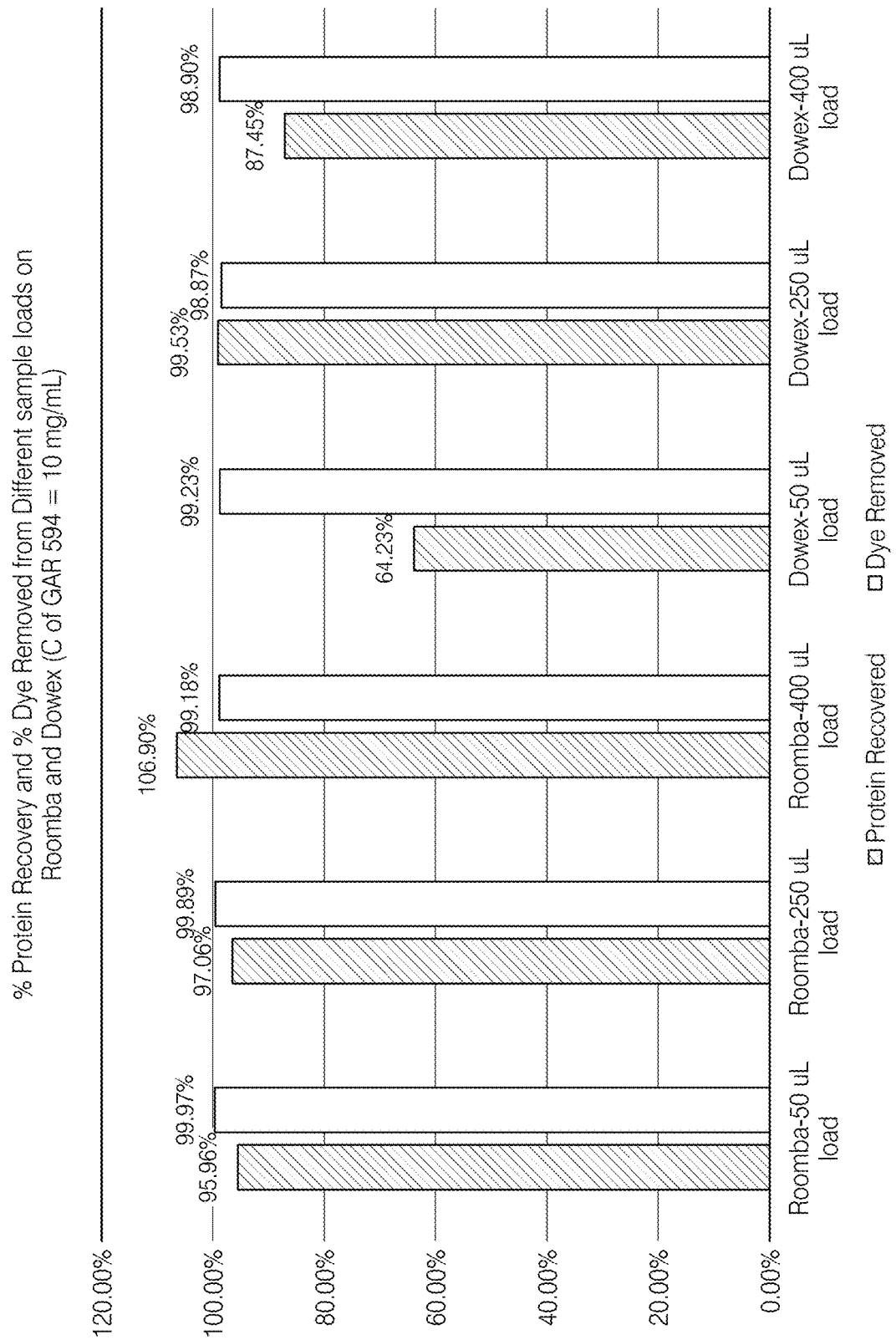
Figure 31A:
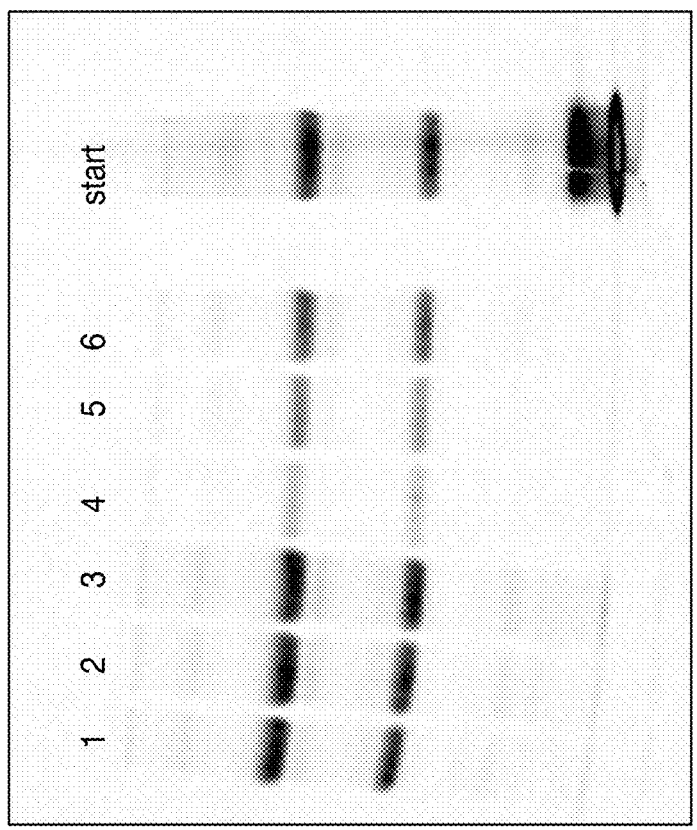
FIG. 31A and FIG. 31B depict comparison of protein recovery and dye removal compositions, devices and methods of the present disclosure (Roomba) with an ion exchange resin (Dowex), according to one embodiment.

Two concentrations of Goat Anti Rabbit Alexa Fluor™ 594 conjugate ("GAR-594") were used for this experiment—1 mg/mL (gel depicted in FIG. 30A) and 10 mg/mL (gel depicted in FIG. 31A).
Supports Used in FIGS. 30A, 30B, 31A and 31B:
Lane 1-3 used a Dextran PEG Diamine blend (a composition of the disclosure), labeled as Roomba in FIGS. 30A-31B.
Lanes 4-6 used the Dowex (unmodified ion exchange resin)
Volume of Antibody Dye Conjugate Used in FIGS. 30A, 30B, 31A and 31B:
Lane 1 and Lane 4—50 μl
Lane 2 and Lane 5—250 μl
Lane 3 and Lane 6—400 μl
Lane Start—Uncleaned sample (10 mg/mL GAR-594 conjugate FIG. 30A or 1 mg/mL GAR-594 conjugate FIG. 31B)

Figure 31B:
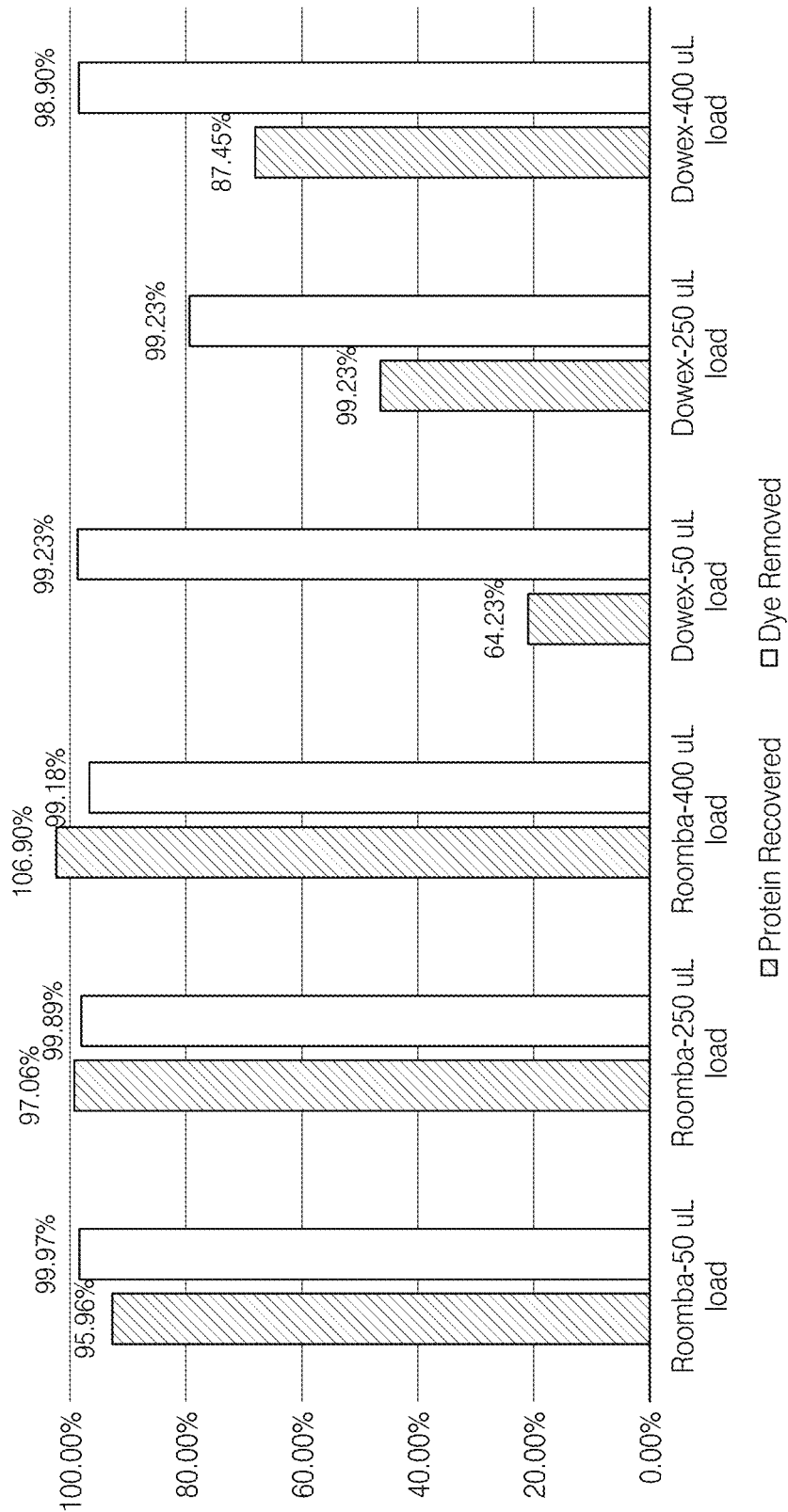

Results of these Experiments are depicted in the gels of FIGS. 30A and 31B and in the bar graphs of FIG. 30B and FIG. 31B.

FIGS. 30A and 30B depicts removal of another exemplary small molecule a free dye, Alexa Fluor™ 594, when added at different volumes (50 μl, 250 μl and 400 μl) to a dye antibody conjugate of 10 mg/mL to spin-columns having different supports, i.e., a composition of the present disclosure, a Dextran PEG 20K blend (labeled as Roomba in FIGS. 30A and 30B), and a pure ion exchange resin (unmodified ion exchange resin), Dowex.

The lane labeled "start" shows the "uncleaned" sample passed as described in sections above (which corresponds to the positive control where the unbound dye from the protein mix is not spun to remove dye. The top two bands in Lane "start" correspond to the reduced Antibody (light chain and heavy chain). The bottom band corresponds to the free dye, Alexa Fluor™ 594. In FIG. 30A, lanes 1, 2 and 3 show good protein recovery when the top two bands are compared to the "start" lane. In addition, the bottom free dye band is missing in Lanes 1-3 which indicates removal of free dye by the spin column with a resin composition of the disclosure. In comparison, Lane 4, shows loss of protein recovery with the ion exchange resin when the conjugate was added at 50 μl to the unmodified ion-exchange resin bed. This indicates that when a 10 mg/mL GAR-Alexa Fluor™ 594 conjugate is added at 50 μl to 500 μl of a resin bed, the resin bed having a composition of the disclosure a Dextran-PEG Diamine resin blend, we get good recovery with the Dextran-PEG diamine blend, whereas protein yield is lost in the Dowex resin. The graphs generated using iBright Analysis Software correlate very well with the image.

FIG. 31A depicts removal of small molecule a free dye, Alexa Fluor™ 594, when added at different volumes (50 μl, 250 μl and 400 μl) of a dye antibody conjugate of 1 mg/mL using different supports i.e., a composition of the present disclosure, a Dextran PEG 20K blend, and a pure ion exchange resin (unmodified ion exchange resin), Dowex.

The lane labeled "start" shows the "uncleaned" (positive control) sample processed as described in sections above. The top two bands in Lane "start" correspond to the reduced Antibody (light chain and heavy chain). The bottom band corresponds to the free dye Alexa Fluor™ 594. Lanes 1, 2 and 3 in FIG. 31A show good protein recovery when the top two bands are compared to the "start" lane. In addition, the bottom free dye band is missing in Lanes 1-3 which indicates removal of free dye by the composition of the disclosure. Lanes 4, 5 and 6, shows loss of protein recovery with the ion exchange resin when the 1 mg/mL Antibody Dye conjugate was added at 50 μl, 250 μl and 400 μl to the resin bed. This indicates that at all volumes tested 50 μl, 250 μl, 400 μl of GAR-Alexa Fluor™ 594 conjugate at 1 mg/mL, protein recovery is poor with the Dowex resin when compared to the Dextran-PEG Diamine blended resin. The graphs generated using iBright Analysis Software correlate very well with the image.

The bar graphs shown in FIGS. 30B and 31B quantify percentage of protein recovery and percentage of dye removed and show >90% protein recovery with compositions of the disclosure (depicted as Roomba in FIGS. 30B and 31B) when 0.05 mg to 4 mg of GAR 594 Ab-dye conjugate is loaded with a >90% dye removal.

In comparison, the Dowex provides >90% protein recovery with >90% dye removal, however only at much higher concentrations of protein at the lower scale, i.e., when 2.5 mgs to 4 mgs of GAR 594 Ab-Dye conjugate is loaded.

This data shows compositions of the disclosure provide a greater flexibility, of about 50× more flexibility, and allow for protein recovery in a wider range of sample protein concentrations and volumes as compared to an unmodified ion exchange only resin (such as Dowex).

Accordingly, this example demonstrates that compositions of the disclosure achieve high protein recovery as well as efficient small molecule removal (removal of substantially all small molecules) across a wide range of low and high sample protein concentrations and high and low sample protein volumes. In contrast, the ion-exchanger Dowex is limited in that it only works at high sample protein concentrations and high volumes of proteins but does not efficiently remove small molecules or have high protein recovery at lower sample protein volumes and concentrations. Advantageously, the present compositions, devices and methods provide much higher protein recovery even when very small concentrations of sample protein are to be purified from small molecule contaminants.

The experiments described above were done with Dowex or the compositions of the disclosure placed in spin columns. In other experiments (data not shown), batch processing for small molecule removal was done in large batches for compositions of the disclosure versus Dowex. The method involved taking large batches of dried resins of either compositions of the disclosure or Dowex; adding in a protein conjugated to a small molecule that may have free floating small molecule contaminants (such as an Antibody-dye conjugate); mixing the dried resins with the protein conjugated to the small molecule; and collecting the conjugated protein in the filtrate where the free unbound small molecules bind to the Dowex or the compositions of the disclosure. In these experiments, it is noted that using the pure ion exchange column Dowex, required a change in pH (reduced pH) to allow the ion exchanger to bind the small molecule. This additional pH change step was not required for compositions of the disclosure. Thus, an additional advantage of the compositions of the disclosure is reduced number of steps and ease of separation.

Each embodiment disclosed herein may be used or otherwise combined with any of the other embodiments disclosed. Any element of any embodiment may be used in any embodiment. Although the claimed embodiments have been described with reference to specific example embodiments, it will be understood by those skilled in the art that various changes may be made and equivalents may be substituted for elements thereof without departing from the true spirit and scope of the claimed invention. In addition, modification may be made without departing from the essential teachings of the invention.

What is claimed is:

1. A composition for separating one or more small molecules from a sample, the composition comprising:
    a first size exclusion support comprising a polyacrylamide, a cellulose material, a hydroxyethyl cellulose, and/or derivatives thereof; and
    a first moiety that is immobilized onto the first size exclusion support, wherein the first moiety can associate with the one or more small molecules to separate the one or more small molecules from a sample.

2. The composition of claim 1, comprising a second moiety that is different from the first moiety, wherein the second moiety is immobilized onto the first size exclusion support.

3. The composition of claim 1, further comprising a second size exclusion support that is different from the first size exclusion support.

4. The composition of claim 3, wherein the second size exclusion support comprises a dextran polymer or agarose.

5. The composition of claim 1, wherein the first moiety comprises a polysaccharide, a dextran, a polyethylene glycol polymer, an amine-containing polymer, a polyaminoacid, a lipopolysaccharide, an antibiotic, a chelating group, a magnetic particle, a paramagnetic particle, a functional group, an ion-exchanger, or any combination thereof.

6. The composition of claim 5, wherein the amine-containing polymer is a poly(ethylene glycol)diamine, a polyethylenediamine, a polyethyleneimine that is linear, or a polyethyleneimine that is branched.

7. The composition of claim 6, wherein the polyethyleneimine that is linear, is diethylenediamine.

8. The composition of claim 5, wherein the first moiety is a dextran.

9. The composition of claim 8, wherein the dextran has a molecular weight in the range of from about 6 kDa-2800 kDa.

10. The composition of claim 1, wherein the first moiety associates with the one or more small molecules by charge interaction, hydrophilic interactions, hydrophobic interactions, affinity interaction, hydrogen bonding, or Van der Waals forces.

11. The composition of claim 1, wherein the one or more small molecules have a molecular weight range of <2000 Da.

12. The composition of claim 1, wherein the one or more small molecules independently are selected from an unreacted or partially reacted label or nonoparticle, or a derivative thereof; a dye or derivative thereof; a radioactive ligand or an intermediate thereof; a mass tag; a metal; biotin or a derivative thereof; a crosslinker or derivative thereof; a reducing agent or derivative thereof; or any combination thereof.

13. The composition of claim 1, wherein the sample comprises a biomolecule, a protein a glycoprotein, an antibody, a peptide, a nucleic acid, a polysaccharide, a carbohydrate or a lipid and wherein contacting the sample with the composition substantially reduces a quantity of the one or more small molecules in the sample.

14. A device for separating one or more small molecules from a sample, the device comprising:
 a) a container comprising a composition for separating one or more small molecules from a sample, the composition comprising (i) a first size exclusion support comprising a polyacrylamide, a cellulose material, a hydroxyethyl cellulose, and/or derivatives thereof; and (ii) a first moiety that is immobilized onto the first size exclusion support; wherein the first moiety can associate with the one or more small molecules to separate the one or more small molecules from the sample; and
 b) a receptacle located below the container.

15. The device of claim 14, operably configured to be subject to a gravity flow, a centrifugal force, a positive pressure, a negative pressure, vacuum, or any combination thereof.

16. The device of claim 14, wherein the container is a columnar container, a tube, a multi-well tube, a multi-well plate, or a multi-well filter plate.

17. A system for separating one or more small molecules from a sample, the system comprising:
 a) a container comprising a composition for separating one or more small molecules from a sample, the composition comprising (i) a first size exclusion support comprising a polyacrylamide, a cellulose material, a hydroxyethyl cellulose, and/or derivatives thereof; and (ii) a first moiety that is immobilized onto the first size exclusion support, wherein the firtst moiety can associate with the one or more small molecules to separate the one or more samll molecules from the sample;
 b) a receptacle located below the container; and
 c) a means to subject the container and receptacle to a gravity flow, a centrifugal force, a positive pressure, a negative pressure, vacuum, or any combinations thereof.

18. A kit for separating a biomolecule from one or more small molecules comprising:
 the device of claim 14, wherein the device is operably configured to be subject to a gravity flow, a centrifugal force, a positive pressure, a negative pressure, vacuum, or any combination thereof.

19. A method for separating at least one biomolecule from one or more small molecules, the method comprising:
 a) applying a sample comprising the at least one biomolecule to a composition comprising (i) a first size exclusion support comprising a polyacrylamide, a cellulose material, a hydroxyethyl cellulose, and/or derivatives thereof; and (ii) a first moiety that is immobilized onto the first size exclusion support; and
 b) subjecting the container to a gravity flow, a centrifugal force, a positive pressure, a negative pressure, a vacuum, or any combination thereof,
 wherein the at least one biomolecule in the sample is excluded through the composition and is collected as a flow through, and wherein the one or more small molecules associates with the first one moiety and is thereby separated from the at least one biomolecule.

* * * * *

UNITED STATES PATENT AND TRADEMARK OFFICE
CERTIFICATE OF CORRECTION

PATENT NO. : 11,975,306 B2
APPLICATION NO. : 17/016140
DATED : May 7, 2024
INVENTOR(S) : Ramesh Ganapathy et al.

It is certified that error appears in the above-identified patent and that said Letters Patent is hereby corrected as shown below:

In the Claims

Column 41, Lines 23-26, Claim 12 "The composition of claim 1, wherein the one or more small molecules independently are selected from an unreacted or partially reacted label or nonoparticle, or a derivative thereof;" should read -- "The composition of claim 1, wherein the one or more small molecules independently are selected from an unreacted or partially reacted label or nanoparticle, or a derivative thereof;" --

Column 42, Lines 16-18, Claim 17 "and (ii) a first moiety that is immobilized onto the first size exclusion support, wherein the firtst moiety can associate with the one or more small molecules to" should read -- "and (ii) a first moiety that is immobilized onto the first size exclusion support, wherein the first moiety can associate with the one or more small molecules to" --

Column 42, Lines 18-20, Claim 17 "small molecules to separate the one or more samll molecules from the sample;" should read -- "small molecules to separate the one or more small molecules from the sample;" --

Signed and Sealed this
Seventeenth Day of September, 2024

Katherine Kelly Vidal
*Director of the United States Patent and Trademark Office*